United States Patent
Marshall et al.

(10) Patent No.: US 9,625,378 B2
(45) Date of Patent: *Apr. 18, 2017

(54) FLUID ANALYZER WITH MODULATION FOR LIQUIDS AND GASES

(71) Applicant: Redshift Systems Corporation, Burlington, MA (US)

(72) Inventors: Charles McAlister Marshall, North Andover, MA (US); Donald Kuehl, Windham, NH (US); Jeffrey Guasto, Chestnut Hill, MA (US)

(73) Assignee: Redshift Bioanalytics, Inc., Burlington, MA (US)

(*) Notice: Subject to any disclaimer, the term of this patent is extended or adjusted under 35 U.S.C. 154(b) by 100 days.

This patent is subject to a terminal disclaimer.

(21) Appl. No.: 14/673,015

(22) Filed: Mar. 30, 2015

(65) Prior Publication Data
US 2015/0276588 A1 Oct. 1, 2015

Related U.S. Application Data

(60) Provisional application No. 61/972,823, filed on Mar. 31, 2014, provisional application No. 62/039,666, (Continued)

(51) Int. Cl.
*G01N 21/39* (2006.01)
*G01N 21/17* (2006.01)
(Continued)

(52) U.S. Cl.
CPC ......... *G01N 21/39* (2013.01); *G01N 21/1717* (2013.01); *G01N 21/35* (2013.01);
(Continued)

(58) Field of Classification Search
CPC .................................................. G01N 21/1717
See application file for complete search history.

(56) References Cited

U.S. PATENT DOCUMENTS 3,381,134 A * 4/1968 Wolf .................... G01F 1/86
250/575
5,886,247 A 3/1999 Rabbett
(Continued)

OTHER PUBLICATIONS

International Search Report for International Application No. PCT/US2015/023324 mailed from the International Searching Authority on Jul. 13, 2015, 9 pages.

*Primary Examiner* — Christine Sung
(74) *Attorney, Agent, or Firm* — BainwoodHuang

(57) ABSTRACT

A fluid analyzer includes an optical source and an optical detector defining an optical beam path through an interrogation region of a fluid flow cell. Flow-control devices conduct analyte and reference fluids through a channel and the interrogation region, and manipulate fluid flow in response to control signals to move a fluid boundary separating the analyte and reference fluids across the interrogation region. A controller generates control signals to (1) cause the fluid boundary to be moved across the interrogation region accordingly, (2) sample an output signal from the optical detector at a first interval during which the interrogation region contains more analyte fluid than reference fluid and at a second interval during which the interrogation region contains more reference fluid than analyte fluid, and (3) determine from samples of the output signal a measurement value indicative of an optically measured characteristic of the analyte fluid.

28 Claims, 32 Drawing Sheets

Related U.S. Application Data filed on Aug. 20, 2014, provisional application No. 62/074,916, filed on Nov. 4, 2014.

(51) Int. Cl.
    *G01N 21/35*     (2014.01)
    *G01N 21/85*     (2006.01)

(52) U.S. Cl.
    CPC ..... *G01N 21/85* (2013.01); *G01N 2021/1723* (2013.01); *G01N 2021/399* (2013.01)

(56) References Cited

U.S. PATENT DOCUMENTS

| | | |
|---|---|---|
| 8,502,148 B2 * | 8/2013 | Wagner ............... C12N 5/0612 250/338.1 |
| 8,941,062 B2 | 1/2015 | Wagner et al. |
| 8,981,298 B2 | 3/2015 | Wagner et al. |
| 9,003,869 B2 | 4/2015 | Wagner et al. |
| 9,377,400 B2 * | 6/2016 | Wagner ................. G01N 21/39 |
| 2003/0022388 A1 | 1/2003 | Roos et al. |
| 2004/0145741 A1 | 7/2004 | Cole et al. |
| 2010/0182605 A1 * | 7/2010 | Stockwell ................ G01J 3/12 356/436 |
| 2011/0000796 A1 | 1/2011 | Situ et al. |
| 2013/0110467 A1 * | 5/2013 | Feller .................... G01N 21/05 702/191 |
| 2013/0210128 A1 | 8/2013 | Rothberg et al. |
| 2014/0049777 A1 * | 2/2014 | Sun .......................... G01J 3/42 356/409 |
| 2015/0099274 A1 * | 4/2015 | Axelrod ................ C12M 41/34 435/39 |

\* cited by examiner

FLUID ANALYZER WITH MODULATION FOR LIQUIDS AND GASES

SUMMARY

Mid-infrared (Mid-IR) spectroscopy is a powerful tool for both qualitative and quantitative measurements of organic materials due to the unique spectroscopic fingerprint accessible in the Mid-IR. However, measurements of low concentrations of analytes using Mid-IR spectroscopy can present a challenge for numerous reasons including: (1) strong background absorbance due to highly absorbing background matrices such as water or other highly polar solvents which limits the allowable sample pathlength, (2) interferences that overlap with the analyte making the direct measurement of the analyte absorption features difficult, (3) weak, broad spectral features which are difficult or impossible to discriminate from low frequency drifts in the instrumentation optical source, detector, and electronics.

One approach to address some of these limitations is to introduce two measurement channels in the system, one with the analyte plus the background matrix (e.g. solvent in a liquid sample), the "Sample Channel", the other containing the background matrix with no analyte, the "Reference Channel". The sample and reference channel are then each measured, either successively or in parallel, and the results are ratioed to obtain the desired "transmission" spectrum. At low analyte concentrations, the background matrix in the sample and reference channel are essentially identical, and thus cancel out, making extraction of the small absorption features of the analyte easier to interpret. This method can be accomplished in a number or ways.

One technique is "pseudo" dual beam in time (as for FTIR). In this case there is only one measurement channel and the sample and reference cell are alternately placed in the measurement channel. The (computer stored) Sample and Reference measurements are then ratioed to obtain the transmission spectrum. This approach requires a very stable system including source, electronics, and detector as any small drift will add noise to the measurement. It also requires either matching to identical sampling cells, or flushing and refilling a single cell.

Another approach is to switch the beam between two optical paths. While this can be substantially faster, it is very difficult to match the two channels exactly, it is optically complex, and the sampling cells must also match closely.

Dual beam optical subtraction involves the optical difference measurement from the two output beams of an interferometer which are 180 degrees out of phase. Again, it is difficult to match channels, is optically complex, and two matched cells are still required.

Dual beam with two detectors and channels is another approach. While both beams can be measured simultaneously, in addition to matching the two optical channels, the detectors must also be matched making the measurement even more difficult.

With conventional grating based scanning instruments, or with tunable lasers, a dual beam system can be used in which a mechanical chopper rapidly alternates the beam path between two optical paths as the system scans across the spectrum. This rapid modulation improves the signal to noise, but still suffers from the difficulty of matching the optical paths and sampling cells.

These methods all require a very stable source, detector, and electronics, precise optical matching of the two optical channels and sampling cells, or some combination of these requirements. In addition, they all add complexity to the measurement.

One very effective method of minimizing these limitations is modulation spectroscopy. In modulation spectroscopy, one or more of the modulations are imposed on either the measuring device, or the sample. This allows for a detection method whereby only the specific frequency of modulation, and/or its higher frequency overtones needs to be detected. By doing so, one eliminates the noise sources contributing to the measurements that fall outside of the modulation frequencies. This also works to eliminate the problem of low frequency drifts that is inherent to the conventional two beam ratio methods described.

An example of modulation spectroscopy is in the measurement of a narrow gas lines by laser spectroscopy (wavelength modulation spectroscopy (WMS) and frequency modulation spectroscopy (FMS) as known in the art). In WMS, the laser wavelength is modulated in a wavelength range considerably smaller than the linewidth of the gas line being measured. Scanning over the line of interest and using a lock-in amplifier at the modulation frequency, or preferably at the higher order frequencies, will limit the measurement bandwidth of the signal and significantly improve the signal to noise. This still does not fully eliminate the effects of low frequency drift in the source, detector, and electronics, but if a narrow spectral region is measured, it can be scanned fast enough to minimize this noise source. Other methods of modulating the measuring device include amplitude modulation, mechanical modulation using a mechanical chopper, and optical modulation such as with a photo-elastic modulator. An interferometer inherently works by modulating all measured wavelengths simultaneously, at different frequencies. But it still suffers from the problem of long term drift.

Frequency modulation of the source will also help minimize background interferences, provided that the background is significantly broader than the line measured. This is accomplished by using the higher-order derivatives derived from the modulation scheme.

For broad spectral features, the frequency modulation technique breaks down due to the difficulty in rapidly modulating with repeatable power over a very large frequency range, and from the additional challenge of interfering bands over the broader spectral range. Scanning over a broad spectral range is also less efficient, as the measurement must usually be extended to cover baseline points far from the peak absorbance, so less time is spent measuring the maximum signal of the analyte of interest.

Mid-IR lasers, such as QCLs, provide a tunable Mid-IR light source with many orders of magnitude more brightness then the traditional Mid-IR thermal sources used in conventional FTIR and scanning spectrometers. In addition, if operated in continuous wavelength (CW) mode, the laser linewidth can be very narrow, much narrower than the rotational linewidth of typical small molecule gases. This makes them ideally suited to the measurement of such gases for a number of reasons. First, the high brightness allows for very long pathlengths to be used that will increase the amount of sample measured thereby increasing the sensitivity by virtue of the Beer-Lambert law. Second, since the resolution of the measurement is greater than the measured linewidth, the measured amplitude of the line is much greater, and thus easier to detect, than when compared to a lower resolution measurement where, for example, the spectrometer resolution is less than the sample linewidth, whereupon—the measured amplitude is less. This speaks directly as to why the performance of a typical FTIR instrument with a linewidth of 8 cm$^{-1}$ is significantly disadvantaged relative to a laser with a linewidth of <0.001 cm$^{-1}$ when measuring 0.1 cm$^{-1}$ wide gas absorption lines.

For the measurement of broad lines, typical of condensed phase samples or higher molecular weight gas phase samples (where the sharp rotational structure is not resolved), Mid-IR light sources gain no advantage from their higher resolution. However, the increased brightness can enable enhanced sensitivity for trace samples in strongly absorbing matrices, such as water, highly polar solvents or in the presence of high concentrations of strong absorbers. For example, in condensed phase measurements through a water cell, pathlengths for conventional FTIR and scanning IR using thermal infrared sources may be limited to about 5-20 um due to the strong absorbance of the matrix.

The brightness of the Mid-IR laser enables the use of greater pathlength transmission cells which allows for much longer optical pathlength cells (100+ um) for measuring samples in liquids such as water. This will improve both measurement sensitivity, and provide a more robust sampling system less prone to clogging and high back pressure when used for on-line measurement. Likewise, for other systems in which there is a strong absorbing background, such as methane in natural gas, longer pathlengths can be used to improve the detection of trace constituents such as H$_2$O or H$_2$S.

An alternative to short pathlength transmission cells for aqueous phase measurements, which are prone to high back pressure and clogging, are Attenuated Total Reflection (ATR) cells. ATR methods can be used to improve the flow while providing the short pathlengths necessary using conventional IR spectroscopy. However, they introduce more complex optics, typically higher cell volumes, are more expensive, don't always provide good laminar flow, and are difficult to clean.

However, using Mid-IR lasers for broad linewidth measurements is problematic. For such measurements it would be optimal to measure the broad line at its peak amplitude. But a baseline point must also be measured, which means scanning back and forth between the peak and the baseline. When scanning between the peak and the baseline, the power of the laser at the point in time of each measurement must be accurately known to accurately measure low concentrations of the analyte concentration. In addition, the laser, detector, electronics, and even the sample can drift in the time between the peak and baseline measurements and the error can be indistinguishable from changes in the peak amplitude, and hence are a source of noise. Finally, the broad lines limit the use of instrument modulation techniques such as frequency modulation due to the difficulty in modulating the laser over such a large linewidth at high frequencies (e.g. 100 Hz).

A fluid analyzer is disclosed that includes an optical source and an optical detector defining an optical beam path through an interrogation region of a fluid flow cell. Flow-control devices conduct analyte and reference fluids through a channel and the interrogation region, and manipulate fluid flow in response to control signals to move a fluid boundary separating the analyte and reference fluids across the interrogation region. A controller generates control signals to (1) cause the fluid boundary to be moved across the interrogation region accordingly, (2) sample an output signal from the optical detector at a first interval during which the interrogation region contains more analyte fluid than reference fluid and at a second interval during which the interrogation region contains more reference fluid than analyte fluid, and (3) determine from output signal samples a measurement value indicative of an optically measured characteristic of the analyte fluid.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

DETAILED DESCRIPTION

Figure 1:
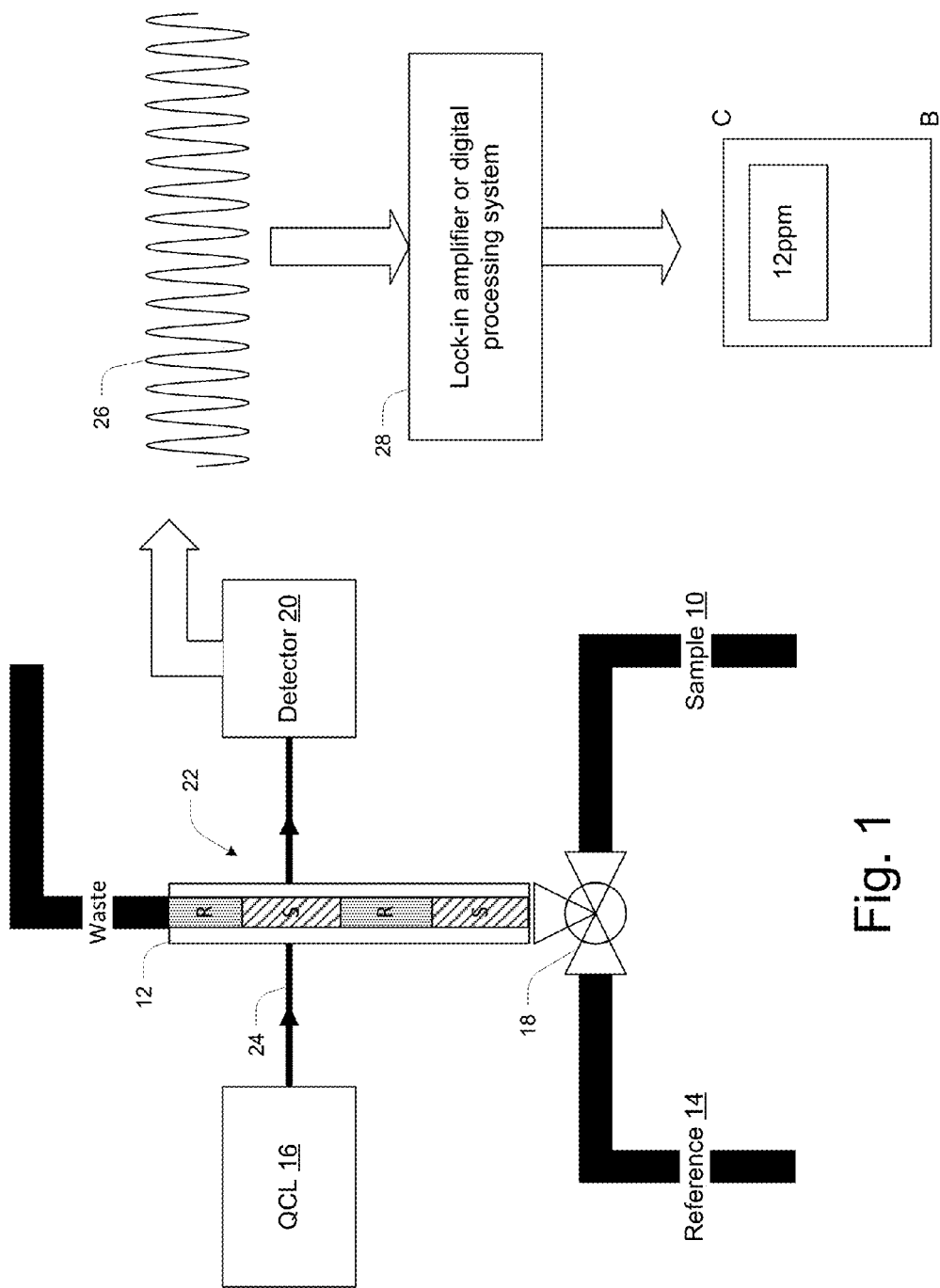
FIG. 1 is a schematic diagram of a fluid analyzer.

This description employs certain terminology for which the following general descriptions are provided below but each term may be further described or otherwise modified within a specific embodiment:

Solvent—Bulk liquid (or gas) in which analytes are dissolved in solution or suspended as an emulsion Analyte—Compound of interest to characterize, quantitate or identify dissolved in or mixed as an emulsion in solvent Solution—The bulk liquid (or gas) constituting the solvent, analyte(s) of interest, and possibly other compounds both interfering and non-interfering. Liquids would also include other liquid-like physical states such as super critical fluids. Liquids could also include suspended particles or living cells in solution, emulsions, and biological liquids such a whole blood, urine, or interstitial fluids.

Background or Background Matrix—All the constituents of the sample excluding the analyte(s)

Reference—The substance used to provide a baseline in a differential measurement system Sample—The substance containing one or more analytes (absence of one or more analytes) in a differential measurement system. The sample stream may also be referred to as the analyte stream.

Pathlength—The distance the optical beam travels through the fluid channel of the fluid cell, as may be determined for example by (1) the separation of inner top and bottom window surfaces of the fluid cell at the interrogation region, or (2) the length of travel of an optical beam through a fluid to be measured in the interrogation region. The latter may be referred to as the effective pathlength and may be less than the window separation due to the presence of other fluids or substances in the interrogation region.

Interrogation region (or area)—The region of interaction between the substance under test (e.g. the analyte) and the light source. For example, the interrogation region may be determined by the diameter of the optical beam times the pathlength.

Microfluidic cell, fluid flow cell or optical cell—An object containing fluids or gases where the fluids or gases can be moved into an interrogation region.

Analyzer—Combination of an optical source, optical cell, and optical detector or transducer used to measure an analyte Fluid Boundary or Interface—the region where the reference and sample fluids are in contact.

In this description a mid-infrared (Mid-IR) quantum cascade laser (QCL) source may be referred to as the optical source. It should be noted, that the source does not have to be a Mid-IR source or even a laser. While a Mid-IR laser is used as an example, the method is also appropriate for other types of spectroscopy including, but not limited to, UV-Visible, Near Infrared, Raman, and fluorescence spectroscopy. The instrument can be a tunable source, such as a laser or other high intensity source, or may be a conventional spectrometer such as a scanning grating system, a filter based system, or FTIR using a conventional source.

It should also be recognized that this technique may also apply to non-optical techniques of measurement where it may be advantageous to compare a sample and reference. Examples may include conductivity measurements using electrodes or inductive loops, calorimetry, and pH. In such an example, the interrogation may not be optical but instead is determined by the detection mechanism's interaction with the solutions, such as the electrical or magnetic path when measuring conductivity.

Novel methods are described which allow for the rapid modulation of the measured sample to improve the sensitivity and accuracy of the measurement of low levels of analyte. The modulation occurs between the measurement of a sample and a reference fluid. The reference fluid may be a blank (i.e. transparent or very weak absorber) medium, in which case the reference provides a zero reference, or it may be a representative matrix of the sample background without the presence of the analyte of interest, thereby effectively canceling out background interferences and allowing a direct measurement of the analyte of interest, free from background. The reference may be identical to the sample except containing analyte or analytes to be measured at known concentration (e.g. a target level wherein the analyzer measures deviation from a target value).

FIG. 1 shows a first embodiment in which a liquid sample solution 10 containing an analyte of interest is introduced into a fluid flow cell (or "flow cell") 12 in either a continuous flowing stream, or in a flow-stop-measure-start-flow repeating sequence. In the flowing stream, a reference solution 14 (the order of sample and reference can be reversed) is introduced into the flow stream in such a manner as to create alternating segments or plugs in the flow stream of sample 10 and reference 14 materials. These alternating segments are shown as S for sample and R for reference. A Mid-IR source 16, such as a fixed frequency or tunable QCL laser 16 as shown, or one or more lasers, is tuned to a suitable wavelength for measuring the analyte(s) of interest, such as the peak of an absorbance feature chosen to minimize background interferences. The Mid-IR source 16 may be coupled to the fluid flow cell 12 through a fiber. The reference material is chosen as a suitable blank, such as pure solvent, a gas, or a suitable reference material or mixture representative of the sample background. The reference may be inserted into the sample stream using microfluidic techniques such as valves, mixers, pumps, or the use of pressure to alternate the sample and reference streams, all as known in the art. In the illustrated example a switching valve 18 is employed.

In this embodiment, the laser frequency (or equivalently, wavelength) is set to a value where the analyte has a strong differential absorbance relative to the reference fluid, and, in one embodiment, interferences (i.e. absorption from substances not of interest in the measurement) are minimal. Since the reference 14 has a different absorbance than the sample 10 at this frequency, the signal at a detector 20 is modulated as the sample and reference pass through the beam 24. The modulated waveform 26 produced by the detector may then be processed by a component 28 which may be a lock-in amplifier or a digital signal processing system to produce a value which is proportional to the analyte concentration. The fluid modulation waveform produced by the system controller may control how the sample and reference solutions are introduced. For example, a rapid switching of the valve 18 interspersed with comparatively long periods of steady flow can create sharper boundaries between the sample and the reference with minimal mixing, resulting in a waveform that may be more square in form. Valves could also be controlled in such a manner as to create a mixing that blends the reference and sample solution in a smooth gradient, creating alternative waveforms, by way of example sinusoidal or triangular. Other waveforms could be created in this manner as well.

A key advantage is that the laser beam used to sample the cell 12 may be held motionless. Lasers, particularly CW lasers which can have higher signal to noise ratios than pulsed lasers, are prone to many optical effects in the presence of beam motion that can degrade performance. These include speckle, diffraction, feedback into the laser, mechanical repeatability, etc. If the laser beam is steered or translated alternatively between two sample cells or areas within the sample cell, performance can thereby be degraded.

Thus this embodiment allows a differential measurement or ratioing of background reference 14 and analyte sample 10 with no movement of the laser beam or change in wavelength of the laser source 16 or the detector 20.

The stream travels through the fluid flow cell 12, and the analyzer measures, continuously or intermittently, the transmission of both the sample and reference segments of the stream as they pass through an interrogation region 22 where the beam 24 meets the fluid flow cell 12. The calculation of the ratio of the absorbance of the sample and reference can be used determine the concentration of analyte of interest. Alternatively, the amplitude of the continuous modulation of the laser intensity at the detector 20 may be used to determine the concentration of the analyte. Similarly, as in wavelength modulation spectroscopy, detection schemes which take advantage of the higher orders of the modulation frequency (the rate at which the sample and reference pass through the cell) can be used to minimize the required frequency bandwidth thus rejecting noise and improving the sensitivity of the measurement.

The modulation waveform produced by the introduction of reference 14 in alternating segments would be a square wave if the sample 10 and reference 14 are discrete plugs with no mixing. One could also introduce the reference 14 into the sample stream 10 in a manner to achieve mixing in a controlled manner, to produce other modulation waveforms, such as may be achieved through variable control of the injection of the liquid. In one embodiment, the mixing is designed to achieve a sinusoidal modulation of the analyte concentration. Adjusting the modulation waveform may improve the performance of certain signal processing algorithms. Sampling of the waveform as measured by the detector 20 may include selecting a time interval during the fluid modulation of the reference and sample for sample integration such that the sampling duty cycle is less than 100%. The sampling time and location may be selected to provide the best measurement stability for purposes of co-adding the measurements to achieve better signal to noise and sensitivity. The sampling times for the reference 14 and sample 10 may not be the same in order to achieve a desired initial differential transmission value (e.g. 1). The timing of the sampling of reference 14 and sample 10 may be selected by analysis or measurement of the location of the boundary region between reference and sample. The timing of the sampling of reference 14 and sample 10 may be selected by analysis or measurement of the width of the boundary region between reference 14 and sample 10 (i.e. the width of the intermixing between reference and sample.

The detector 20 may be any suitable transducer for converting the optical signal to an electrical signal. By way of example, for a mid-IR source the detector may be a pyroelectric detector, a bolometer detector or a bandgap detector such as a HgCdTe photovoltaic. The optical signal may be coupled to the detector through a fiber.

To improve the modulation speed, the sample 10 and reference stream 14 could be rapidly pumped back and forth through the cell 12 rapidly, multiple times. This could be done using a pump, or by a piston type pump (not shown). In one embodiment, the channel of the transmission cell 12 may be longer than the diameter of the laser beam 24 and may contain multiple regions of sample 10 and reference 14 which are passed back and forth through the laser beam 24 by a piston. In this embodiment, the reference 14 and sample 10 may become mixed due, for example, to diffusion, dispersion, or turbulent mixing. In one embodiment, the number of passes may be limited by the diffusion rate such that the intermingled sample 10 and reference 14 are less than 50% of the size of the initial unmixed plug.

Alternatively, instead of a continuously flowing stream, rapidly filling the cell 12 alternately with the sample 10 and reference 14 streams, and performing the absorbance measurement while the sample/reference are in a static (non-flowing) state can be used. A variety of methods including switch valves can be used.

This method of sample modulation can be performed in a system for online continuous measurements, or the sample may be introduced into the system in "batch mode" whereby a static vessel is filled with the sample of interest, and the sample (and reference) is introduced into the cell from the vessel.

For the measurement process, multiple lasers may be used to simultaneously or sequentially measure multiple wavelengths for the purpose of measuring multiple analytes, or to measure sample interferences for the purpose of correcting and improving the accuracy of the measured analyte. One or more tunable lasers may be used to sequentially switch between multiple absorption lines, for the same purpose.

When measurements of emulsions, "dirty samples", or samples that are likely to leave contaminating residue in the cell are made, it is possible to add a cleaner, which in one embodiment is optically non-interfering, to the reference and/or sample streams, such as a surfactant to remove hydrophobic materials such as fats or oils, or by adding an appropriate solvent. Alternatively, a cleaning solution may be periodically introduced into the cell to flush the system and clean the cell. The cleaning solution or another third background sample may have 100% transmission to provide a measurement of the total laser power, thereby calibrating the prior relative amplitude measurement into a more accurate and calibrated absolute measurement.

The disclosed technique allows for multiple analyte samples and reference samples to be introduced into the stream, the number of analyte samples and number of references being determined by the requirements of the measurement system.

Additionally, both multiple detectors 20 and multiple optical sources 16 can be used in the system to analyze multiple components simultaneously. In some instances, a single detector 20 can be used to simultaneously measure multiple wavelength sources which can be discriminated by an additional modulation of the source or sources, such as wavelength or amplitude modulations. Another embodiment uses multiple detectors 20 with a filter element in place for each detector 20 to selectively measure the desired source wavelength.

Those versed in the art of microfluidics will recognize that the intersection of microfluidic streams may also be used to generate slugs or packets of reference and sample fluid through the variation of pressure of the intersecting streams.

Figure 3:
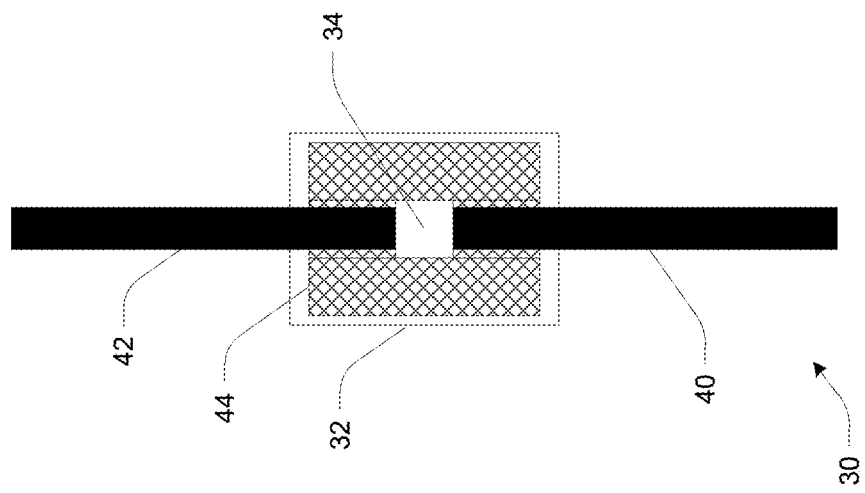
FIGS. 2-3 are schematic diagrams of flow paths of a fluid analyzer.
Figure 2:
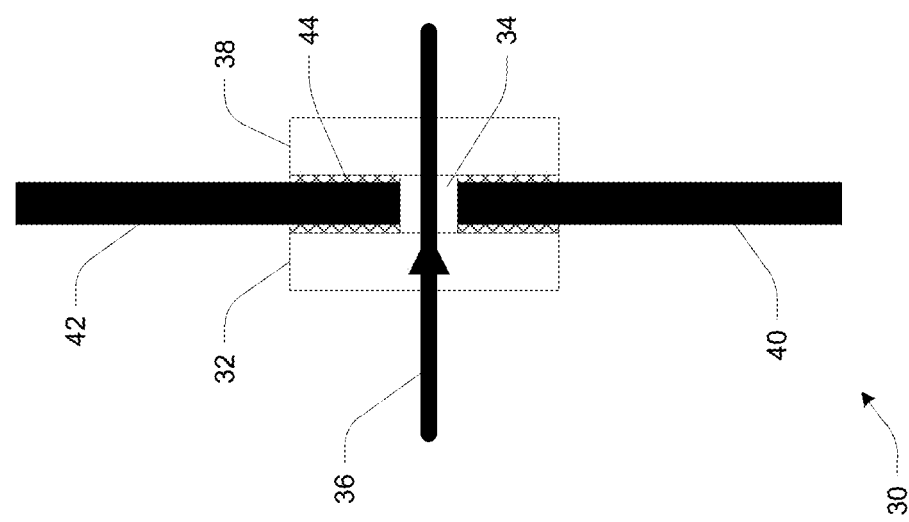

FIGS. 2 and 3 show another embodiment of a flow cell 30, with FIG. 2 showing a side view and FIG. 3 showing a front view. The flow cell 30 includes a front window 32, liquid flow region 34, beam path 36 through an interrogation region, and a back window 38. The liquid to be measured flows into the cell through inlet tubing 40 and out through outlet tubing 42. Sealing spacers and gaskets 44, flanges or other means well known in the art provide a leak free seal while minimizing turbulence. The cell 30 is designed for efficient flow below the turbulent transition. The cell 30 may be wider or longer than the size of the laser beam, which may advantageous to achieve the optimal flow characteristics. The cell 30 and switching valves (not shown) in combination with the tubing 40, 42 and cell shape are designed to avoid bubbles, mixing, and flow artifacts that would disturb the measurement. The surfaces of the windows 32, 28 may be anti-reflection coated, and the cell 30 may be angled with respect to the optical beam path 36 to avoid unwanted reflection or laser back reflections. One or more optical apertures or baffles may be used to limit the sampling region. Fluidic baffles or channels may be built into the cell to achieve the desired flow characteristics. Valves may be built into the cell 30, thereby providing a single assembly comprising both the flow cell and valves. The sampling cell window walls may be wedged (see example below) to avoid etaloning effects. The front and back windows 32, 38 may similarly be non-parallel with respect to each other to avoid optical etaloning between the cell front and back window surfaces. The cell is designed for sufficient rigidity as to not deform from flow or pressure as to otherwise compromise measurements.

Figure 4:
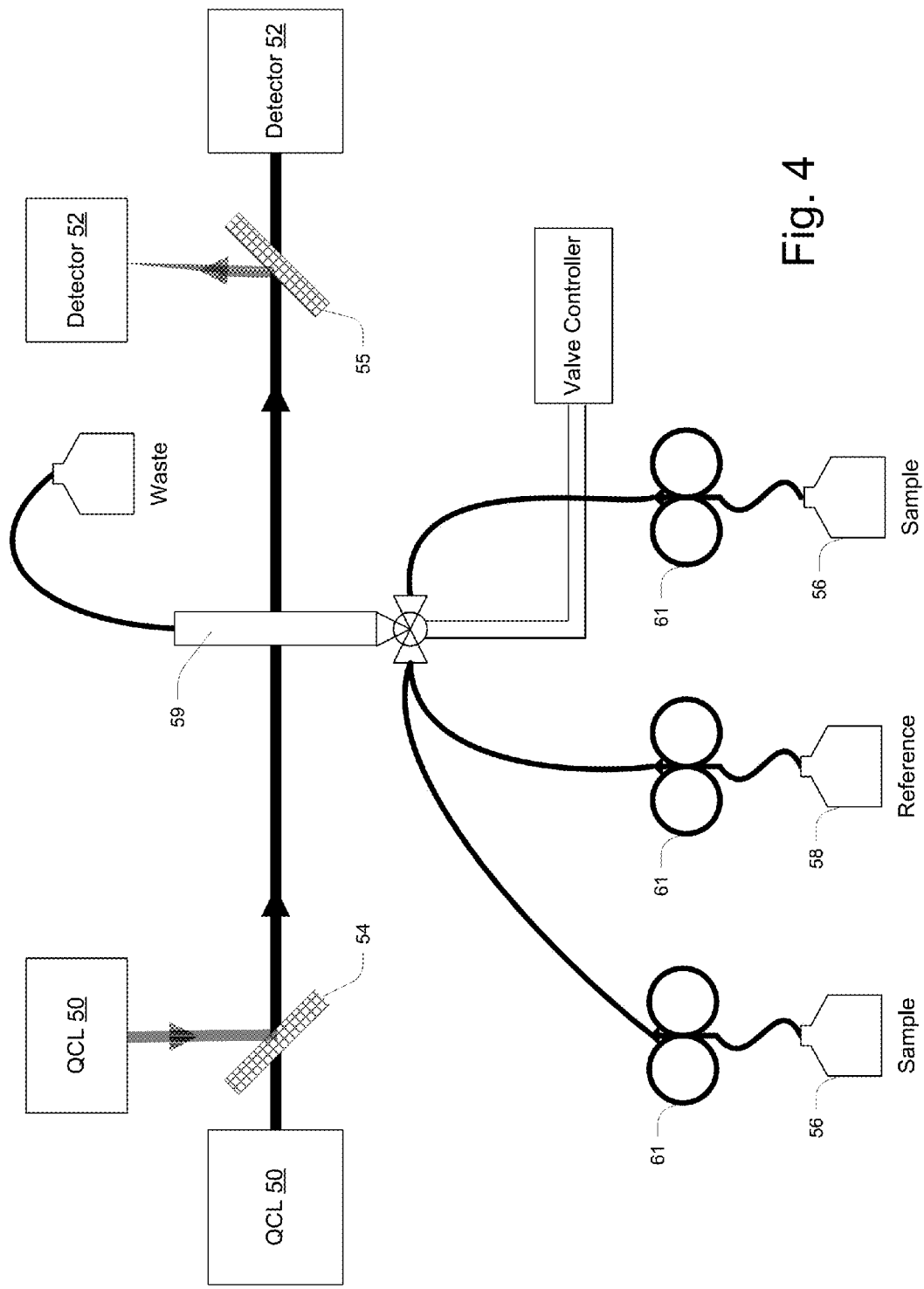
FIGS. 4-16 are schematic diagrams of fluid analyzers.

FIG. 4 shows that in alternative embodiments multiple lasers 50 and/or multiple detectors 52 may be used to measure multiple analytes simultaneously. A beam combiner 54 may be used to send multiple beams through the same sample region or the lasers 50 may be configured to sample different spatial regions simultaneously or sequentially. A beam splitter 55 may be used to separate beams and direct them to different detectors 52. The different lasers 50 may be frequency modulated so a single detector may be used to sample multiple beams for subsequent separation by signal processing techniques as is well known in the art. Multiple samples 56 and references 58 may also be used to provide for the analysis of multiple analytes in a single cell 59. These are provided to the cell 59 via pumps 61. In one embodiment, a second reference containing a known concentration of the analyte (or another analyte) can be used for calibration of the system.

In another embodiment, a series of measurement values are combined (e.g. coadded or averaged) to improve measurement sensitivity, and a likely presence of a particle or bubble in the fluid channel is detected through optical, pressure measurement or other detection methods, and samples of the detector output signal likely to have values perturbed by the particle or bubble are excluded from the series of measurement values. The particle or bubble may be detected prior to entering the interrogation region or may be detected in the interrogation region, and if detected prior to the interrogation region the time the particle or bubble enters the interrogation may be projected from the fluid or particle motion (e.g. fluid velocity and distance between the detection point and the interrogation region). The bubble or particle may not enter the interrogation region and still have an effect on the dynamics of fluid motion within the interrogation region (e.g. by effecting the motion of the fluid boundary), and thus values may still be excluded. The bubble or particle may be swept along the channel or may be become lodged in the cell channel or in the fluid paths or channels prior to entering the cell channel, and thus still effect the measurement value and require excluded values.

Figure 5:
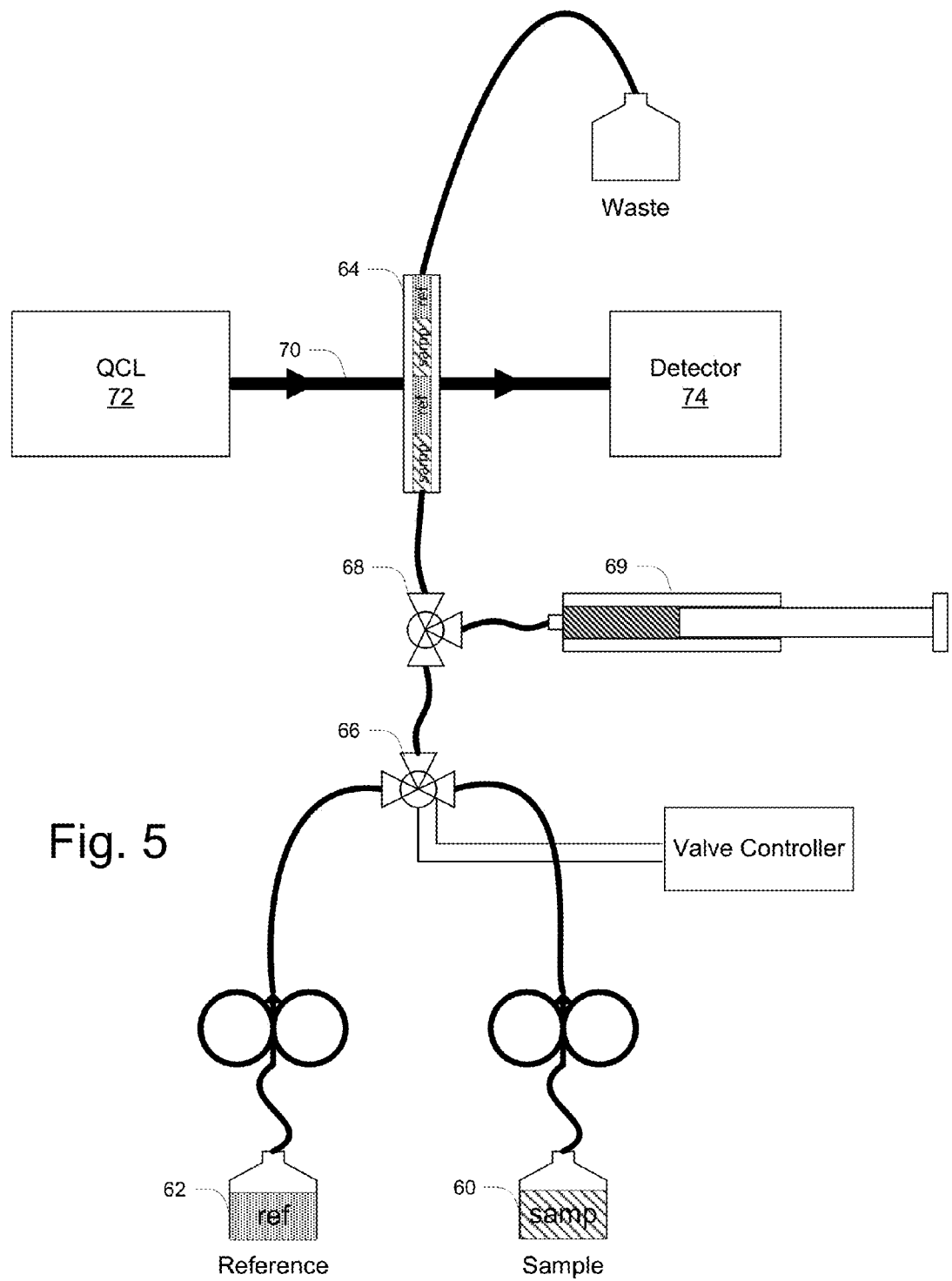

FIG. 5 shows another embodiment in which the alternating stream of sample 60 and reference 62 are introduced into the cell 64 through two switching valves 66, 68. Once the sample and reference are in the cell 64, switching valve 2 is switched to connect a syringe pump 69 to the sample inlet, and the sample and reference streams are stopped. The syringe pump 69, or other suitable device, is then used to rapidly move the fluid stream back and forth in the cell 64 at a high rate of speed. This allows for higher modulation rates of the sample/reference stream. Thus one method of scanning the liquid through the laser beam is (1) to load the flow cell 64 (or its attached tubing) with regions of reference and sample, and (2) move the regions of reference 62 and sample 60 through the laser beam 70 such that at least one reference or sample region is measured more than once without relative mechanical motion of the laser 72 or detector 74.

Figure 6:
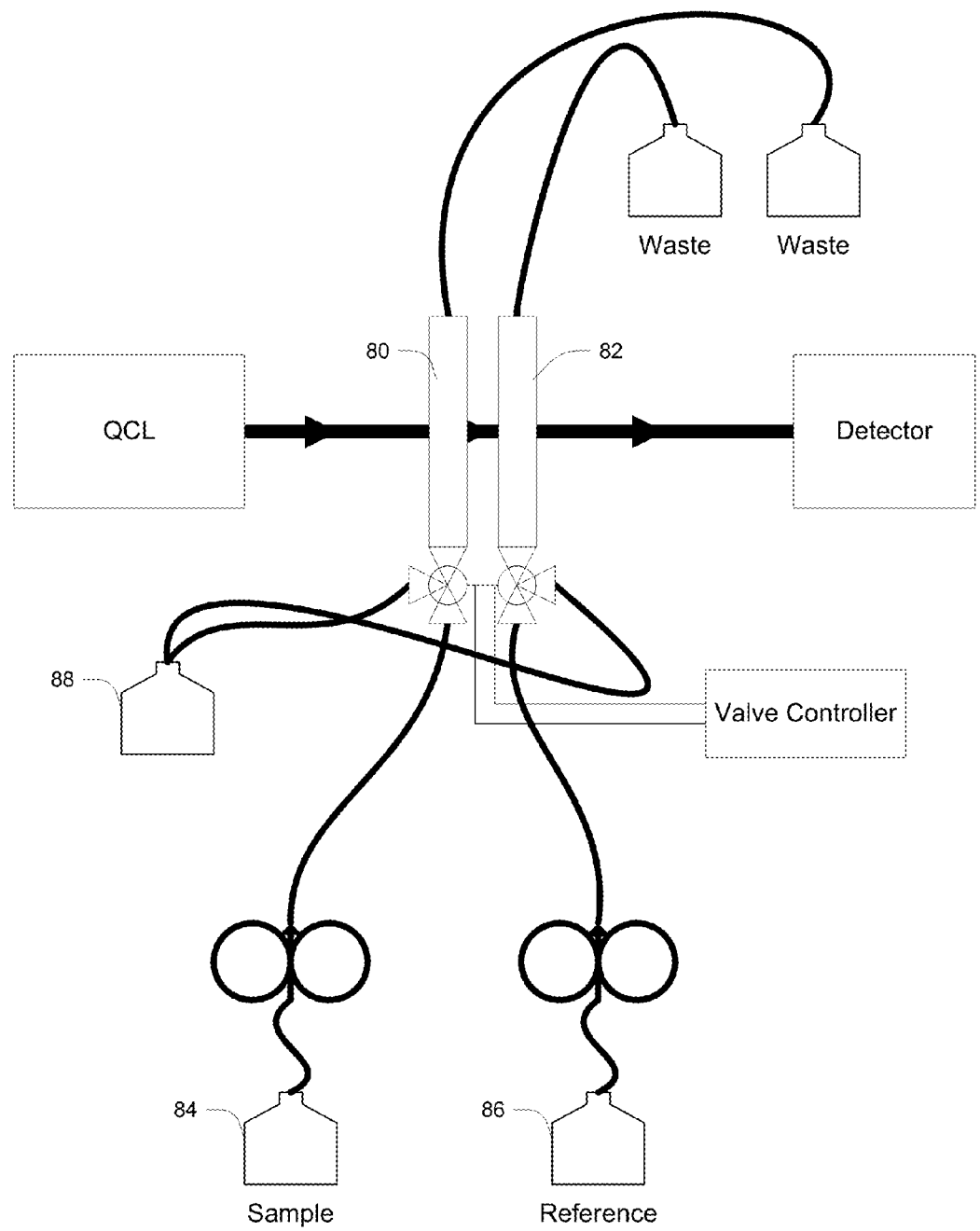

FIG. 6 shows a sample modulator using two flow cells 80, 82 with non-intermingling fluids. In this embodiment, the two cells 80, 82 are stacked back to back and the sample 84 and reference 86 solutions are each introduced into a respective one of the transmission cells 80, 82 interleaved with an optically transparent gas or liquid 88 (i.e. when measuring the reference 86 in the cell 82, the cell 80 contains a non-interfering or substantially non-absorbing fluid 88). Multiple cells may be advantageous for separating the outlet waste streams or avoiding cell contamination when multiple samples are measured. The cells 80, 82 may be physically separated or, to minimize reflections, they may share a sample cell wall. An array of more than two cells may be used for more than two liquids.

Figure 7:
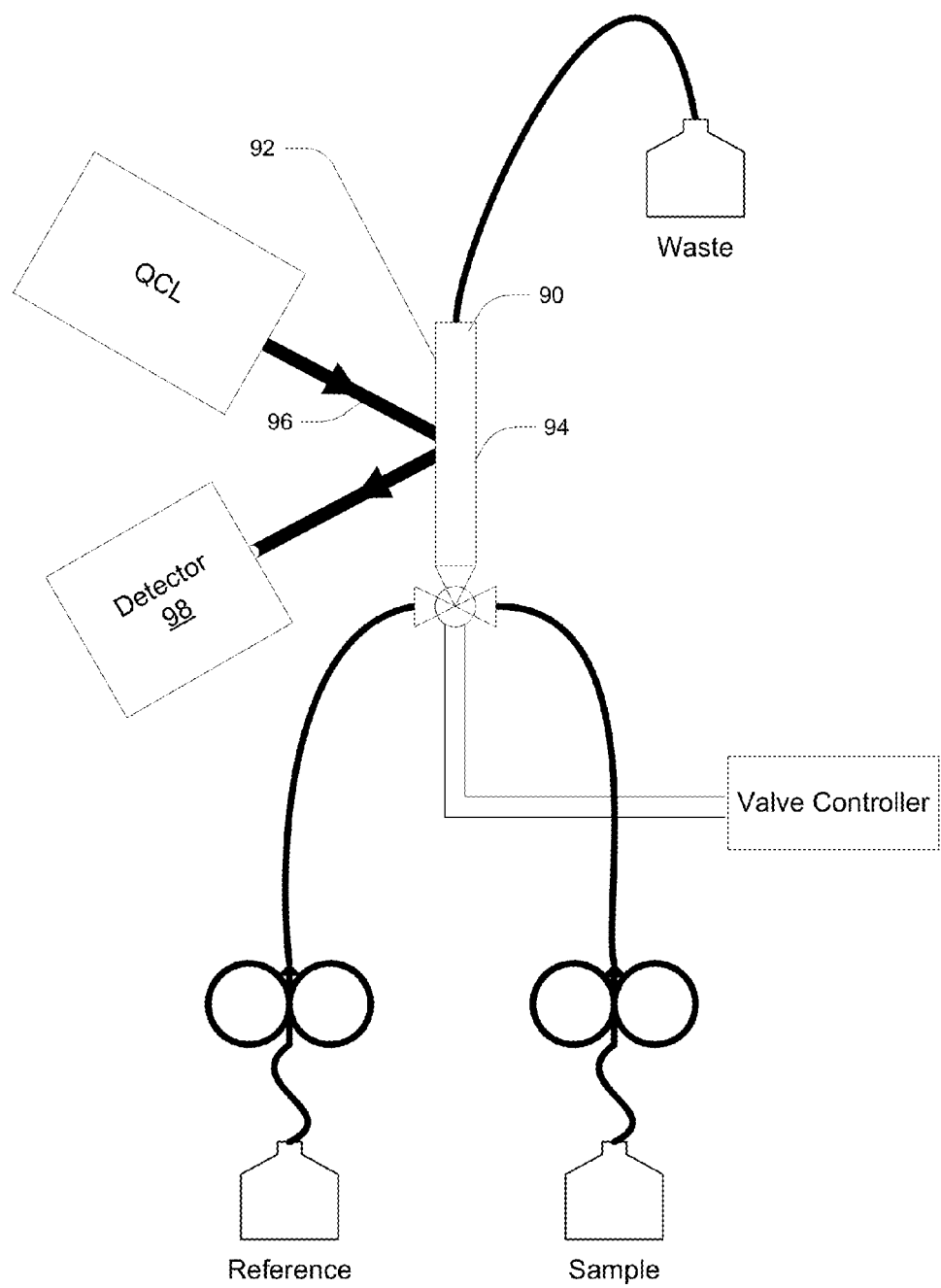

FIG. 7 shows an embodiment of the sample modulator using an IR transflectance sampling cell 90 which has an IR transparent window on a front side 92 and an IR reflecting material on the inside of a back side 94. The IR laser beam 96 passes through the transparent window 92, through the sample or reference solution at the interrogation region within the cell 90, then back through the sample or reference solution (after reflecting from back side 94) to an IR detector 98. This embodiment may be more compact than a transmission only cell system. The cell is effectively a two pass cell, requiring half (or less than half depending on the angle of incidence) the cell sample thickness to provide the same pathlength as a single pass transmission only cell. The reflection may be in the direction of stream flow as shown in FIG. 7, or it may be orthogonal to the direction of stream flow (e.g. across the width of the channel). When the reflection is in the direction of stream flow, a simultaneous measurement of both reference and sample may be taken when the boundary between the liquids crosses over the reflection region on the back surface of the optical cell, and the measurement result may be used in the calibration of the analyzer.

As a variant, not shown, the cell may have a back side surface which is partially reflective, providing the ability for simultaneous half path length measurement and full path length measurement and may use a pair of detectors. This may be advantageous to improve measurement dynamic range or improve compatibility with a broader range of sample analytes, references, or wavelengths of measurement.

Figure 8:
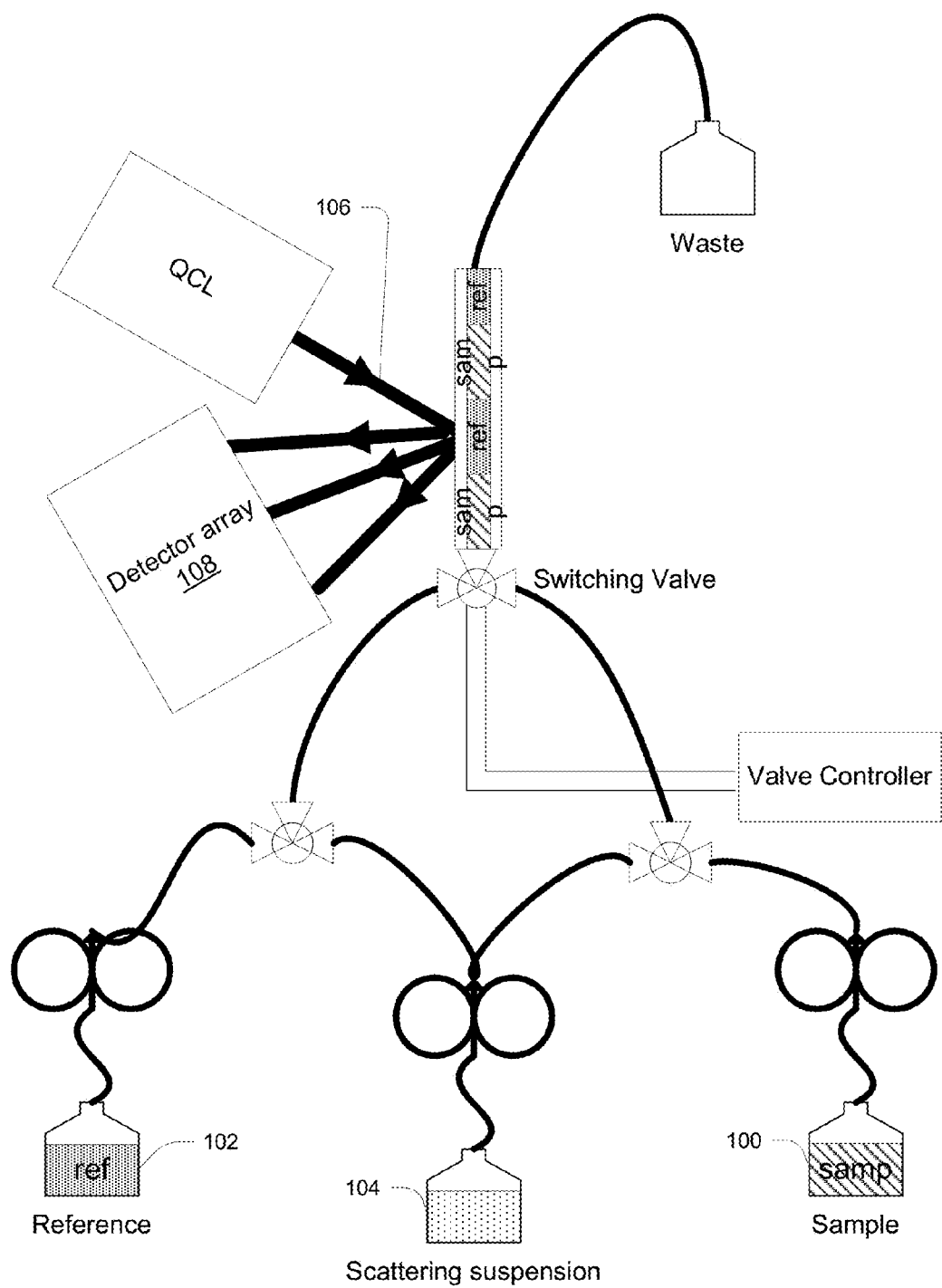

FIG. 8 shows an embodiment in which the sample 100 and reference 102 are mixed with a solution 104 of scattering or reflective particles in suspension of liquid. As the sample and reference pass through the beam 106, the light is scattered by the particles. The scattered light may be detected by a one- or two-dimensional detector array 108 as shown, or alternatively it may be refocused with a lens or mirror over some angle and focused on a single detector. The particle size or concentration may be varied to provide different average pathlengths in the fluid without a change in the geometric dimensions of the flow cell. This may be desired, for example, to provide enhanced dynamic range for analyte, reference or sample absorbance or other property. In another embodiment, the detector array 108 may be used to count particles or to measure the velocity of the stream flow by tracking the transit time of the particle in the cell.

Figure 9:
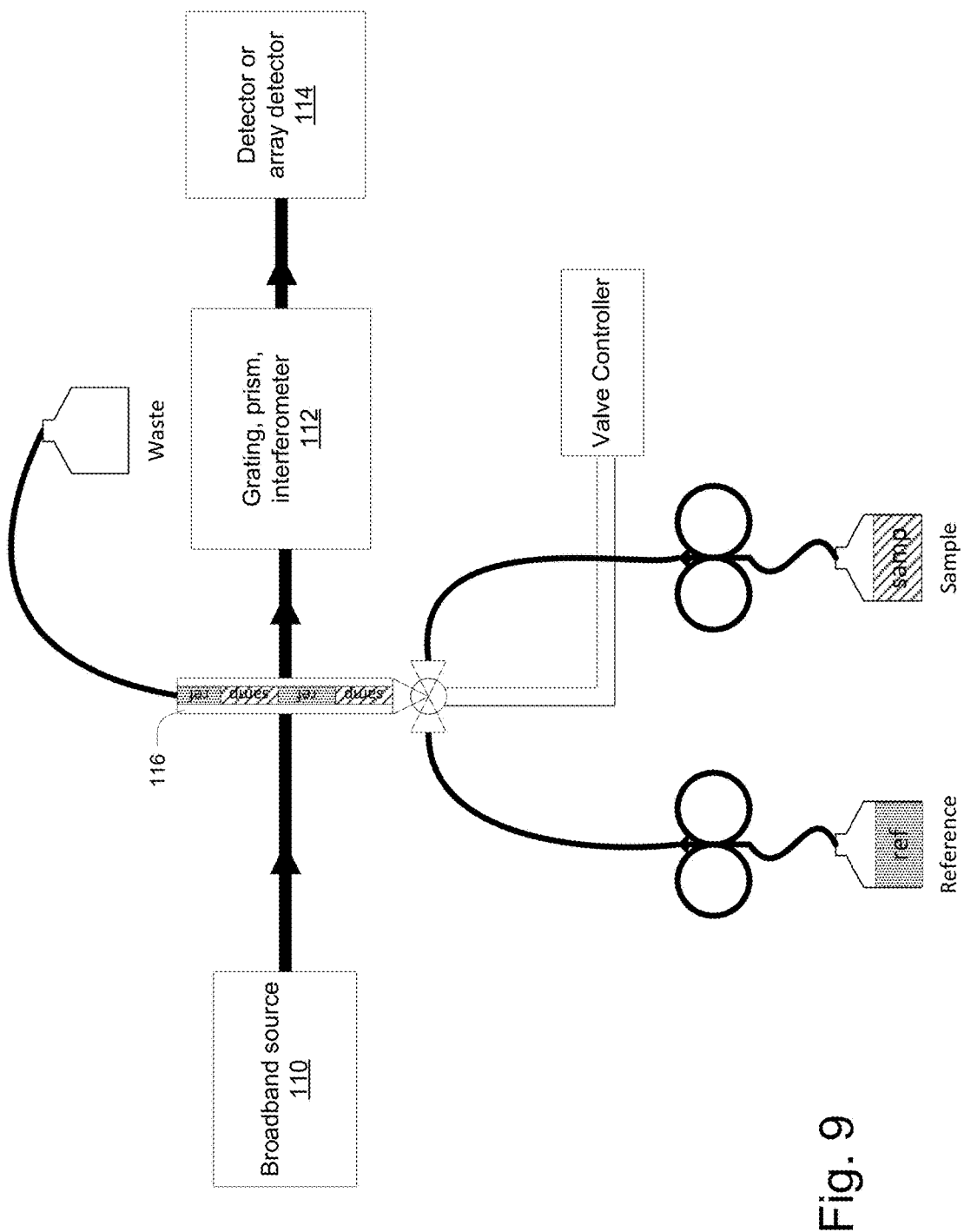

FIG. 9 shows an embodiment employing a broadband source 110 such as a thermal source, a lamp, FTIR, or a broad band Fabry-Perot laser, in contrast to a tunable source such as described with reference to FIG. 1. Light from the broadband source 110 is decoded by a spectrum analyzer 112 such as a prism or grating coupled with a single detector or detector array 114, an interferometer with a single detector, or other such spectral measurement components. If an interferometer or a single detector grating or prism is used, the decoding device can be placed in the optical path before the sample, i.e., between the source 110 and the cell 116. The decoding device may be placed before the sample to reduce the optical power in the cell 116 and thereby reduce any absorption by the fluids at other wavelengths.

Figure 10:
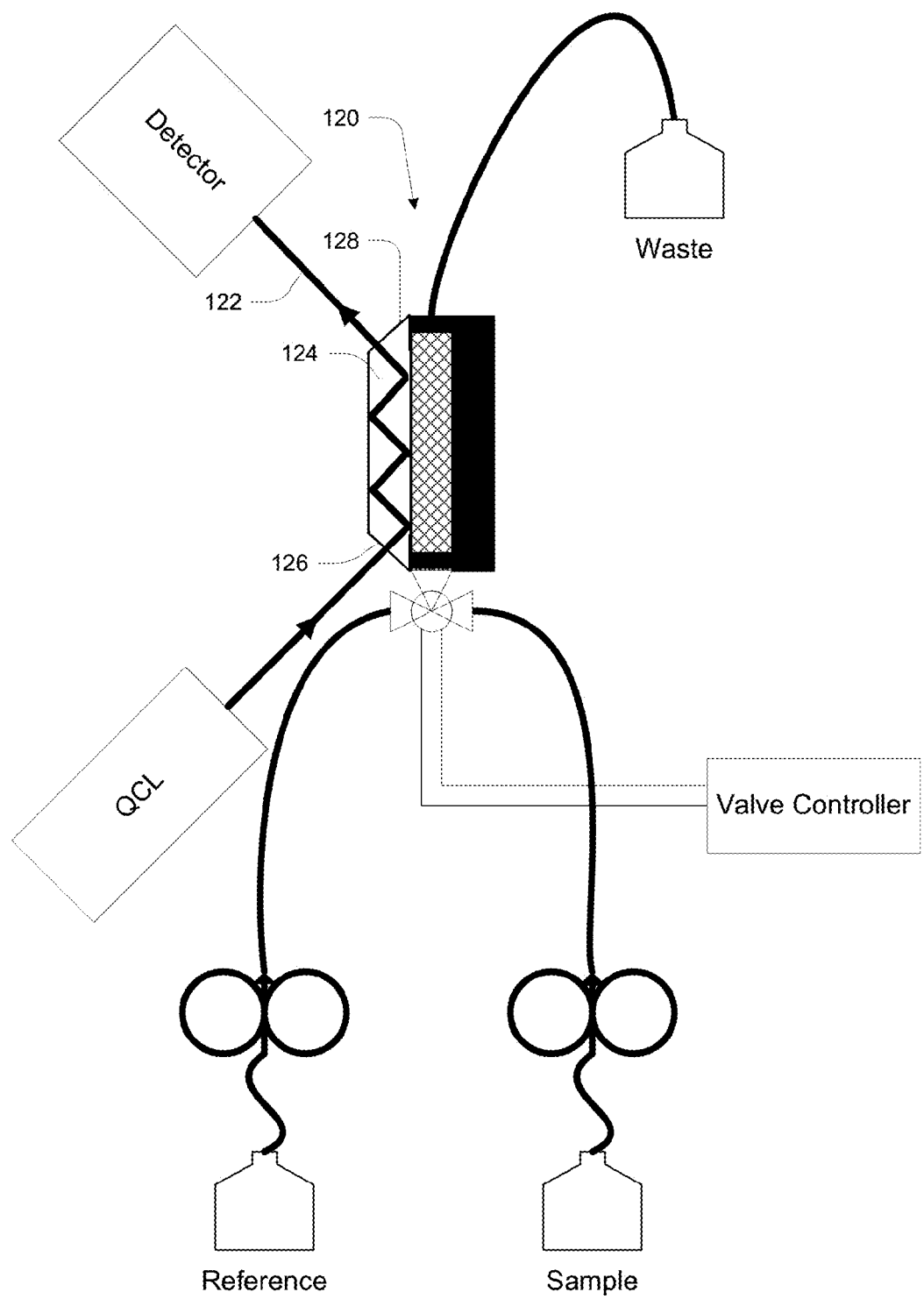

FIG. 10 shows an embodiment sample modulator using an ATR flow cell 120 similar to those used in Fourier Transform IR (FTIR) measurements. The IR beam 122 is introduced into an IR transmitting crystal 124 via one facet 126 at an angle greater than the critical angle relative to the back surface of the crystal 124. The light is reflected multiple times down the crystal 124 and out the opposite facet 128. The sample/reference solution flows past the back of the crystal 124, and evanescent IR waves interact with and are absorbed by the sample and reference. In this embodiment, the length of the sample/reference plug may exceed the length of the evanescent region of the ATR crystal 124 to achieve high signal strength. In another embodiment, the light source is the output beam of an FTIR interferometer and the detector is the FTIR infrared detector (e.g. the optical cell 120 is placed in the sample compartment of an FTIR analyzer along with any necessary focusing or collimation optical elements).

Analysis of Gases

Figure 11:
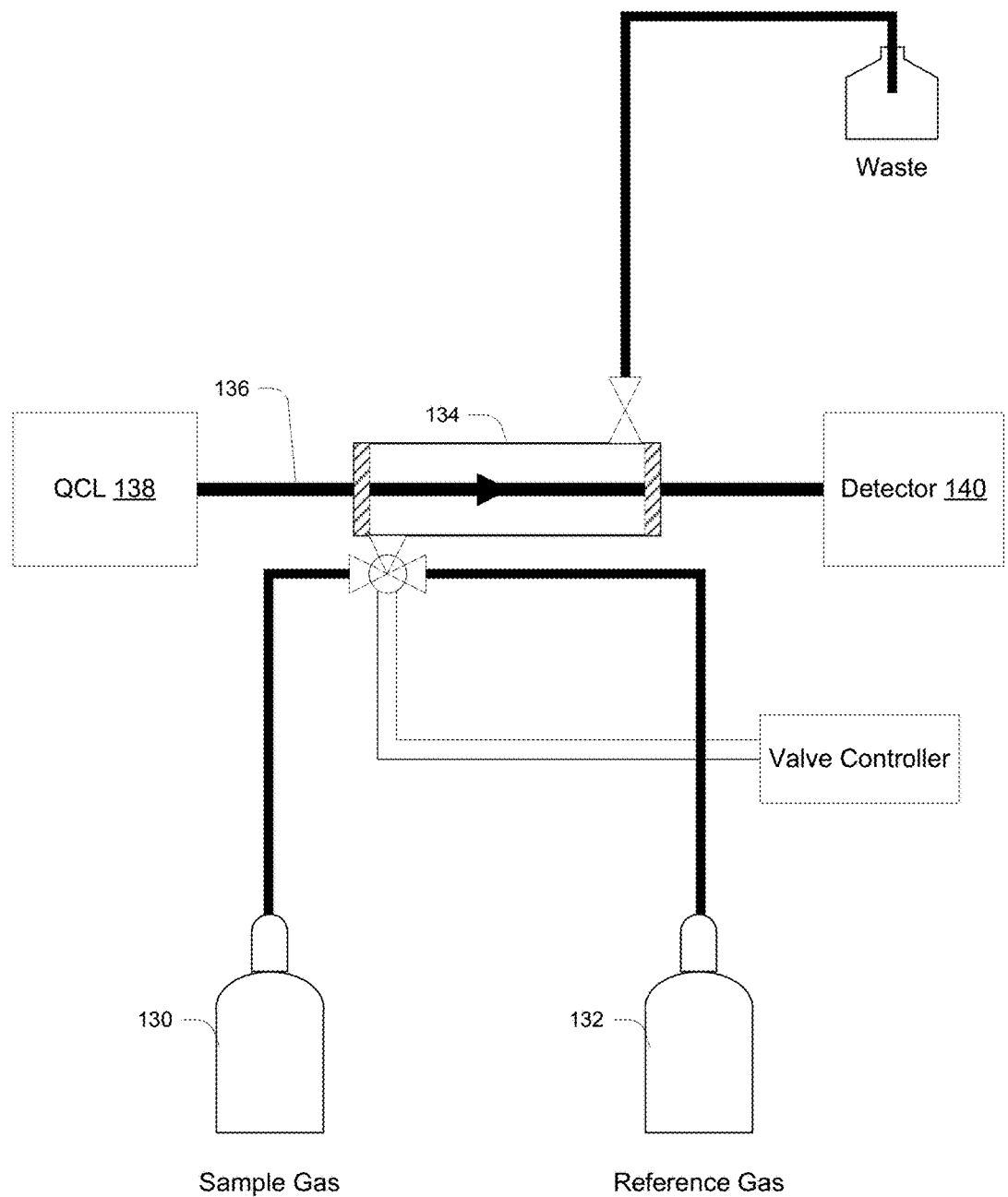

FIG. 11 shows an embodiment of a sample modulator using gases instead of liquids. Sample and reference gases 130, 132 are alternately introduced into a gas cell 134 to modulate an optical beam 136. The gas cell 134 may be a single pass, or any multiple pass gas cell. More than one sample and reference gas may be used.

It may be desirable to use a gas cell 134 of low volume with efficient flow characteristics as a sampling cell. One such cell could be a hollow fiber, if necessary coated with materials on the inner bore to insure high reflectance in the frequency range of interest. Other cell configurations are possible using more conventional cells such as a multi-pass White cell or a Herriot cell, or even an external cavity cell. Again, sample and reference gases 130, 132 are alternately introduced into the cell. The cell is completely or near completely flushed from the proceeding segment of reference or sample gas. The Mid-IR laser 138 is focused at one end of the hollow fiber or cell and appropriate collection optics (not present in the embodiment of FIG. 11) are used to collect the transmitted light from the other end of the fiber or cell and focused on the detector 140.

The sample and reference gases 130, 132 may be introduced into the cell by a switching valve, or by using various means of pressure control to alternately introduce the two gases.

The reference gas 132 may be a blank, such as a Mid-IR transparent gas (N2, He), or some other gas that does not interfere with the analyte of interest. The reference gas may also contain a representative matrix of the background of the sample. The representative matrix may even be the sample gas itself, with the analyte removed by some chemical, catalytic, filter, or other suitable method of analyte removal.

Again, one or more fixed frequency laser or tunable laser(s) are set to the desired frequency for each line of interest. As the sample and reference gases 130, 132 are passed through the cell 134, the laser absorption is modulated at the frequency of the sample/reference introduction. The difference in absorbance may be directly measured between the two streams, or a signal processing scheme or lock-in amplifier may be used to detect the signal and filter the noise.

Alternatively, for low molecular weight gases with narrow line rotational fine structure, the laser 138 may also be frequency modulated over the analyte line of interest to directly detect the gas species, and the reference is also scanned in the same way, which would allow for the correction of interfering species from the sample background. The laser wavelength modulation may include multiple cycles per analyte or reference sampling. In one embodiment, a reference and sample may each pass through the laser once every 100 msec and the laser may be wavelength modulated at a frequency of 20 Hz.

In another embodiment, the laser optical power may be amplitude modulated at constant wavelength, for example by using an optical chopper, optical modulator or by varying the laser electrical power. In another embodiment both the laser optical power and wavelength may be simultaneously modulated, for example by changing the drive current to a QCL chip.

Figure 12:
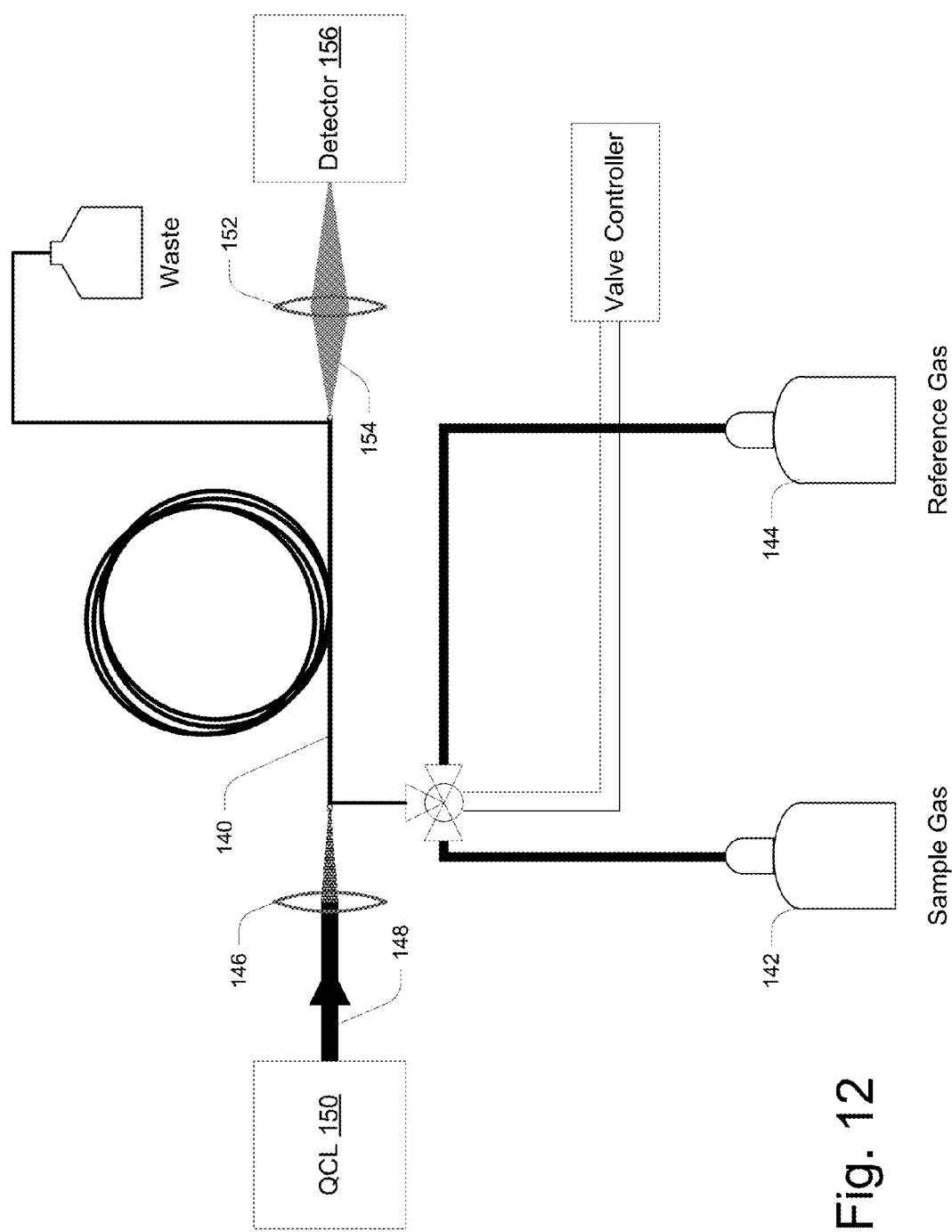

FIG. 12 shows an embodiment of a sample modulator using gases and a tube cell. The gas cell in this system comprises a hollow capillary tube 140 coated with a highly reflective coating on the inside. The sample and reference gases 142, 144 are alternately switched into the stream flowing through the capillary tube 140. Focusing optics 146 focus the laser beam 148 from laser 150 and direct the focused light into one end of the capillary tube 140. At the other end, collection optics 152 at the opposite end collect light 154 exiting the tube 140 and focus the light on the detector 156. The capillary tube 140 is flexible and can be conveniently coiled in a compact space.

Figure 13:
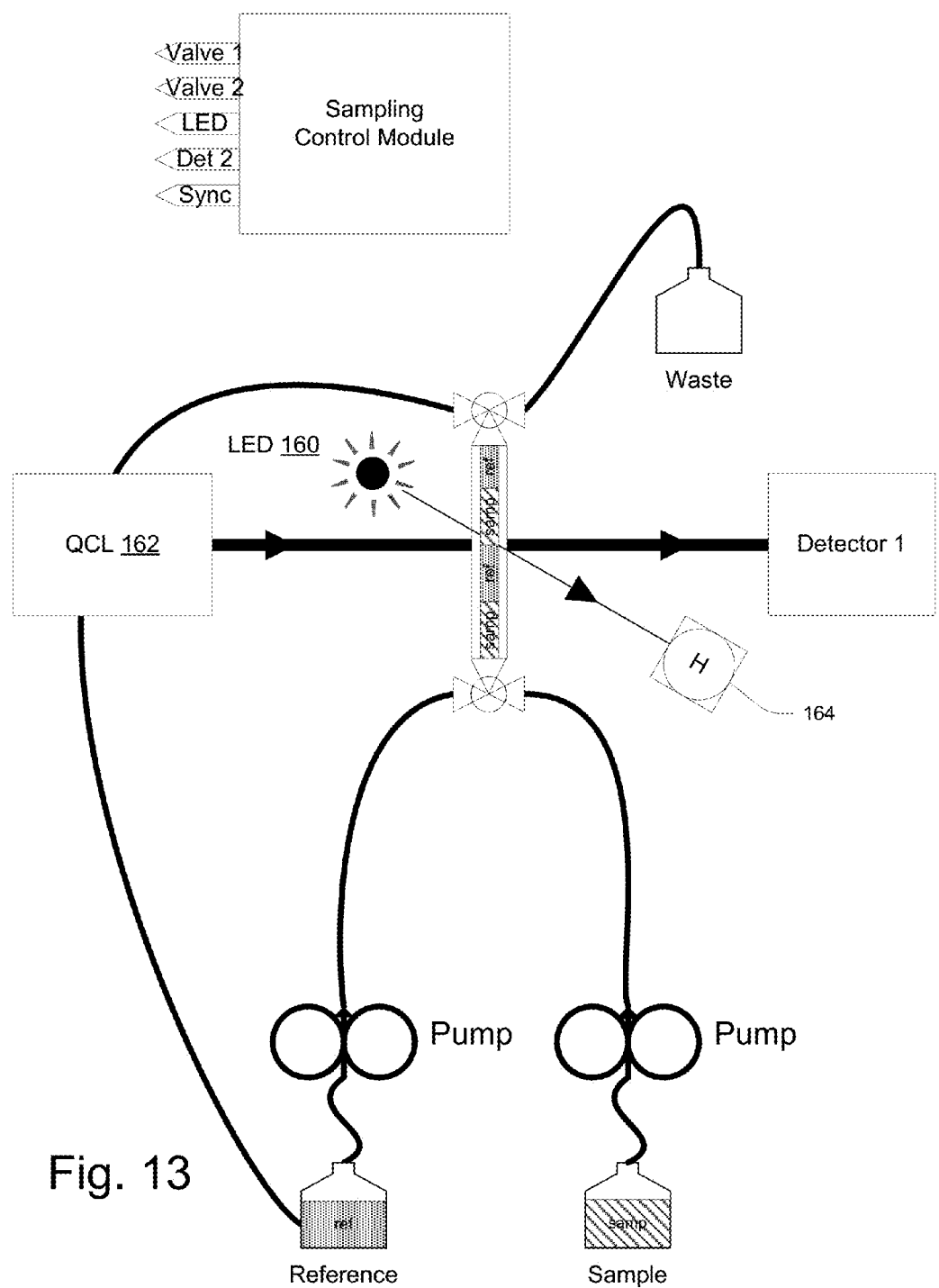

FIG. 13 shows an embodiment in which a second timing light source, such as a light emitting diode (LED) 160, is used to determine when the sample and reference materials are being measured by the QC laser 162. The timing light source 160 may be at a different optical wavelength than the QC laser 162. In one embodiment the timing light source 160 is designed for detection in the visible wavelengths. The timing light source wavelength is selected to provide a differential absorption measurement between the sample and reference at high signal to noise ratio. A dye or other material which is transparent at the measurement wavelengths of the QC laser 162 may be mixed into the reference or sample as an analyte to provide a high signal to noise timing measurement, thereby enabling the timing light source 160 and its detector 164 to determine when the reference is being measured by the IR laser 162. If a timing analyte is used in the reference, a different analyte, or the same analyte at a different concentration may be inserted into the sample to provide a measurement of the timing of both sample and reference. A non-optical transducer can be used as a timing reference, for example if the conductivity of the reference and signal are selected to be different. The conductivity measurement may be taken in a direction substantially perpendicular to the direction of fluid flow.

As discussed previously, the timing light source 160 may also be used to perform the transition timing region measurement and system feedback functions.

Figure 14:
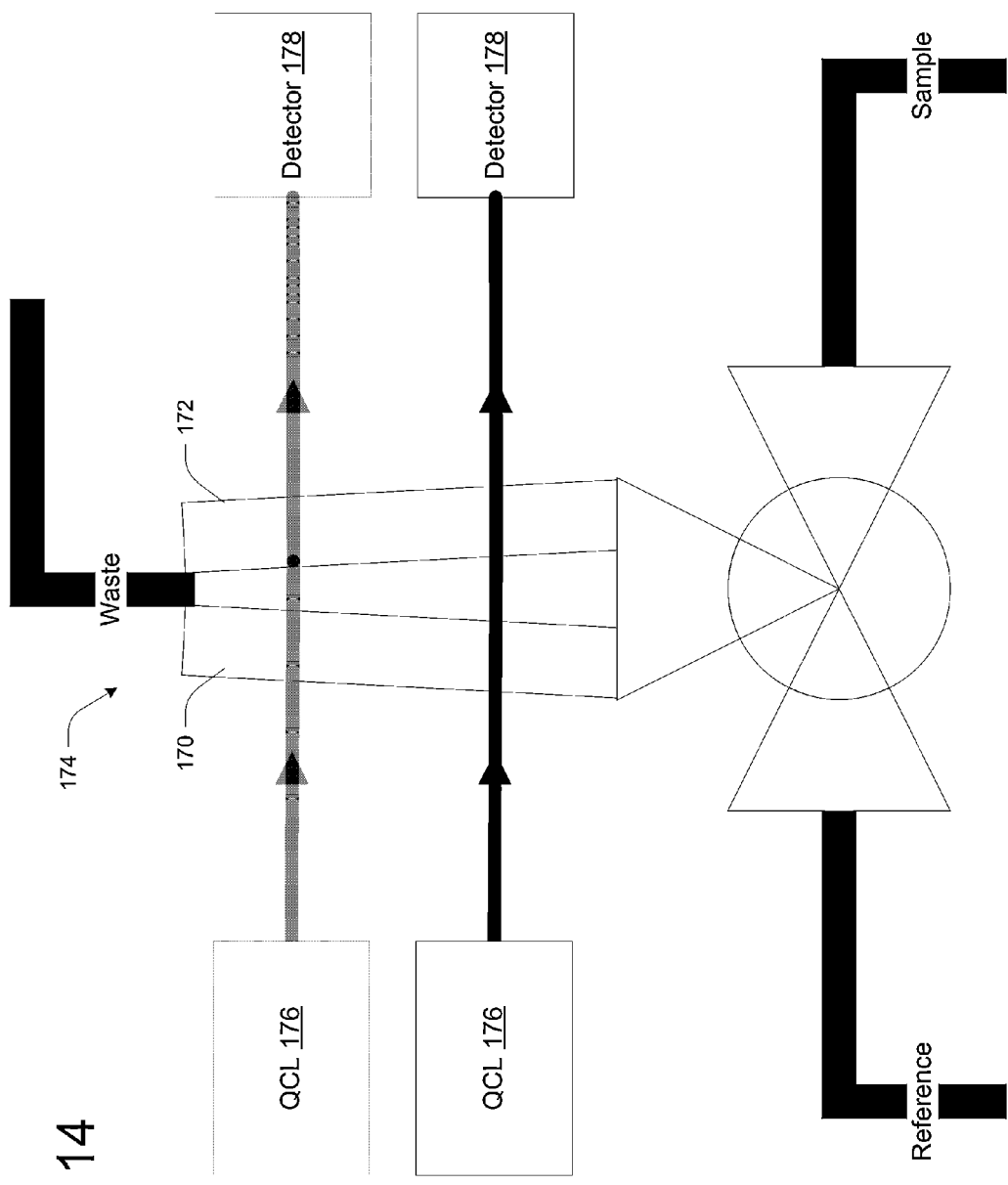

FIG. 14 shows an embodiment in which the cell windows 170, 172 are wedged relative to each other such that spatially positioning the cell 174 relative to the optical source beam or moving the beam along the height of the cell 174 creates a different pathlength for the sample/reference measurement. This allows optimizing the system for different pathlengths without changing sample cells. In addition, multiple sources 176 and multiple detectors 178 could be placed along the height of the cell to measure different analytes at different the pathlengths which are optimum for each analyte, or for measuring the same analyte at different concentrations extending the dynamic range of the system. An array of more than two lasers 176 and an array of more than two detectors 178 could be used to provide many pathlengths or to measure many analytes. The pathlength gradient may be continuous or in discrete steps, as for example, is commonly achieved using semiconductor processing methods.

Figure 15:
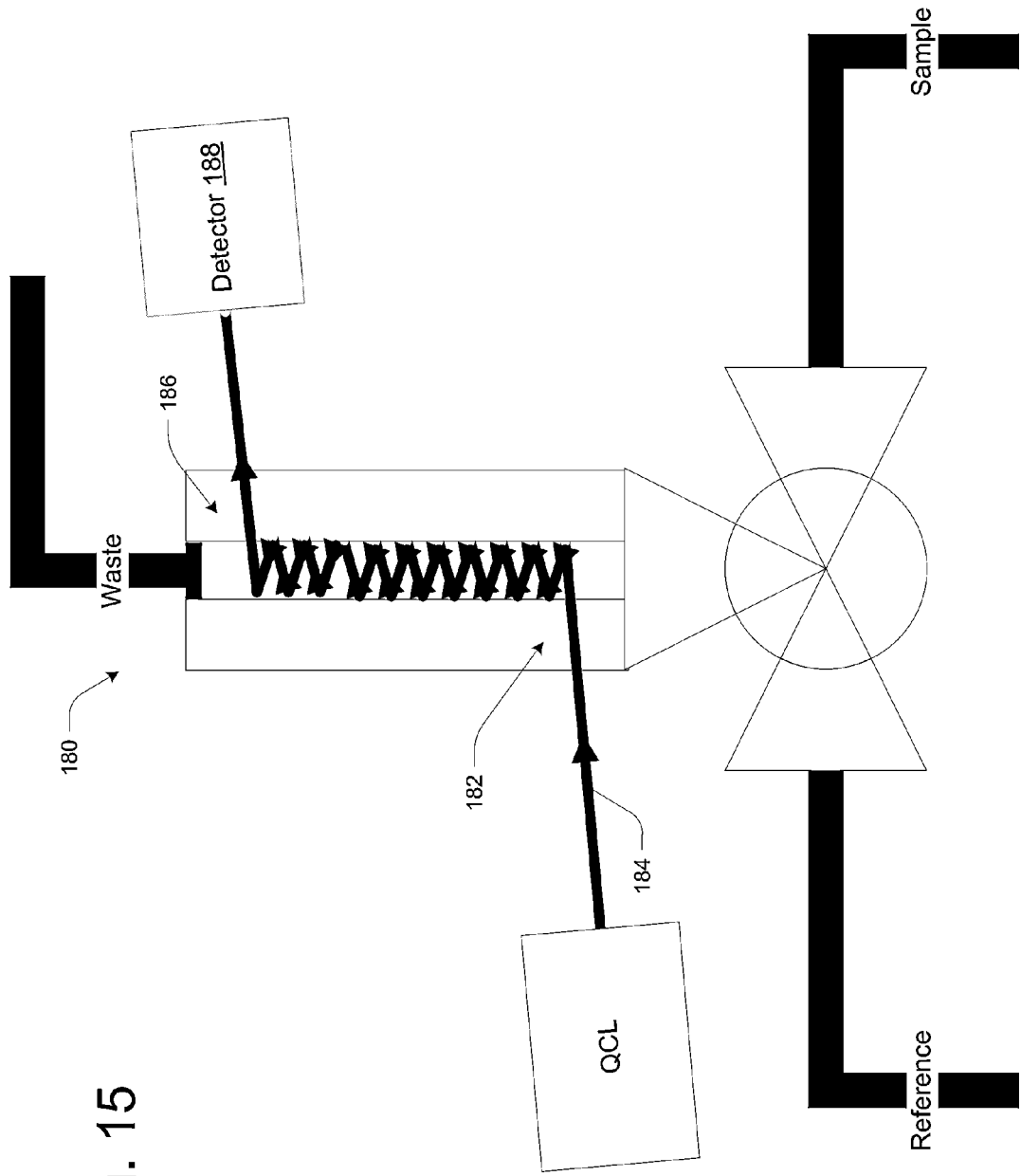

FIG. 15 shows an embodiment in which the inside surface of the cell 180 is coated with a reflective film. An uncoated section 182 provides a port for the laser beam 184 to enter the cell 180 at a desired angle. The beam 184 reflects back and forth along the cell 180 until encountering an uncoated exit port 186 that allows the beam 184 to exit the cell 180 and travel to the detector 188. The laser angle, cell height, and window spacing determine the number of reflections. This arrangement can allow for longer pathlengths to be used for weaker absorbing samples, as for example might be desired for water base liquids measured at visible or near infrared wavelengths. In another embodiment, the reflective surface and exit port 186 on one side of the cell 180 may be external to the cell and translatable in position to select which optical reflection exits through the port 186 for measurement by the detector 188. In this manner, an instrument may accommodate multiple path lengths in a single cell, with the ability to select the optimal pathlength as a function of liquid absorptivity, laser power, detector performance or other operating parameters. Similar to other embodiments, the reflections may be in the direction of stream flow or orthogonal to the direction of stream flow. In parallel to the stream flow, the length of each plug or packet of reference and sample may have the same geometric length in the channel which exceeds the length of the optical bounces. The length of the packets may be adjusted as a function of the number of selected optical bounces.

Figure 16:
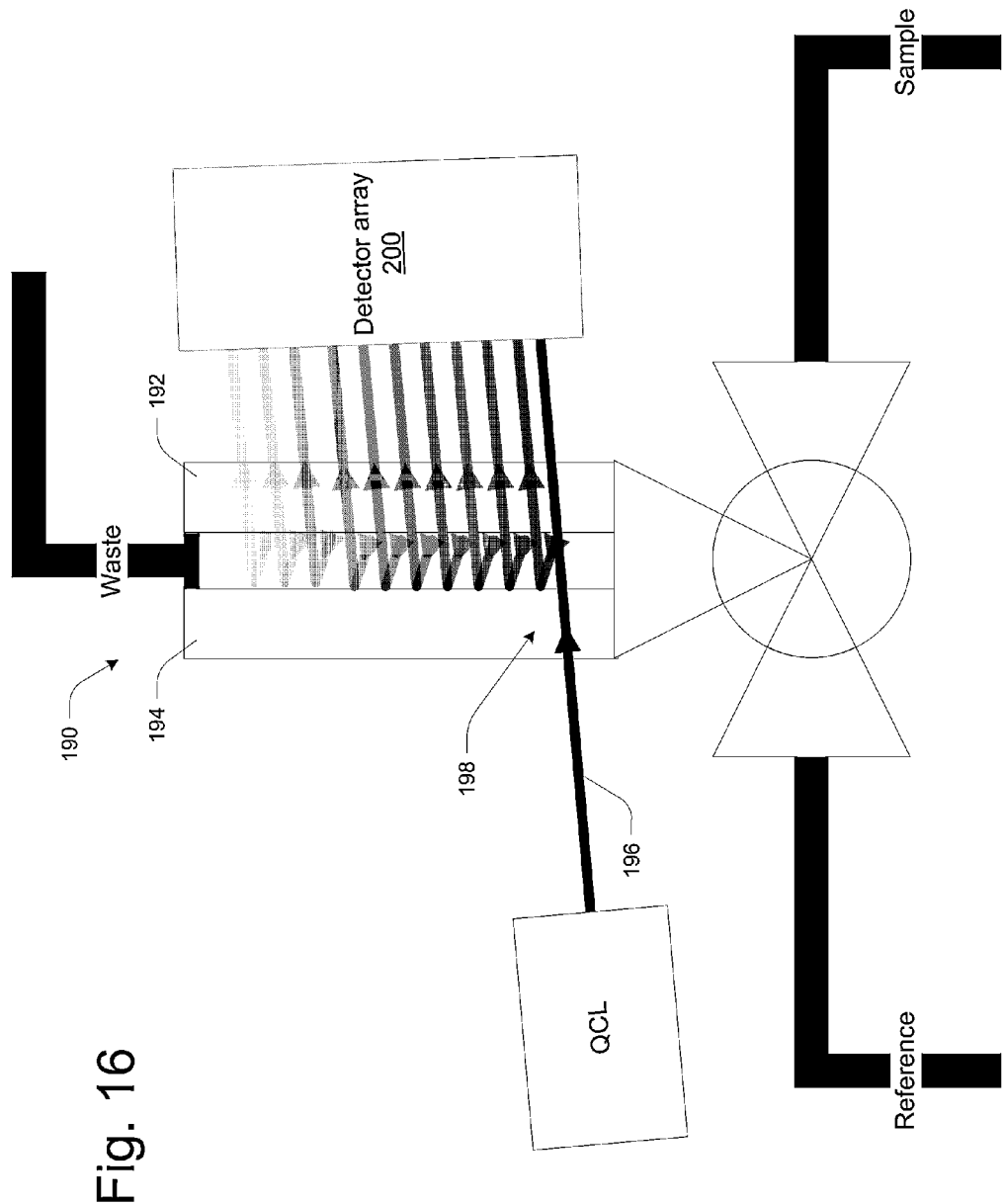

FIG. 16 shows an embodiment in which the inside surface of a cell 190 is coated with a semi-reflective film on the inside of the back window 192 and a reflective film on the inside of the front window 194. The beam 106 enters the cell 190 at an angle through an uncoated portion 198 of the window, and reflects back and forth along the cell 190, with some portion of the beam 196 transmitted through the semi-reflective coating at each reflection. The laser angle, window spacing, and cell height, determine the number of reflections. A detector array 200 is positioned to measure the transmitted rays of light. This allows for different pathlengths and power levels to be selected for optimizing the system power and pathlength for different sample conditions and types. Multiple lasers, or even laser arrays may be used to provide different wavelengths for different analytes.

Figure 17:
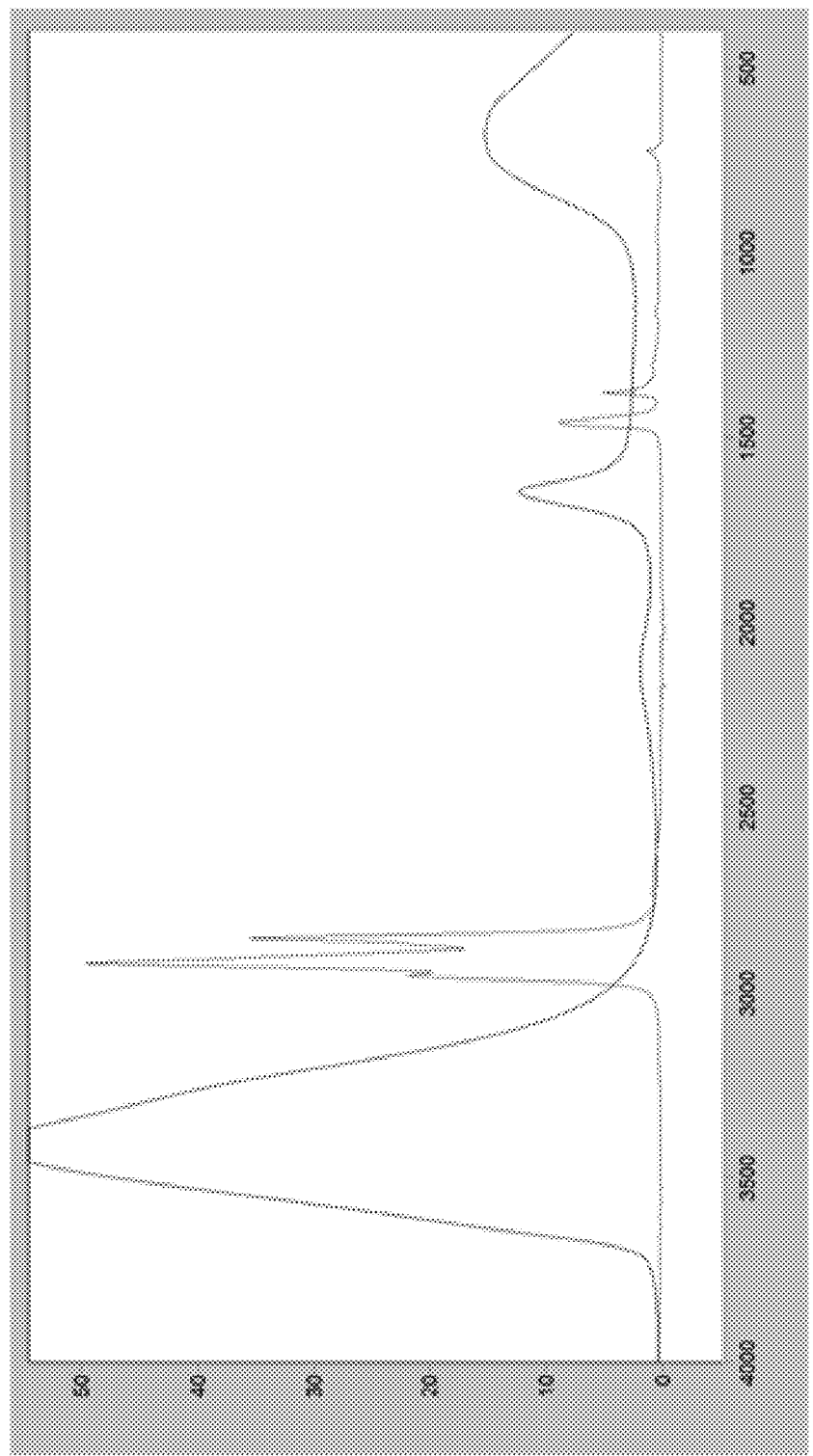
FIG. 17 is a plot showing a spectral optical absorption characteristic of water and oil.

FIG. 17 shows an example of spectral absorption of water and oil. With water as the solvent, and oil as the analyte of interest in the solution being passed through a flow cell, the laser power incident on the detector will be modulated by the absorption in the transmission cell. Since the analyte in the solution will displace the solvent in this example, the differential absorption between analyte and solvent will determine the differential signal at the detector as the sample (oil and water) and reference (water only) pass through the cell. A spectral region for detection of the analyte may be chosen where the differential solvent and analyte absorption is greatest, or around 2900 cm$^{-1}$ in the example of FIG. 17. The roles of solvent and analyte may be reversed depending on the requirements of the application (e.g. oil in water or water in oil).

Alternative embodiments may use spectral regions where the solvent absorption exceeds the analyte absorption. In one embodiment, a spectral region may be selected in which one or more analytes each have less absorption than the solvent. Thus the system will be one that effectively detects the absence of absorbing solvent in the cell pathlength due to its displacement by the lower absorbing analyte(s). This embodiment has the advantage of being able to detect the presence of one or more analytes at a single wavelength since at any analyte concentration of interest there is no additive combination of analyte total absorption where the differential absorption approaches zero.

Another embodiment can take advantage of displacement of the solvent by an analyte to detect a difference between the sample and reference. In this embodiment, the reference channel contains a "standard" solution with one or more analytes, which would be compared to the "sample" solution. Any difference in absorption of the two channels may indicate either a difference in concentration of one or more analytes between the channels, or the presence of an impurity. This provides a quality control check in the manufacture of any liquid product, or could provide a quality control check of the purity of a product. Various combinations of desired analytes, undesired analytes (i.e. contaminants) and wavelengths can thus be employed to measure sample liquid properties.

Thus one embodiment may include one or more sampling cells that (1) detect the presence of one or more analytes at a spectral wavelength where the one or more analytes have combined absorption less than the solvent, and then (2) speciate between the analytes and determine their concentration in the solution at one or more other spectral wavelengths. One advantage of such a system is that it may more rapidly detect at a single wavelength the total concentration of multiple analytes or more readily detect the concentration of a single analyte in the absence of other analytes or interfering substances. In one embodiment, the sample is measured at a single wavelength and if the analyte absorption exceeds a threshold, then the sample is held longer and the tunable laser is used to measure absorption at additional wavelengths in order to speciate the one or more analytes. It should be recognized that alternative combinations of wavelengths, solvent absorption and analyte absorption may be chosen for a particular application. In another embodiment, all of the analytes of interest have absorption at the selected wavelength that exceeds the solvent absorption and thus once again there is no combination of analyte concentrations (other than none) where the combined analyte absorption equals the solvent absorption.

In the above-described embodiments, a pump is used to provide the solution to the flow cell. In other embodiments, the solution may be drawn from a pressurized source and a valve is used to regulate the pressure and velocity of the solution in the transmission cell. In another embodiment, a flexible membrane between a pressurized solution source and a second solution (e.g. between sample and reference) is used to pressurize the second solution and thereby eliminate a second pump. In another embodiment, no pressure increasing pumps are used on the inlet side of the cell but a pressure reducing pump is used on the outlet side to create a desired pressure differential between cell inlet and outlet.

Figure 18:
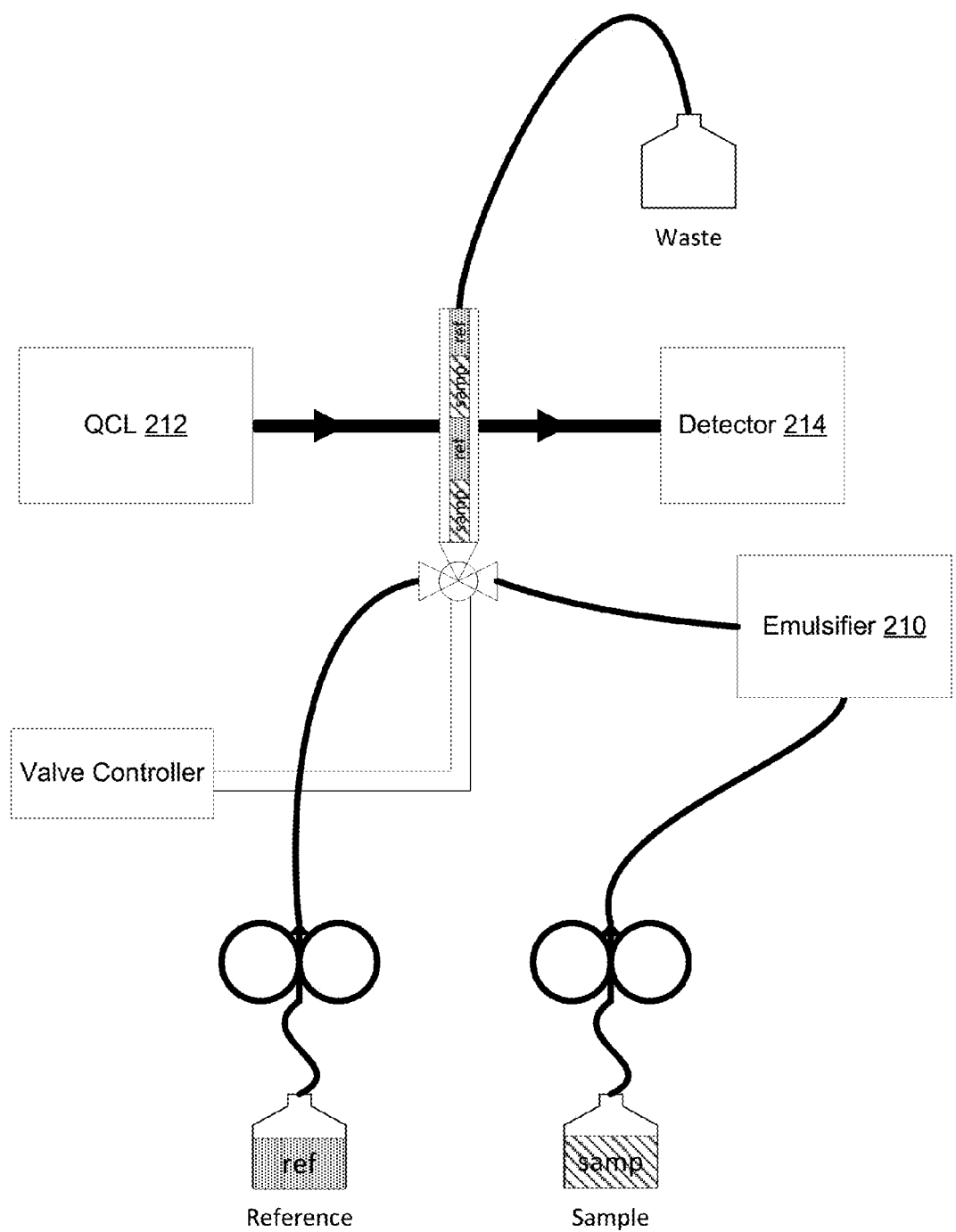
FIG. 18 is a schematic diagram of a fluid analyzer.

The analyte and solvent may be immiscible liquids. It may be advantageous to ensure formation of an emulsion of the analyte in the solvent through means such as homogenization, shaking, addition of an emulsifier, or, by creating turbulent flow. An example using an emulsifier 210 is shown in FIG. 18. The emulsion may have a targeted level of statistical distribution or particle size. The targeted particle size may be determined by the wavelength of laser light relative to the particle size. The target particle size may be at least five times larger or smaller than the wavelength of the laser light. Then the system may include a light source 212 and detector 214 for measuring the particle size or particle density. Such a particle measurement system may be used to provide feedback into the means for emulsification. Such a feedback system may also be used to change the flow rates in the cell or the absorption measurement time or both.

Figure 19:
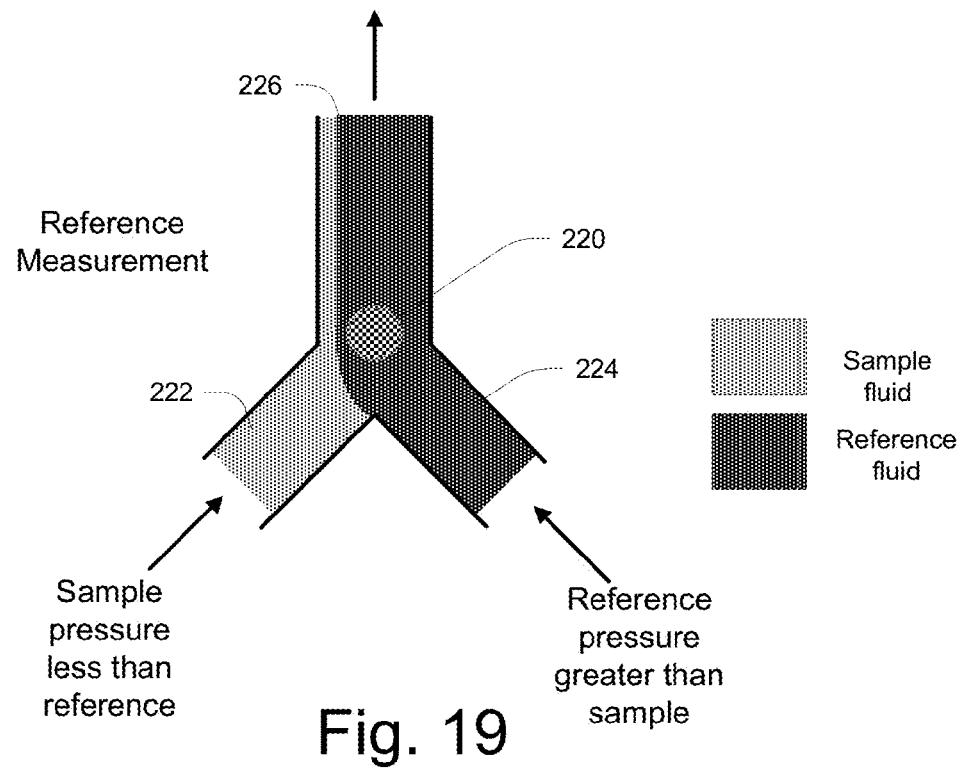
FIGS. 19-22 are schematic diagrams of a fluid merging location in a flow cell.
Figure 20:
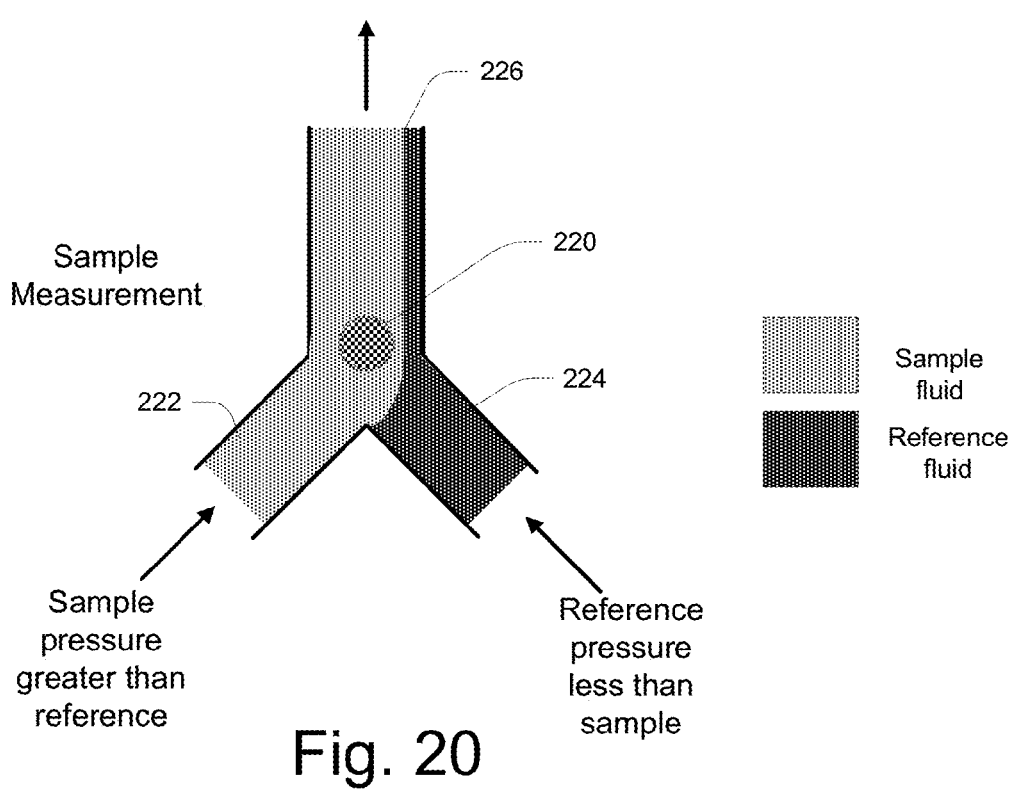

FIGS. 19 and 20 illustrate an embodiment in which a sampling beam interrogation region 220 (i.e. the region of the flow cell channel that transmits the laser beam and is the absorption detection region) is placed at or near the convergence of the sample and reference streams 222, 224 in a fluid channel 228 where they are separated by a fluid boundary 226. In these Figures the laser beam is traveling orthogonal to the page. By varying the relative pressure of the two streams 222, 224, the widths of the streams 222, 224 in the fluid channel 228 can be varied such that the laser beam alternatively passes through one stream 224 (FIG. 19) and then the other 222 (FIG. 20). By time varying the pressure differential between the two streams 222, 224, the frequency or rate of measurement of the sample and reference may be varied, as can the transition time when regions of both the reference 224 and sample 22 are within the interrogation region 220. As in the example shown in FIGS. 19 and 20, the size of the interrogation region 220, which is substantially the same as the laser beam diameter, may be less than the width of the individual streams 222, 224, enabling a discrete sampling of each stream 222, 224. Alternatively, the laser beam diameter may exceed the width of the individual streams 222, 224, and multiple detectors may be used to spatially sample across the transition region or across the sample, reference and transition region streams.

As is known in microfluidics, the velocity of the stream in cell channels decreases in relation to increasing proximity to the sides or walls of the cell channel. Thus in an embodiment of the type shown in FIGS. 19 and 20, there will be a region proximate to the cell optical windows where reference or sample streams do not move back and forth with pressure. The presence of such a stationary region reduces the measured absorption difference between reference and sample. A non-circular light beam may be employed, where the beam orientation relative to the cell channel may be controlled to increase the measured absorption difference (or measurement signal to noise) relative to that achieved with a circular light beam of nominally the same optical power. For example, the interrogation may be longer in the direction of fluid than in the direction orthogonal to fluid flow.

The stationary region may be reduced over time as, in one example, the sample liquid or analyte diffuses into the reference liquid. A measurement of the optical signal over time thus can provide for the measurement of the rate of diffusion of one liquid or compound into another liquid. The frequency of sample and reference measurements may be controlled to enable the measuring of the rate of diffusion. The aspect ratio of interrogation region diameter over optical pathlength through the channel may be greater than one in order to increase the amount of "stationary region" liquid in the beam path and thus improve measurement accuracy.

Figure 21:
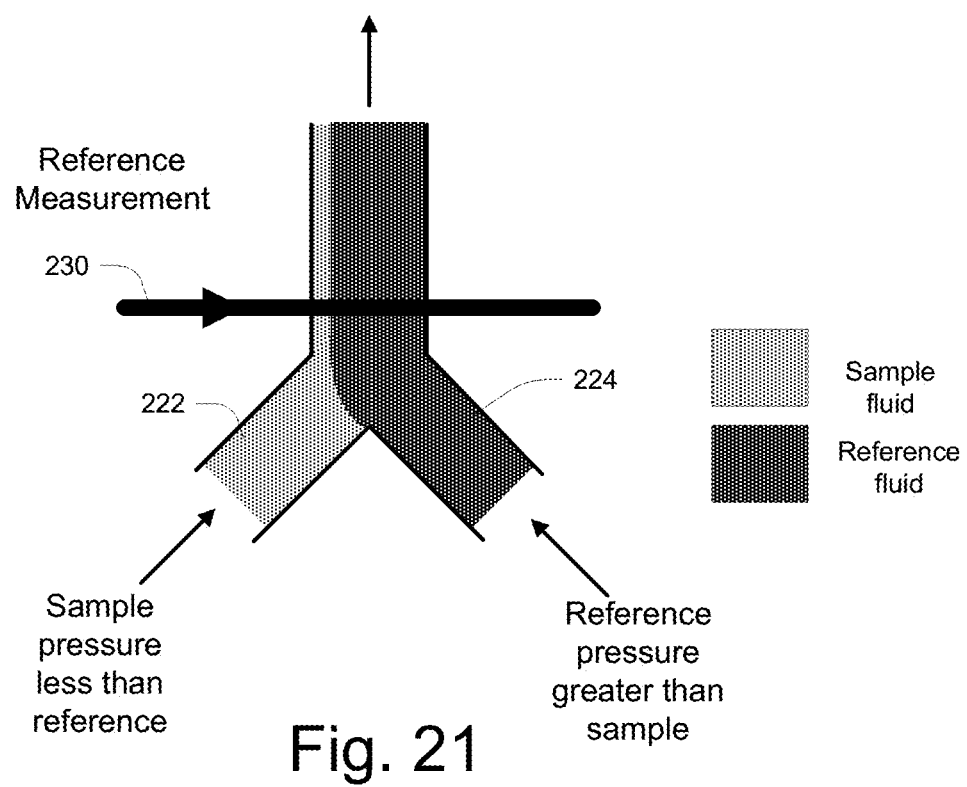
Figure 22:
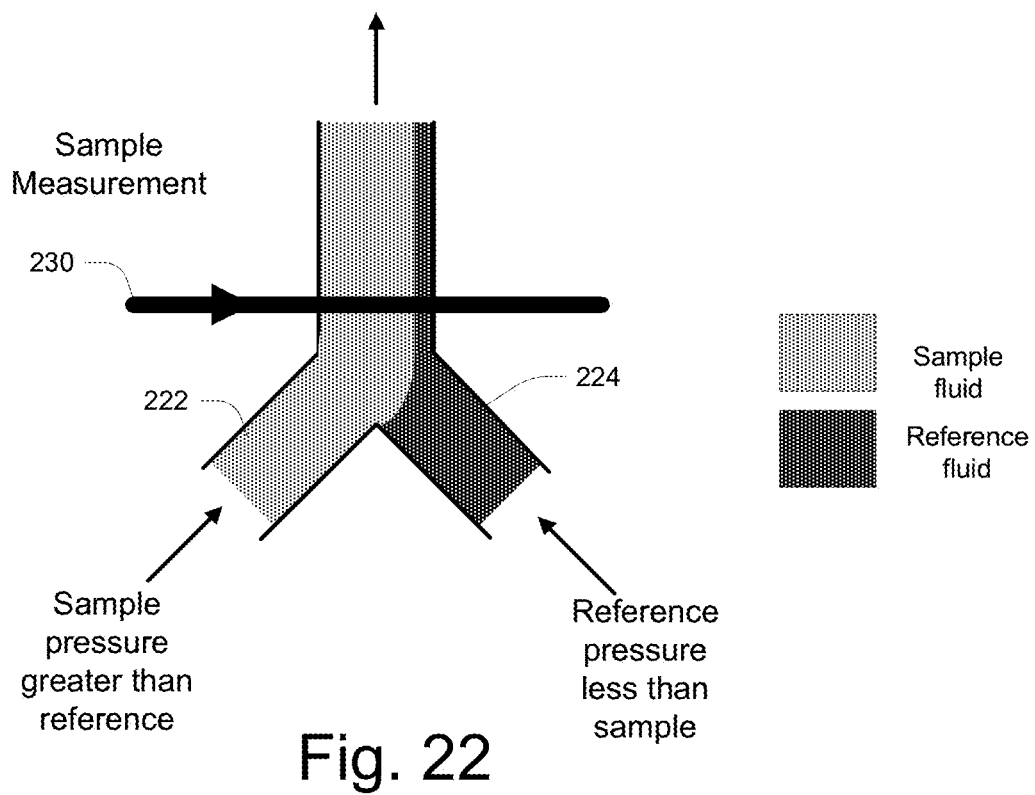

FIGS. 21-22 illustrate a variation of the fluid modulation scheme of FIGS. 19-20 in which the optical beam 230 is rotated by 90 degrees with respect to the streams and probes both the sample and reference streams 222, 224 simultaneously. As the pressure is varied in the two streams, the pathlengths of sample and reference fluid that are traversed by the beam 230 is varied accordingly. In this embodiment, the beam 230 does not impinge on the stationary region. The pressure may be modulated continuously, for example sinusoidally, in order to induce a similar modulation of the effective pathlength in the sample and reference fluids.

While many of the embodiments have been described using an optical laser, a FTIR may also be used as an optical source to realize improved measurement performance, where interferometer and instrument timing may be synchronized to the timing of the motion of the sample and reference within the cell. The interferometer may use a moving mirror or other means of modulation as known in the art. In one embodiment, the motion of the scanning mirror may be synchronous with the fluid modulation signal, and a controller may use a ratio of respective detector output signal samples for the analyte (e.g. sample) and reference fluids to determine a measurement value of the fluids as a function of optical wavelength of the interferometer. Thus measurement with an FTIR may include the following steps:

1) Positioning of a reference liquid (static or flowing) in the FTIR illuminated interrogation region (e.g. within the sample compartment of the FTIR, with collimation, focusing or optical apertures for delivering the optical output of the FTIR interferometer to the interrogation region)
2) Performing one or more interferometric scans of the reference
3) Positioning of a sample liquid (static or flowing) in the FTIR illuminated interrogation region
4) Performing one or more interferometric scans of the sample
5) Calculating a transmission as function of optical wavelength through the interrogation region from the ratio of reference and sample interferometric scans
6) (Optionally) Generating a synchronization signal upon positioning of the reference liquid, the sample liquid or the completion of the one or more interferometric scans.

In another embodiment, the measurement with an FTIR may include the following steps:

1) Continuous modulation of reference and sample liquids to present reference and sample liquids to a FTIR illuminated interrogation region with a modulation frequency of X
2) Generating a synchronization signal indicative of the timing of the continuous modulation
3) Continuous scanning of the FTIR interferometer at a frequency Y to continuously present frequency modulated light to the interrogation region
4) Where the ratio of X to Y is an even integral number such that there are an even fixed number of interferometric scans for every modulation cycle of the liquids
5) Timing circuitry effect to synchronize the liquid and interferometric scans
6) Signal processing circuitry effective to calculate the relative transmission through the optical cell as a function of sample and reference absorption and as a function of wavelength, wherein the transmission is calculated from one or more interferometric scans of reference and sample
7) Coadding of the relative transmission using multiple modulations of the liquids where the coadded samples have a fixed relationship to the synchronization signal (e.g. the coadded transmissions are located at the same point in time of the liquid modulations)

In various embodiments it may be advantageous to modulate the amplitude or wavelength of the laser signal synchronously with the modulation of the sample stream position on which the laser signal is incident. For example, the laser signal may be turned off when the transition region is transiting the cell window such that system power is conserved and absorption measurements are only taken for the unmixed reference and sample streams. Laser light may be collimated using one or more collimating lenses before the light is passed through the sample cell. In another embodiment, no collimating lens is used and a collecting lens is used on the detector side of the cell to collect the transmitted light and steer it to the detector. In another embodiment, neither collimating nor collecting optics is used and the laser and detector are aligned in close proximity to the sampling cell windows in order to maximize the optical throughput of the system. In a variation on this embodiment, the sidewalls of the sample cell are metalized or otherwise optically coated to guide the light from the laser to the detector. In another embodiment, a Fresnel lens is built into or attached to the surface of the microfluidic device in order to improve the optical throughput from laser to detector. In another embodiment the laser is oriented such that the shorter axis of an asymmetrically diverging laser output is aligned with the direction of the stream flow. In another embodiment the laser or detector are directly attached to the transmission cell using an index matching material.

Figure 23:
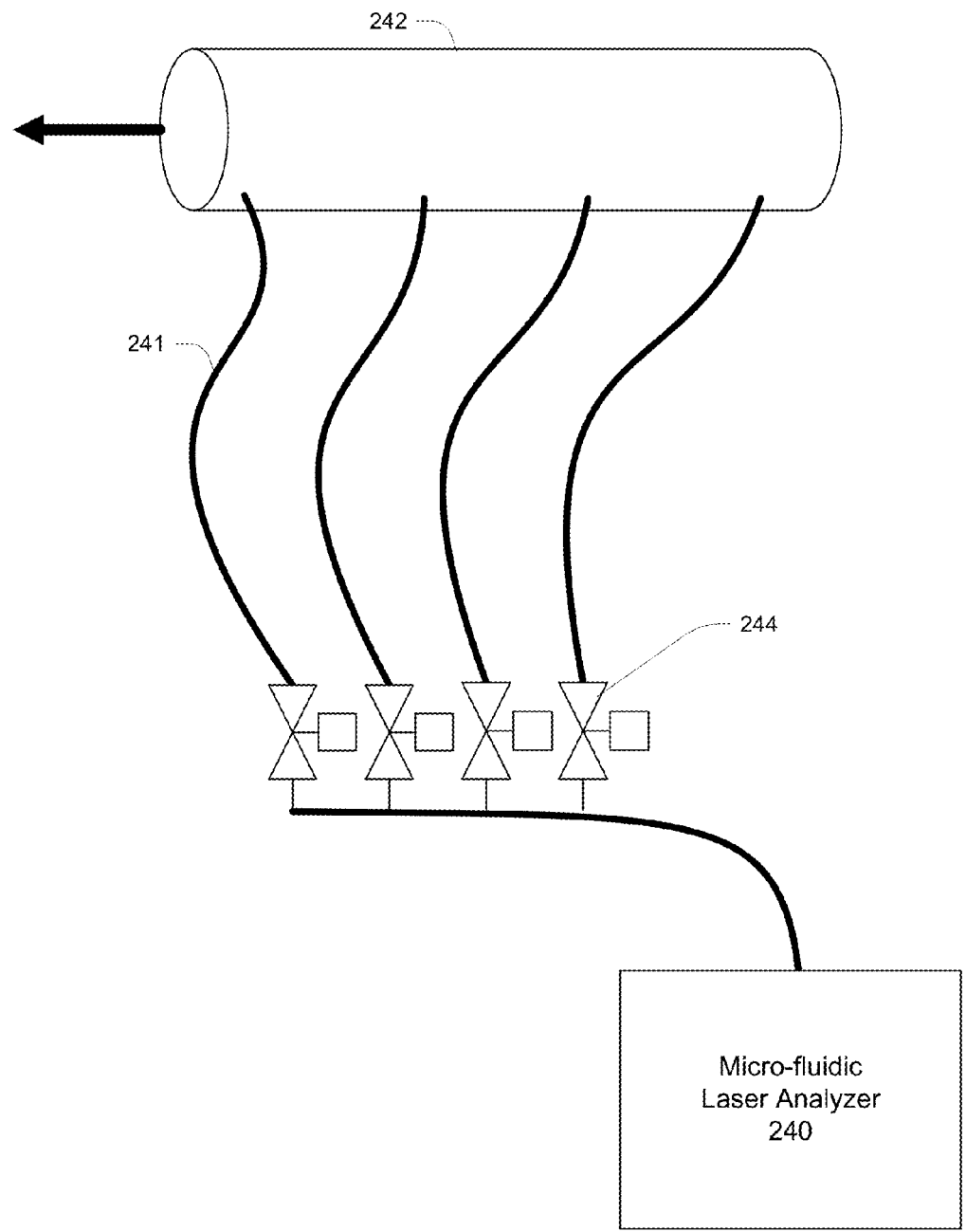
FIG. 23 is a schematic diagram of a fluid analyzer.

FIG. 23 shows an embodiment in which the a sequence of samples are provided by sampling tubes 241 to a microfluidic laser-based analyzer 240, which may be realized according to one of the above-described embodiments. In particular, the sequence is obtained by sampling a stream 242 at multiple sampling points, which may be spatially dispersed in such a manner as to ensure that the collected samples are representative of the liquid within the object being sampled (e.g. water in a pipe or container). In this manner, the small volume of the microfluidic transmission cell can efficiently sample the liquid in a larger object. Samples are sequenced by sequential operation of sampling valves 244. The spatial positioning of the sampling points may be determined by the time variant nature of the liquid in the sampled object (e.g. flowing water in a pipeline) and the timing of the absorption measurement. For example, as shown in FIG. 23, sampling points may be dispersed in the direction of water flow such that the samples are measured in the cell as if they were collected simultaneously in a plane that is perpendicular to the direction of water flow. In another embodiment, each of the sample points may feed separate sampling cells each with their own laser and detector, or sharing the same laser using beam splitting techniques well known to experts in the art. In another embodiment, each of the samples are mixed to create an "average" sample prior to being measured by absorption. In another embodiment, samples collected by each of the sampling points are sequentially passed under the measurement window permitting the separate absorption measurement of each sampling point. The separate absorption points may then be averaged in signal processing electronics. In another embodiment, the multiple samples may be combined in a high stream velocity channel that is then sampled by the flow cell at a lower stream velocity. In another embodiment, the reference fluid may be extracted from sampling stream 242 at a different location than the samples 241 and thus provide for a measurement of the change over time in flowing stream.

Sample cell or feed lines or both can be temperature controlled to bring the solutions to well controlled, constant temperature before being measured. Accurate temperature control alleviates temperature dependent spectral changes (very common in polar solvents such as water, very problematic in milk measurements)

The length and relative spatial positioning of the microfluidic stream channels may be determined in part to ensure the desired temperature uniformity of the solutions being tested. The microfluidic cell may include a heater (or be mounted on a thermoelectric cooler) and temperature sensor to control the temperature of the cell and thereby the solutions flowing in the cell. The temperature sensor may be used to provide a reading of the stream temperature for use in determining fluid characteristics (e.g. absorption) by enabling an adjustment in the calculated characteristic due to temperature.

The absorption of light by many liquids has a dependence on temperature. In one embodiment, the temperature of the reference or signal liquids in the cell are changed in a controlled manner over time in order to provide a reference or calibration signal. For example, the "gain" of the system may be determined by measuring the known absorption of the reference liquid at two different reference liquid temperatures.

Figure 24:
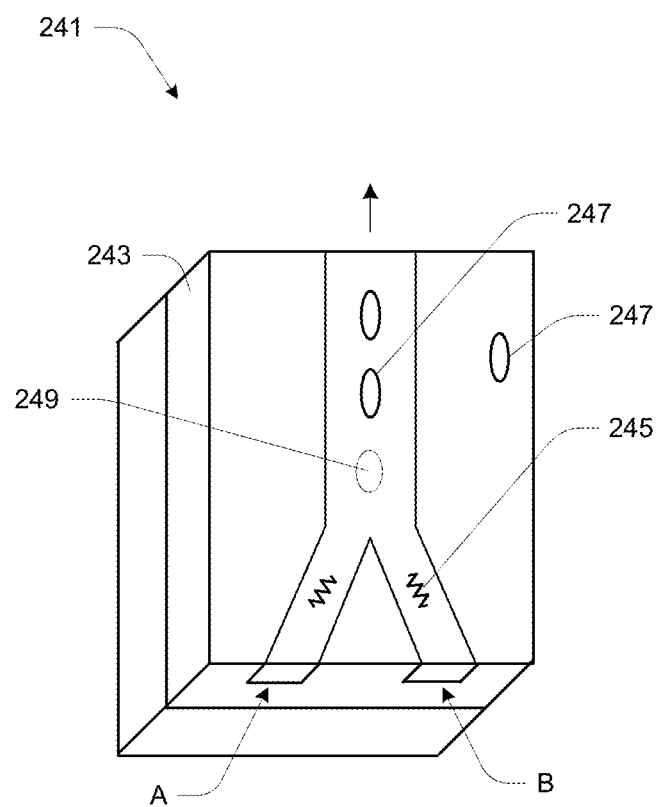
FIG. 24 is a schematic diagram of a fluid flow cell.

FIG. 24 shows that a microfluidic device 241 may be built with a silicon substrate 243 that includes resistive heaters 245 and temperature sensors 247 fabricated on one its surfaces using well known semiconductor processing techniques. The heaters 245 and temperature sensors 247 may be placed to heat and sense the entire microfluidic device, or may be placed to heat and sense individual microfluidic channels, or may be placed to alternatively sense the reference and sample fluid temperature during the modulation of the fluids in the interrogation region 249. In one embodiment, the temperature of the microfluidic device, the sample or the reference are changed to create a different or non-zero differential absorption between analyte and solvent or sample and reference. In another embodiment, the temperature of the liquids is measured (with or without temperature stabilization) and correction factor is applied to the measurement to account for changes in liquid temperature.

In another embodiment, a laser may be used to temperature modulate the stream prior to or simultaneous with the absorption measurement. The modulation frequency may be a frequency that is less than or greater than the alternating frequency of reference and sample measurement.

The reference liquid may be pulled from a reservoir that requires replenishment and thereby routine maintenance. In one embodiment, the reference liquid may be sample liquid that has been filtered or otherwise treated to remove the analyte and then recirculated for use as the reference liquid. A reference solution may be used in both the reference and sample streams in order to provide a "zero" point or other calibration of the system. In another embodiment, the reference fluid may be extracted from the same source as the sample fluid except at a different point in time, that is the reference fluid may be a time delayed version of the sample fluid (or vice versa). This embodiment may be advantageous in detecting changes in fluids or solutions over time, as may occur, by way of example, due to the introduction of contaminants, or the result of a chemical or biological process. The change over time may be accumulated or integrated to show not only a change over an increment of time but the total change from the start of the process (e.g. from the time the reference fluid was obtained).

In another embodiment the fluid analyzer may be used to perform the function of a liquid chromatograph (LC) detector. In the LC the potential reference fluid may be shared with a multiple analyte solvent as for an isocratic LC (single solvent). The LC may use a gradient elution. With gradient elution the "reference" is continually changing and may not be distinguishable from the sample solvent. In one embodiment, the eluent is split before arriving at the detection point and travels through a delay loop into the reference side of the fluid analyzer while the undelayed eluent is input into the sample side. The delay may be approximately ½ an absorption peak width of a subject analyte, and thus provide background compensation and a derivative spectrum may be generated by a reference and sample fluid analyzer technique as previously described. Other or variable delays may be used to compensate for the presence of additional analytes or interferers or may be used to compensate for elongation of the elution over time.

In another embodiment the microfluidic cell is designed to be a line replaceable part, thereby facilitating maintenance.

As is well known in microfluidics, two or more side by side liquid streams (i.e. no barrier between them) mix relatively slowly due to diffusion. In one embodiment, parallel reference and sample streams pass through the laser beam interrogation region and the resulting light absorption in each stream is measured using multiple or an array of detectors. In another embodiment, a non-flowing reference region separated with a barrier from the flowing streams may be measured and used as a reference.

In applications such as sensing oil in water, the oil (i.e. analyte) may adhere to and contaminate the optical surfaces of the cell over time. One advantage of the referencing techniques as described herein is that such static contaminate is present for both reference and sample measurement and thus can be referenced out of the measurement. During the measurement of the reference, a measurement of the change in reference stream transmission over time may be used to determine when window contaminate reaches a threshold value requiring cleaning or flushing of the cell interior surfaces (e.g. a detergent flush). Measurement of the change in transmission may include measurement of the emitted laser power through the use of an independent laser power measuring detector. Measurement of the change in transmission may include measurement of the absorption when both reference and sample are the same fluid. Measurement of multiple wavelengths with a tunable laser may also be used to determine the level of cell contamination, type of specific contaminating analyte or both.

Figure 25:
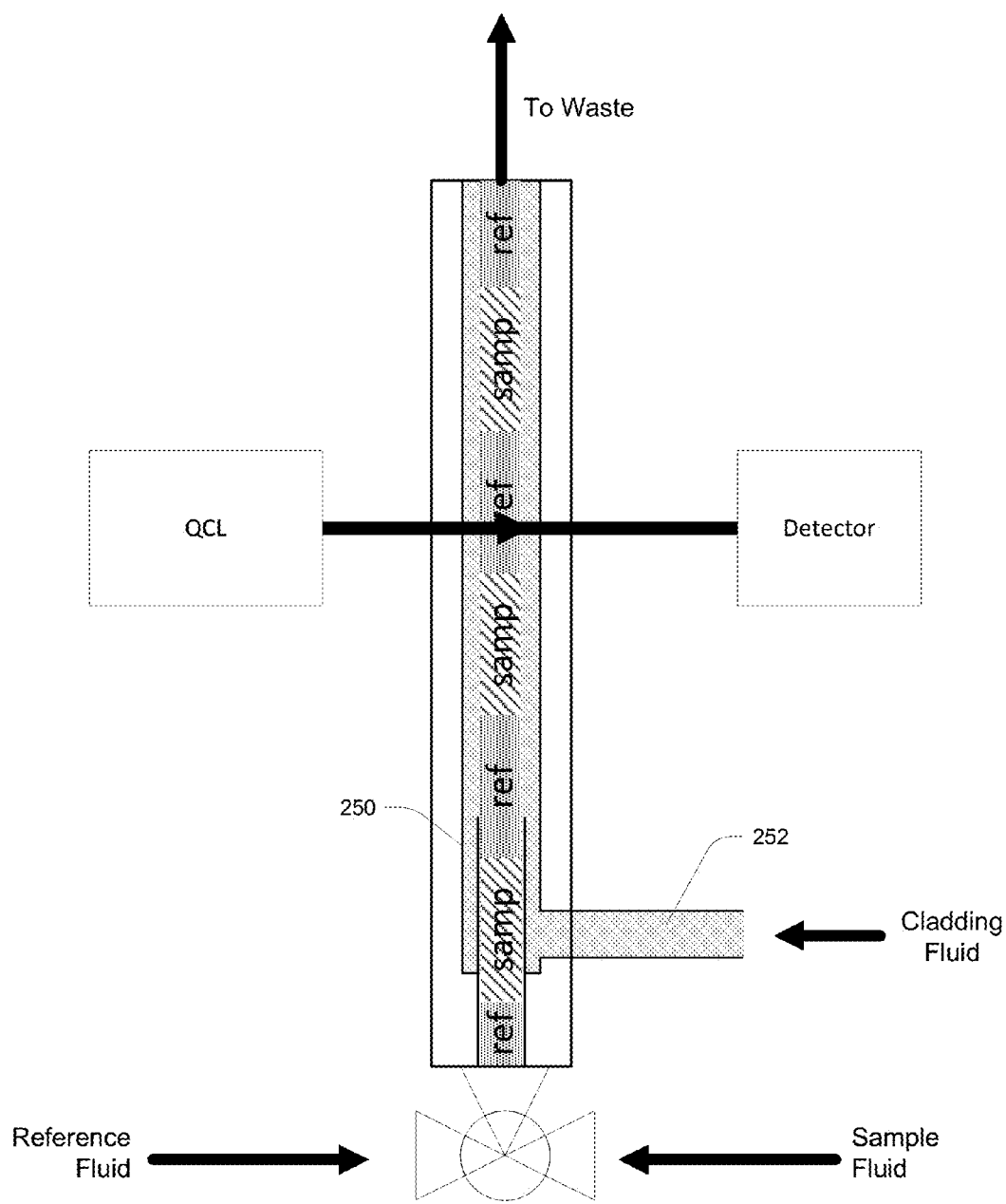
FIGS. 25-27 are schematic diagrams of fluid analyzers.

FIG. 25 shows an embodiment in which the sample and reference streams are encapsulated in a cladding stream 250 formed by a cladding fluid 252. The cladding stream 250 prevents the sample stream from contacting and contaminating the surfaces of the microfluidic cell, such as the optical window surfaces. The cladding stream 250 may be an optically transparent or an absorbing material. The cladding stream 250 may be cylindrical, fully encapsulating the stream as shown in FIG. 24 where the sample and reference streams are alternately injected into the center of the cladding stream 250 and forming the core of the composite stream. In one embodiment the stream may be cylindrical in shape with the cladding stream 250 having a circular cross section with a reference/sample stream core. In another embodiment the cladding stream 250 may have a rectangular cross section with a rectangular or circular reference/sample stream core. In another embodiment, the cladding may be on two sides of the reference/sample streams (i.e. a "sandwich" of one cladding stream, a reference or sample stream, and a second cladding stream) with the laser optical axis traveling through each layer. In another embodiment the cladding and reference streams may be the same substance.

In another embodiment, microdroplets may be introduced into the center of the stream. The microdroplet may be sample liquid and the surrounding stream may be reference liquid. The distance between droplets in the stream may exceed the width of the optical beam, the droplet size may be larger than the optical beam, and the reference measurement may take place between droplets and the sample measurement may take place as the droplet passes through the optical beam. In another embodiment both reference and sample may be introduced into the stream as droplets.

Figure 26:
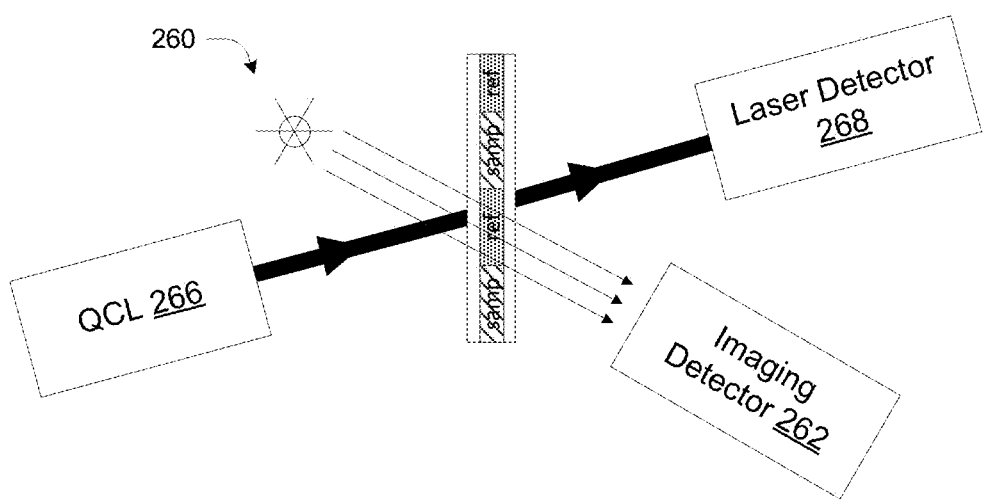

FIG. 26 illustrates an embodiment that includes an "imager" including a second source 260 and imaging detector 262 to simultaneously view the stream passing through the interrogation laser beam 264 at a second wavelength of operation. In this embodiment the sampling cell windows are substantially transmissive at both the laser and imager wavelengths. The imager may include magnification optics and use a shorter wavelength than the laser 266 (i.e. visible imager and IR laser 266). The signals from the imaging detector 262 and laser detector 268 pass to signal processing electronics (not shown), which uses the information in the imaging channel to improve the sensitivity or resolution of the absorption measurement. For example, a second channel imaging device may look for regions in the stream with particular characteristics (i.e. free of particulates or emulsions, a desired emulsion characteristics, flow rate, etc.) and gate the measurement of the absorption to be inside of or outside of this region. The second channel device may be used to look for effects induced by the laser beam in the stream, such as laser induced fluorescence or thermal effects due to heating of the liquid stream. The second channel device may be used to monitor the transmission cell channel for maintenance purposes, such as determining when the cell should be cleaned or replaced. The second channel device may be used to quantify particulates or other objects within the stream. The second channel optical signal may be enhanced by the use of an optical source such as an illuminator, LED or laser.

Design Considerations

As described above, a basis for a microfluidic analyzer system is a "T-channel" geometry, where separate streams of incoming analyte and reference fluids interface at an optical interrogation region within a test section of a microchannel. The mechanism for sampling a water-based solvent carrying a dilute analyte solution, compared to reference solution, is to modulate the fluid interface laterally across the interrogation region of an IR laser beam functioning as a probe. The probe beam then samples the solutions sequentially and repeatedly at high speed (e.g. 1-100 Hz), and the light transmitted through the device is captured by a detector. To drive the fluid interface at high speed may require temporal modulation of the analyte and reference stream flow rates via a pressurized gas system with fast electronic switching valves.

A desired optical interrogation volume for an IR laser may set much of the channel test section geometry. Example values for various parameters are given in Table 1 below. Target analytes may include small molecules such as hexane and pentane or larger, where the solvent has similar mechanical properties to water. Additionally, the device may be fabricated from IR transparent materials (3-15 μm) when an IR beam is used, e.g. including silicon and calcium fluoride, where at least one window may be transparent in the visible spectrum (400-700 nm) for microfluidics diagnostics and additional methods of analyte detection.

TABLE 1

Microfluidic system design example

| Parameter | Symbol | Nominal | Typical Range |
|---|---|---|---|
| Interrogation beam diameter | $D_0$ | 1 mm | 0.1-10 mm |
| Test channel width | $W_t$ | 2 mm | 0.1-2.0 mm |
| Fluid interface modulation frequency | f | 10 Hz | 1-100 Hz |
| Channel height | H | 150 μm | 25-250 μm |
| Analyte size (e.g. hexane, pentane or larger) | MW | 100 g/mol | ≥100 g/mol |
| Ambient temperature | T | 22° C. | 10° C.-50° C. |
| Solvent/reference fluid | — | Water | — |

Figure 27:
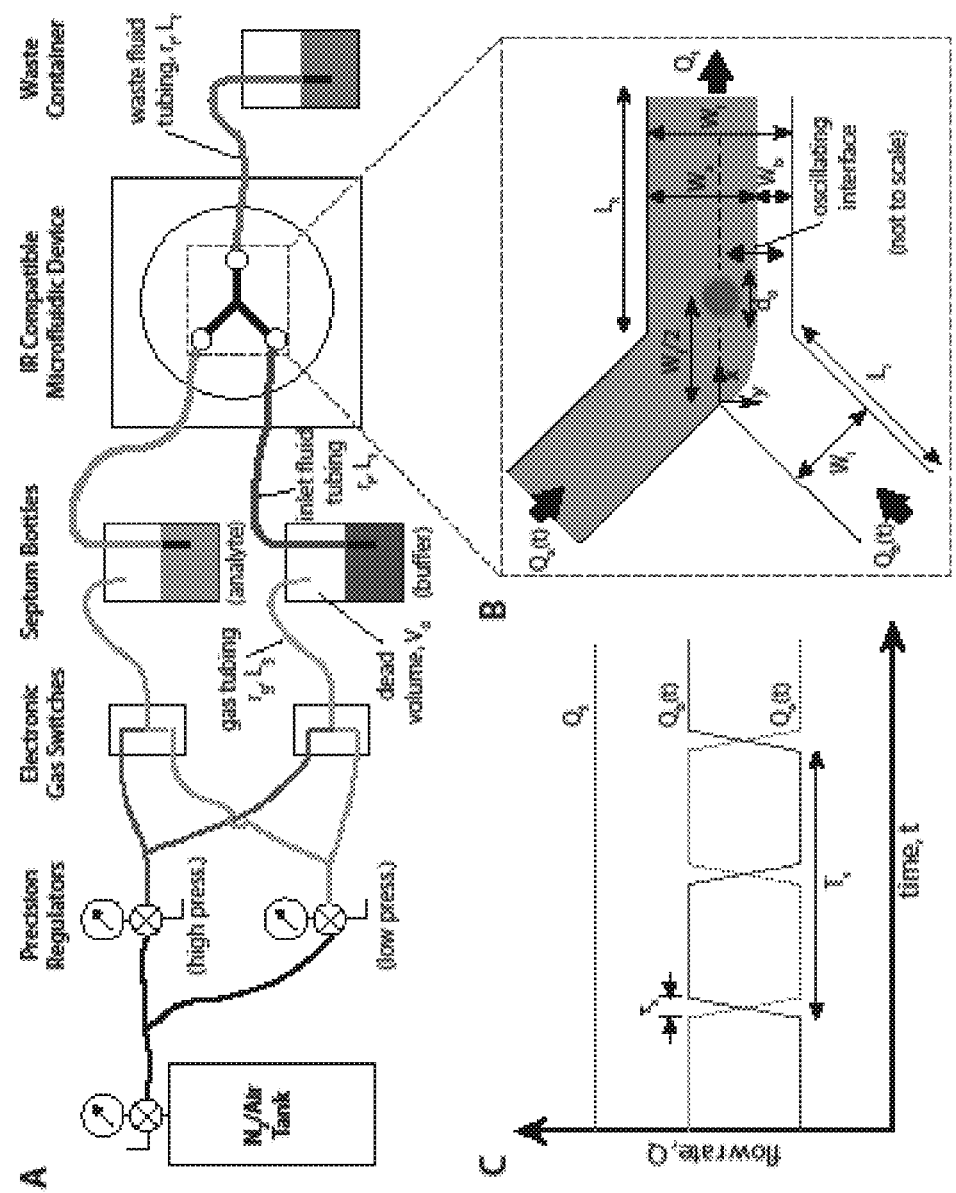

FIG. 27 shows an overall pressure-driven microfluidic system design concept and channel geometry. Section A shows pressure system and microfluidic channel overview schematic. Section B shows microchannel junction geometry showing the analyte and interface relative to the interrogation beam. Section C shows flow rate modulation scheme for the analyte and reference streams to deflect the fluid interface across the interrogation beam.

Due to the large potential parameter space for the microfluidic device and pressure system, several geometric and physical variables may be constrained in order to simplify the design process. Examples of ranges and design values are shown in Table 2. These can be chosen based on availability and cost of common products and materials for microfluidic and pressure systems, and in some cases their physical limitations. These can include the following:

The geometry of the analyte and reference stream components and microchannel dimensions are assumed to be symmetric. Because both fluid streams have similar mechanical properties ('water-like' viscosity) and the flow of each fluid in the test section of the microchannel is modulated symmetrically with the other, the physical dimensions of the components carrying each stream should also be equal.

The driving pressure for the system is chosen a priori. The driving pressure is one of the more critical design choices in the system: too high and there is a risk of leakage/damage to the microchannel, too low and pressure becomes difficult and expensive to regulate.

Analyte solvent and reference fluids have the mechanical properties of water.

Analytes have transport properties similar to small gaseous molecules in water.

TABLE 2

Example values for device and pressure system components

| Component | Parameter | Symbol | Typical Range | Design Value |
|---|---|---|---|---|
| Gas tubing | Radius | $r_g$ | 0.1-10 mm | (variable) |
| | Length | $L_g$ | ≥150 mm | 150 mm |
| Septum bottle | Dead volume | $V_d$ | 1-10 cm$^3$ | (variable) |
| Fluid tubing | Radius | $r_f$ | 0.1-0.5 mm | 0.25 mm |
| | Length | $L_f$ | ≥150 mm | 150 mm |
| Microfluidic device | Height | H | 25-250 μm | (variable) |
| | Inlet width | $W_i$ | 0.1-2.0 mm | (variable) |
| | Inlet length | $L_i$ | ≥5 mm | (variable) |
| | Test channel width | $W_t$ | 0.1-2.0 mm | (variable) |
| | Test channel length | $L_t$ | ≥5 mm | 10 mm |
| Driving pressure | Mean pressure | p | 1-10 psi | 1 psi |

Upon contact between the analyte and reference streams at the junction within the microchannel, the analyte will migrate due to molecular diffusion into the reference stream. The initially sharp analyte concentration gradient at the interface between the two streams drives diffusive flux, making the analyte interface more diffuse with time, eventually contaminating the entire reference stream.

Flow system analysis can be performed using a fluid circuit analogy, whereby tubes and channels provide a 'hydrodynamic resistance' to fluid flow under a driving pressure, and gas compressibility and tubing compliance provides a 'hydrodynamic capacitance'.

An alternative, yet simple approach to generate sufficient hydrodynamic resistance is to add a small (~50 μm diameter) capillary tube to each branch of the inlet tubing of the fluid delivery system, upstream from the microfluidic device. A convenient consequence of the low hydrodynamic resistance in the channels is that the pressure-driven flow system design is relatively independent of the microfluidic channel dimensions. The channel dimensions may thus be chosen to optimally suit requirements, while maintaining low Reynolds number flow.

There are considerations of sufficient resistance to the fluid flow to accurately control the driving pressure. Insufficient resistance can result from relatively large channel cross-sectional area, which would require impractically long channel lengths (Wi~1 m) to sufficiently increase channel resistance. While such dimensions could be achieved with conventional devices, it may be desired to avoid complex channel designs. With these factors in mind, possible channel and pressure system parameters are provided in Table 3. To compensate for the lack of hydrodynamic resistance by the microfluidic channel, small diameter capillary tubing may be added upstream of the microfluidic device. An added advantage of this approach is that coarse adjustments to the system dynamics (flow speed, hydrodynamic resistance) may be performed without additional microfabrication. Upon final assembly of such a device, hydrodynamic performance can be measured empirically and adjusted accordingly, as slight variations in device dimension (e.g. microfluidic device thickness) may have a large impact on performance.

TABLE 3

Example microfluidic channel and pressure system parameters

| Component | Parameter | Symbol | Final Design |
|---|---|---|---|
| Gas tubing | Radius | $r_g$ | 0.5 mm |
| | Length | $L_g$ | 150 mm |
| Fluid tubing | Radius | $r_f$ | 250 μm |
| | Length | $L_f$ | 150 mm |
| Capillary tubing | Radius | $r_c$ | 25 μm |
| | Length | $L_c$ | 10 mm |
| Microfluidic device | Height | H | 150 μm |
| | Inlet width | $W_i$ | 1.0 mm |
| | Inlet length | $L_i$ | 7.5 mm |
| | Test channel width | $W_t$ | 2.0 mm |
| | Test channel length | $L_t$ | 7.5 mm |
| Driving pressure | Mean pressure | p | 2.5 psi |
| Flow speed | Mean speed | U | 1-10 mm/s |
| Interrogation beam | Diameter | $d_0$ | 0.5 mm |

Key components for the pressure control system can include a compressed nitrogen or air tank with regulator, and/or dual channel function generator, or similar electronic control.

The complexity and dimensions of the final microfluidic device design can dictate the complexity and cost of the fabrication method. Potential designs may require IR transparent (silicon, calcium fluoride, zinc selenide or sulfide, germanium) substrates, either wafers or windows≈1 mm thick, with at least one being transparent in the visible range (e.g. calcium fluoride) for flow diagnostics. One basic approach is to create a 'sandwich' comprising two IR transparent windows separated by a gasket with a thickness that defines a depth≈150 μm of the microchannel. The gasket material will be patterned with the device design through micromachining, laser cutting, or lithography (see below), where the gasket will form the lateral walls and the IR transparent windows will form the top and bottom walls of the microchannel. The gasket or other fluid cell materials may be selected for chemical compatibility with the fluidics or optical light source. The upper IR transparent window may include three micromachined holes: two for the analyte and reference stream inlets, and one for the test channel outlet. Additionally, a clamping mechanism may be fabricated to prevent de-lamination of the device during operation. All silicon device fabrication consisting of etched channels in a silicon substrate bonded to another flat substrate may also be used in optical cell construction.

It may be possible to extract analyte diffusivities or other fluid boundary characteristics simultaneously during spectroscopy measurements. For example, during modulation of the analyte-reference fluid interface, the spectroscopy instrumentation is measuring analyte concentration at a fixed position along the channel (e.g. at the interrogation region) or analogously a fixed time after the fluid streams meet. Considering that the interface is modulated across the interrogation beam in time, the measured analyte concentration signal over time is effectively a spatial concentration profile of the analyte. The concentration profile depends upon the diffusion coefficient, which can be ascertained directly from the concentration profile itself, given the diffusion time. The diameter of the interrogation beam may be reduced to improve measurement accuracy. For example, the beam diameter may be one tenth of the expected width of the interdiffusion at the interrogation region. As disclosed with respect to multiple interrogation regions, the position of the interrogation region within the fluid channel (i.e. to select longer or shorter times of interfusion at constant stream velocity) may be varied by mechanical means or by use of multiple static interrogation regions. In other embodiments, the fluid velocity may be varied to change the time of fluid interaction (e.g. interdiffusion) prior to arrival at the interrogation region.

Most microfluidics applications screen samples in a batch operation rather than continuous mode of operation using a segregated amount of material. For continuous sampling by the analyte stream from a line process, the analyte stream would need to be siphoned off of the original process and introduced into the microfluidic device without disrupting pressure/flow rate balances in the channel. One option is to eliminate pressure modulation from one side of the channel (e.g. analyte side), opting rather to hold it at a steady pressure or possibly steady flow rate through the microfluidic device. This steady pressure or flow rate may be supplied by the line process which is being monitored. Modulation of the reference stream via pressure changes will still continue to modulate the fluid interface in the test channel, but it will do so in a nonlinear way and will also modulate the flow rate. It is also possible to achieve sample stream deflection, which is linear with pressure modulation, through the addition of a bypass channel parallel to the test channel.

Additional Embodiments

In other embodiments it may be desirable to separate the analyte and reference streams with a physical barrier. This may be advantageous to prevent the fluid streams from mixing, for example through diffusion.

Figure 28:
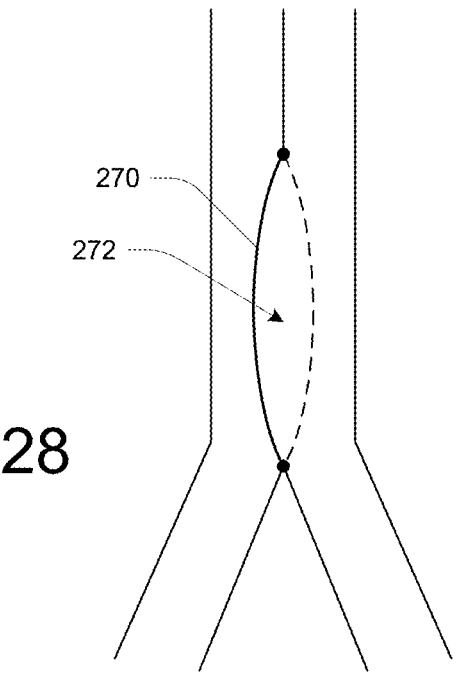
FIGS. 28-29 are schematic diagrams of a fluid merging location in a flow cell.
Figure 29:
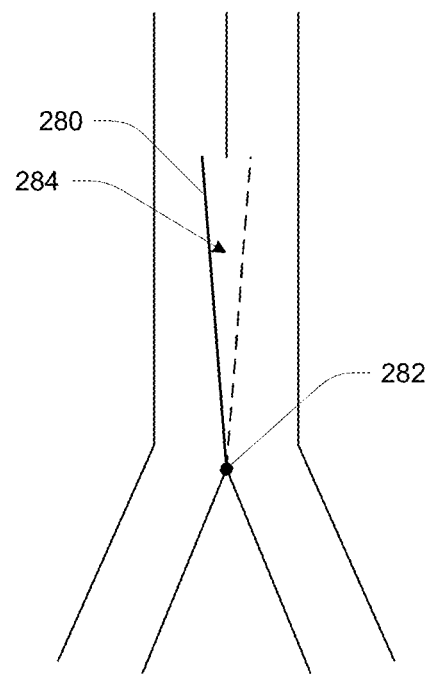

FIGS. 28 and 29 show a microfluidic cell as previously disclosed with the addition of a barrier between the reference and sample streams. In FIG. 28, the barrier 270 is a flexible membrane such that as the pressure differential in the streams varies to bring the reference and sample streams into the interrogation region, the membrane is sufficiently elastic to enable the streams to be analyzed. The pressure difference between streams may be greater than that required without the barrier. As is known in the art, microfluidic cells may be constructed with a polymer or other material of the desired thickness sandwiched between two plates (or windows as previously disclosed). The polymer material may be patterned using photolithographic or other techniques known in the art, and the same method may be used to pattern the barrier into the polymer which is sufficiently thin and elastic to deform when subject to the pressure differential between the streams. Alternatively a very thin elastic material may be attached proximate to the junction of reference and sample streams.

As shown in FIG. 29, a barrier 280 may be constructed to be attached only at one end 282, to create a "waving" barrier that moves back and forth through the interrogation region 284 in response to the variation in pressure differential changes between the two streams. The barrier 282 may be constructed to have a thickness that is less than the separation between the optical top and bottom windows (and the polymer thickness on the sides of the channels) in order to avoid contact with the windows. In another embodiment, the barrier 282 will be designed to lightly contact the windows. The barrier 282 may be used to remove some, most or all of the zero-flow region liquid (as previously disclosed) in close proximity to the windows. This may be advantageous to taking optical measurement with reduced a zero-flow region which, may contain diffused or undiffused reference or sample liquids.

Bubbles, particulates, undissolved analytes and other objects in the stream may interfere with the flow of liquid in the cell. Particulates of higher density fluids may be added to the streams and the streams operated at an increased Reynolds number relative to non-cleaning operation to dislodge or remove the objects from the cell, and such particulates may be introduced as part of a special "cleaning stream" or as dispersed particles in the analyte and/or reference streams where measurements are performed between the particles. Stream velocity may be increased periodically to perform the same function. A laser optical source may also be used to heat the objects in order to dissipate, dislodge or remove the objects from the interrogation region. The laser may also be pointed or translated (or the cell translated relative the laser) in order to perform the same function at locations other than the interrogation region.

The detector may have an optical filter to pass light from the optical source and block light at other wavelengths, as for example, may be emitted through blackbody emission from objects or liquids heated by the optical source.

When objects in the streams have an optical absorption greater or less than the liquids in which they are contained, differential heating may occur. For example, an oil droplet may be heated above the temperature of the water in an oil-in-water measurement where some of the oil may be immiscible. Through blackbody emission, this differential signal may be observable when collected by an infrared point or imaging detector. The infrared detector may have an optical filter to screen out the emission from the optical source. The optical filter may also be a bandpass filter designed to pass light at specific wavelengths where the liquid has higher optical transmission. In this manner an optical source at one wavelength may be used to differentially heat an object in the liquid to create a differential optical signal between liquid and object through blackbody emission that is then collected by a filter and detector at a wavelength different than the optical source. Thus, in one embodiment both transmission and emission detection may be performed, where transmission is used to detect immiscible analytes and infrared emission is used to detect or image non-immiscible analytes. The emission measurement may be taken on one side of the cell (e.g. same side as optical source) to minimize absorption in the liquid (i.e. shorter pathlength) with the transmission measurement taken on the opposite surface to achieve full transmission through the cell.

Additional embodiments may make use of hydrodynamic focusing or fluidic beam steering as may be used in microfluidic cell sorters to create oscillating reference and analyte streams at the optical interrogation area.

Figure 30:
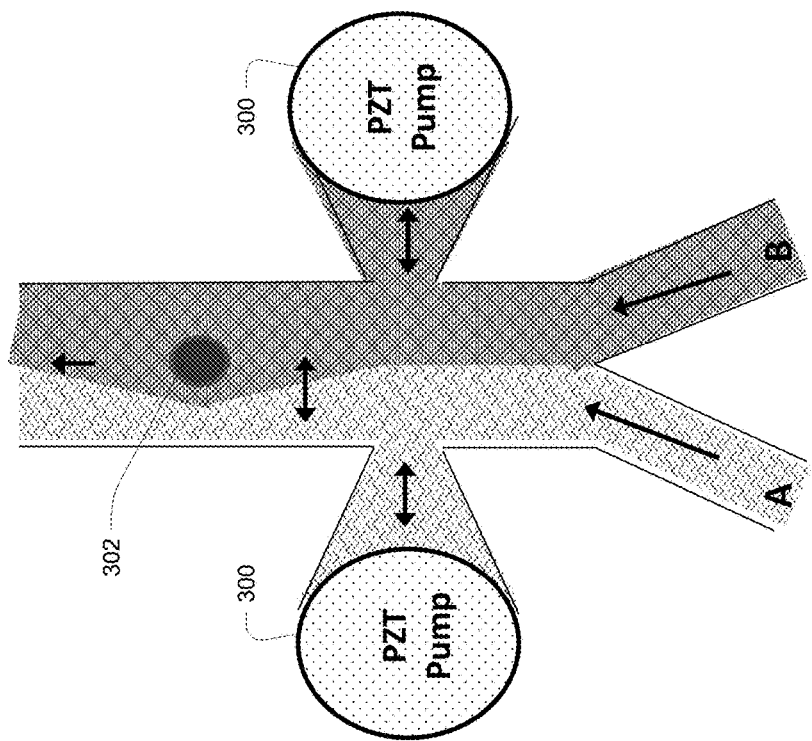
FIGS. 30-37 are schematic diagrams of fluid analyzers.
Figure 31:
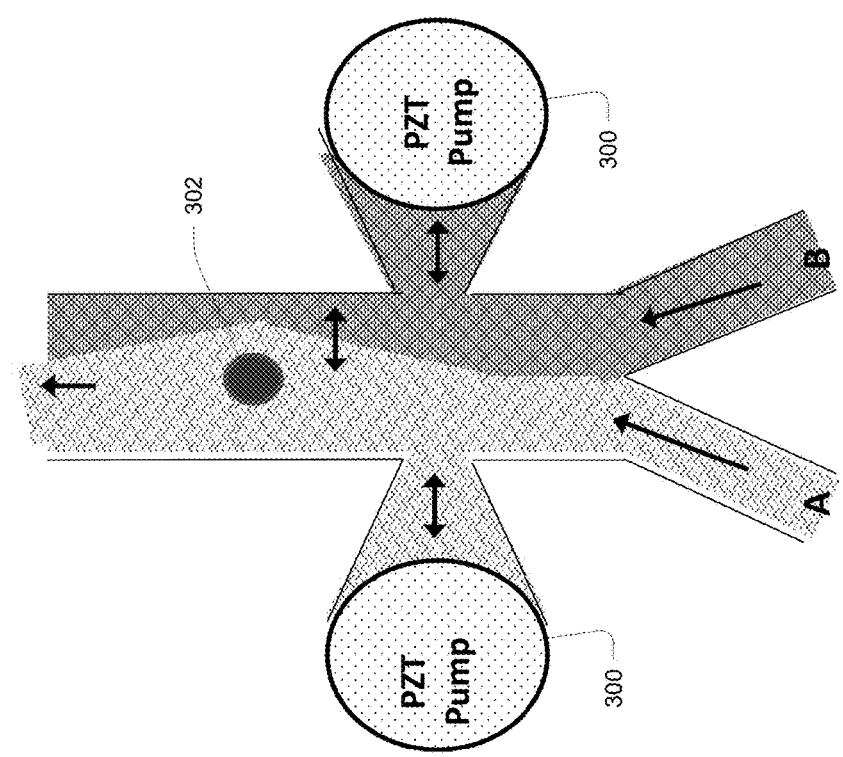

FIGS. 30-31 show an embodiment making use of one (or optionally more) PZT piston type side injection pumps 300 (or equivalent as known in the art) in the region after the two streams have merged to move the reference and analyte streams through the interrogation area. The PZT pump may be advantageous because it may not be a pump in the traditional sense of injecting liquid; it could just displace a volume in an oscillatory manner (e.g. by deforming a compliant microchannel substrate or through the use of a piezoelectric diaphragm micropump as known in the industry) to move the stream boundary. The use of PZT pumps and the location of the pumps may be selected to provide an increased speed of oscillation relative to modulation of the reference and analyte through the interrogation point using pressure differentials of the reference and analyte streams prior to merging (as described previously). Other types of pumps may be used. In one embodiment, the oscillations may take place at a 1 kHz rate. A lens or aperture may be used to create a smaller interrogation area. The sampling cell and fluid channel may be designed to support multiple lateral "side to side" (e.g. right to left to right in FIG. 30) oscillations of the fluid boundary over the length of the fluid channel.

Different types of micropumps may be used, including both mechanical displacement pumps (e.g. electrostatic vibrating diaphragm, Piezo peristaltic, thermo-pneumatic, bimetallic, polymer film and electromagnetic) as well as certain types of non-mechanical micropumps such as those based on hydrodynamics. Using MEMS technologies, the micropump and microfluidic channel may be integrated onto a single device. By way of example, the channel may be formed in silicon and the pump diaphragm may be formed as part of the sides of the channel, behind which may be a reservoir of liquid or air. Pressure variations of the reservoir or electrostatic motion of the diaphragm may then induce motion of the boundary layer in the channel. Thus the microfluidic device may consist of a pump and optional reservoir, microfluidic channel with reference and analyte fluid streams, and in one embodiment, the semiconductor optical source.

PZTs have motion that in many applications are measured in a closed feedback system in order to achieve more repeatable or improved performance. Such a feedback system may be employed to ensure that the PZT pump operation is highly repeatable in order to increase the accuracy of the analyte measurement. One precise measurement technique would be to reflect a light source off a membrane or other surface whose motion is determined by the motion of the PZT and to use the reflected light to provide feedback to the PZT controller or, in another embodiment, to correct in signal processing the calculation of the analyte property with the as-measured motion of the membrane of other surface. The same light source may be used for both the analyte measurement and the motion measurement.

In another embodiment, the PZT may inject fluid into the fluidic cell channel from a reservoir. The reservoir may have static fluid (e.g. the reference or analyte liquids) over the time frame of the several measurements of the interrogation area. The reservoir may be replenished over time, and the replenishment may be to prevent contamination of the reservoir by the other fluids in the channel. The reservoir may also be used to inject an analyte bearing fluid of known properties (e.g. concentration). In another embodiment, the PZT pump may move a flexible membrane as shown in FIG. 31 in particular. The flexible membrane may form a side wall of the fluidic cell, and the cell wall may be adjacent to, or in close physical proximity to an interrogation region relative to the length of the microfluidic channel length in the cell.

In another embodiment, the pump may be located in a first inlet channel (e.g. A) prior to the merging of the two streams to provide an oscillating pressure on one of the streams while the second stream has nominal constant pressure (e.g. B). The nominal second stream pressure may be more than, equal to, or less than the average pressure on the first oscillating stream in order to optimize the average location of the interface of the two streams at the interrogation point. In another embodiment, the connection between the flow cell and the PZT pump may be through a vibration isolation connection (e.g. a flexible hose). In another embodiment, as shown, the pump may be directly connected to, or built as an integral part of, the cell, such as in a micro-electro-mechanical-system (MEMS) based micropump as is known in the art.

In another embodiment, the PZT modulation pump may be used for each stream prior to the merging of the two streams. The induced modulations of the multiple pumps may be synchronous and at a fixed phase relationship. The pumps may be operated at the same modulation frequency or different frequencies or phases in order to achieve a desired modulation of the liquids at a collocated or a downstream interrogation region.

In another embodiment a third inlet stream C (not shown) may be used to introduce a third liquid into the combined stream. The third stream may be an additional analyte for measurement or may also be the reference liquid (e.g. A) and may perform as a "cladding" liquid as discussed previously to provide additional control over, for example, the analyte stream B spatial position within the stream.

The PZT pumps or a pressure transducer may provide a signal to a set of control electronics for the purpose of demodulating or phase-locking the pressure variations to the optical signal coming from a detector or transducer at the optical interrogation area.

Figure 32:
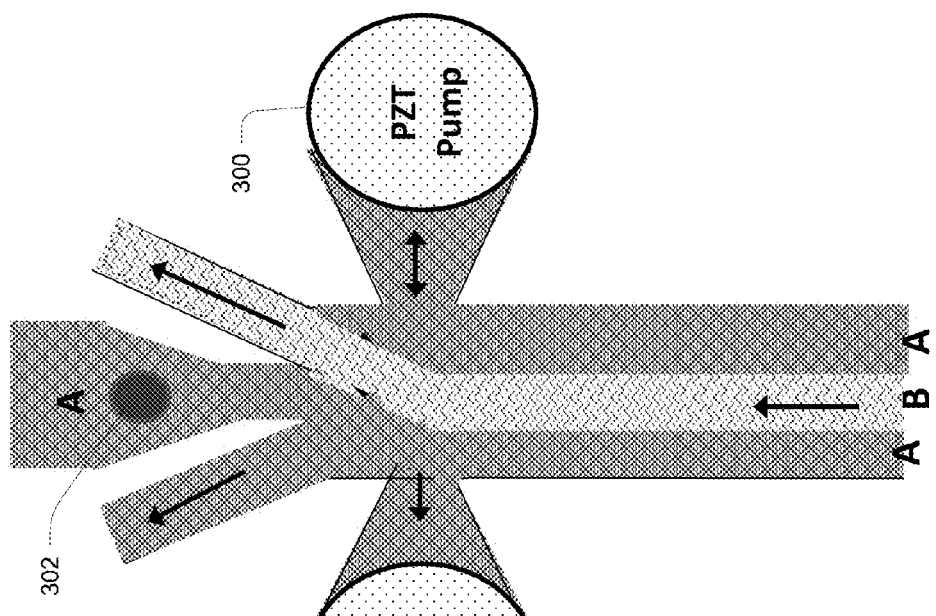
Figure 33:
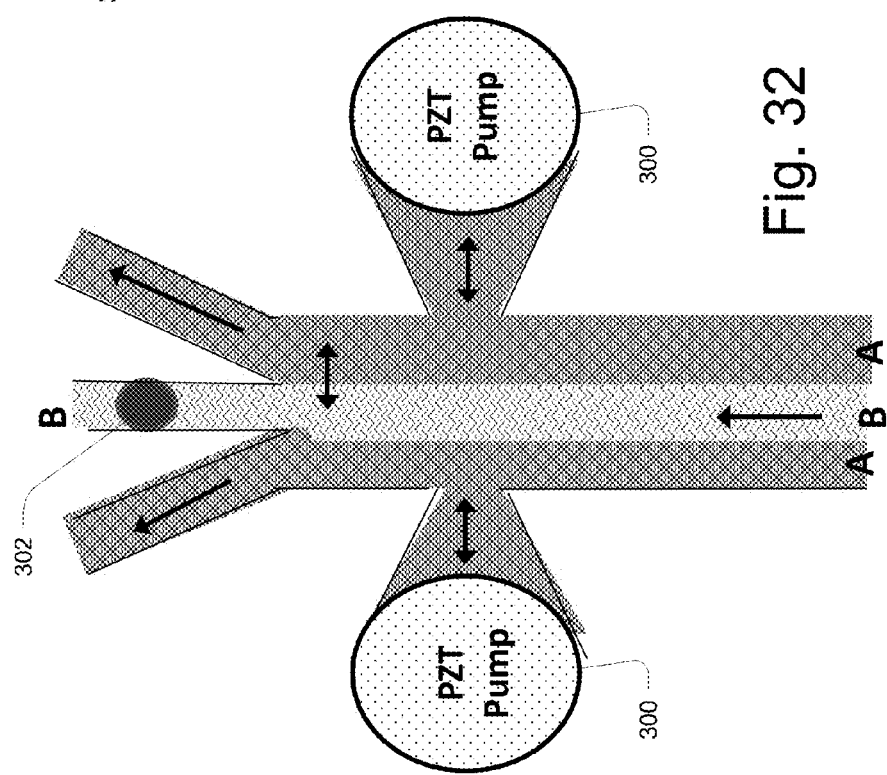
Figures 34, 35:
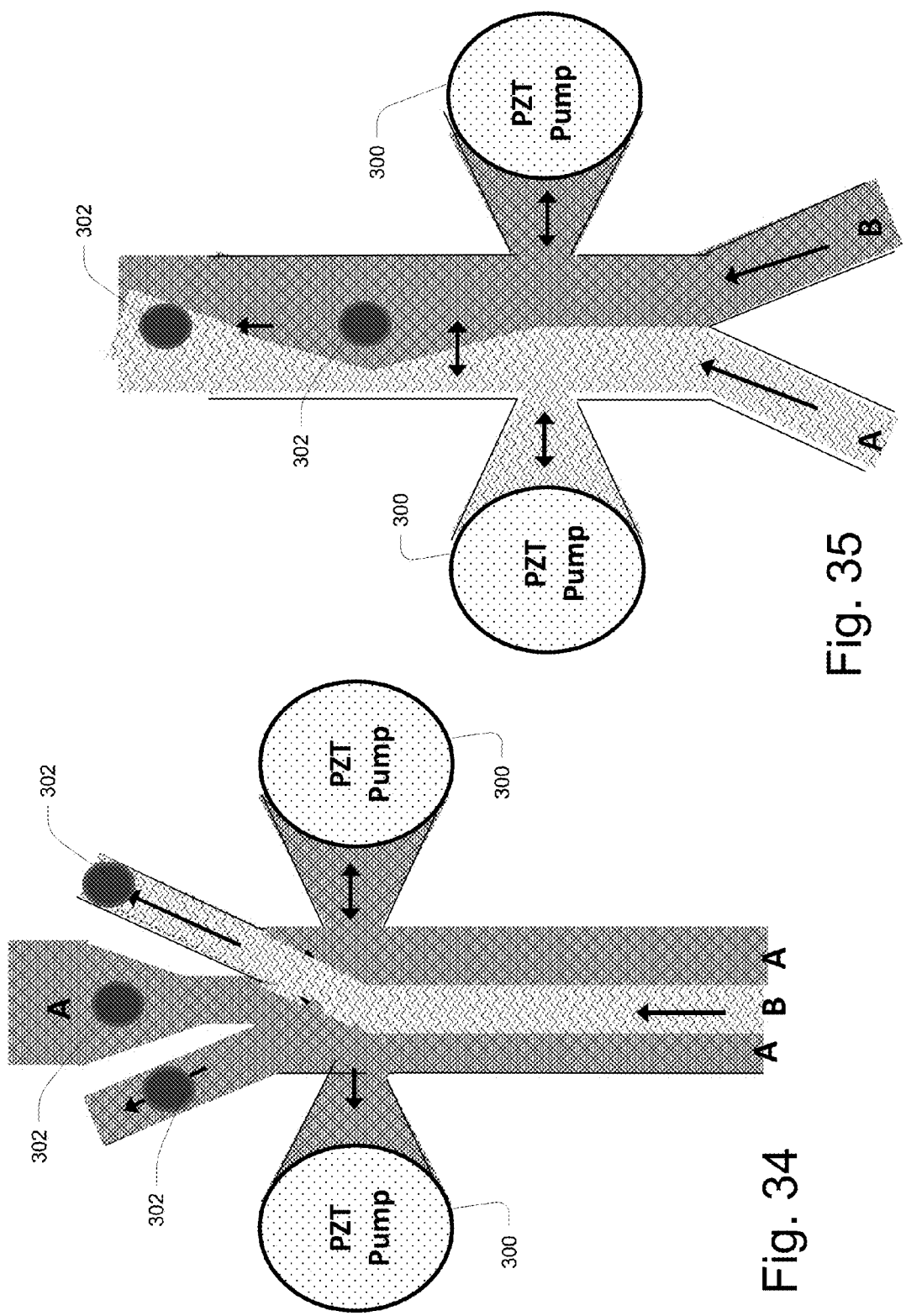

FIG. 32-33 show another embodiment in which the side channel pumps or pressure differences in the two streams may be used to alternately direct the reference streams A and B into separate outlet channels, including one with an interrogation channel. This may be advantageous to provide an interrogation point that is downstream from the pumps. In another embodiment, it may be advantageous to taper or select a width of the interrogation stream channel. The width of the separation channel may be larger or smaller than the deviation of the stream boundary in the upstream combined channel. In this manner the flow characteristics and optical interrogation region may be decoupled from the required width of the interrogation region. Those versed in the art will recognize that upstream pressure differences may also be used to direct the stream into separate interrogation channels FIGS. 34-35 show an embodiment in which multiple interrogation areas may be utilized. The interrogation areas may be in separate downstream channels (FIG. 34) or in the same channel (FIG. 35). The interrogation points may be at different optical wavelengths. The interrogation areas may be used to measure a different physical property of the liquids through additional detection methods, for example fluorescence, reflectivity at a desired optical wavelength, or temperature. The PZT stream modulation frequency, the effective diffusion rate of liquid B into liquid A and the flow rate of the stream may be used to determine the physical separation between the interrogation points. The modulation frequency may be sinusoidal or square wave in nature, or may be an arbitrary waveform, as may be determined at least in part due to signal processing considerations for the transducer measurement at the interrogation point. In one embodiment, the same optical source (e.g. a laser) may be used for multiple interrogation areas through the use of optical components to split and direct the source radiation to the multiple interrogation regions. A detector may be used in each interrogation region to collect the transmitted source radiation, and the detector signals then used in signal processing to calculate a property of the liquid flowing through the cell (e.g. analyte concentration).

Multiple PZT pumps (not shown) may also be used to inject additional analytes for measurement. The pumps may be synchronized to achieve a desired sequence of liquids at a downstream measurement point.

Figure 37:
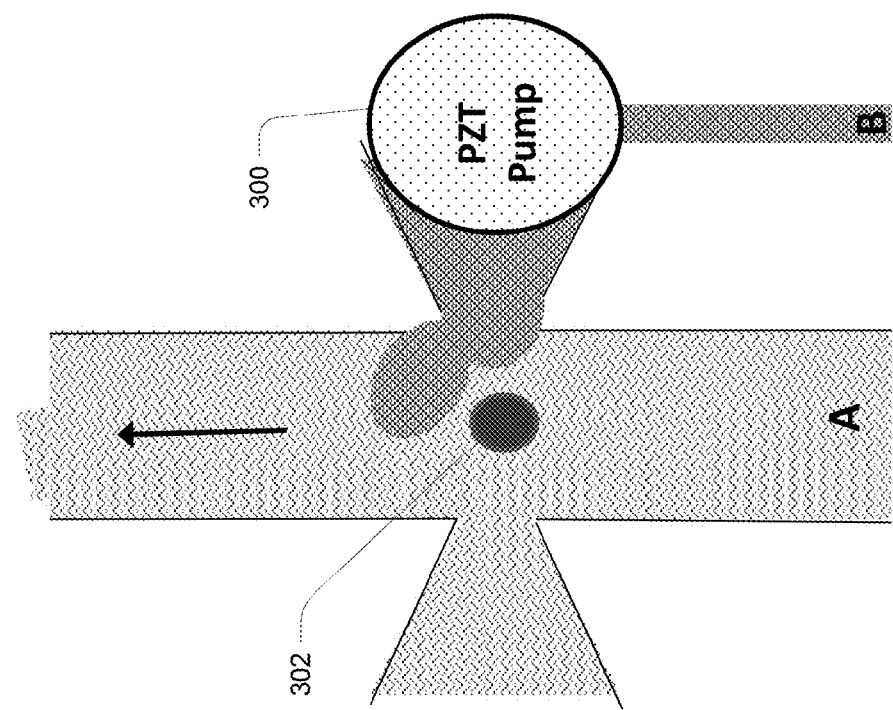
Figure 36:
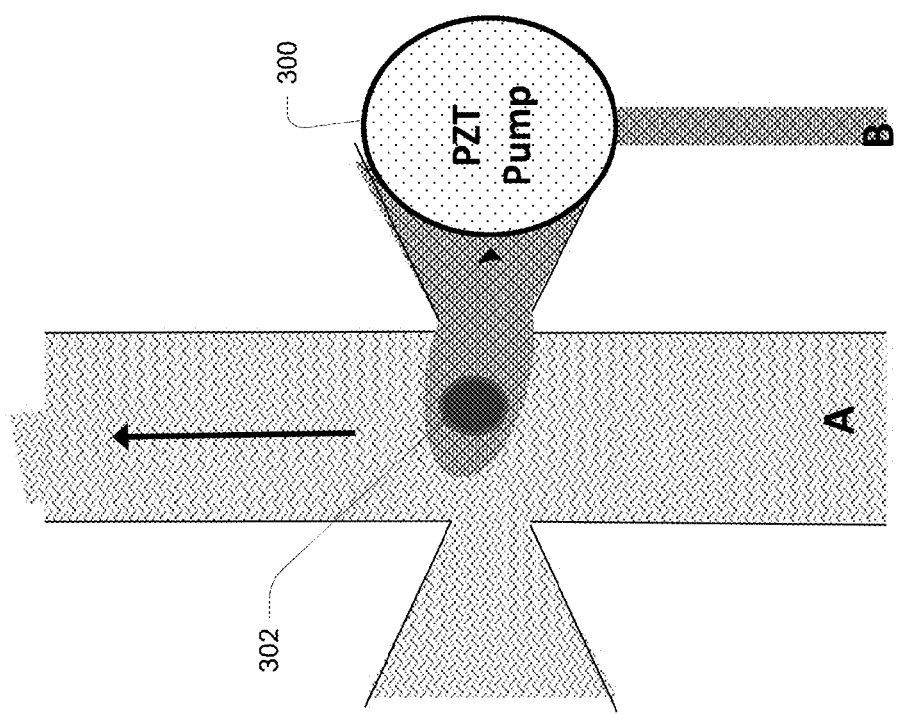
Figure 38:
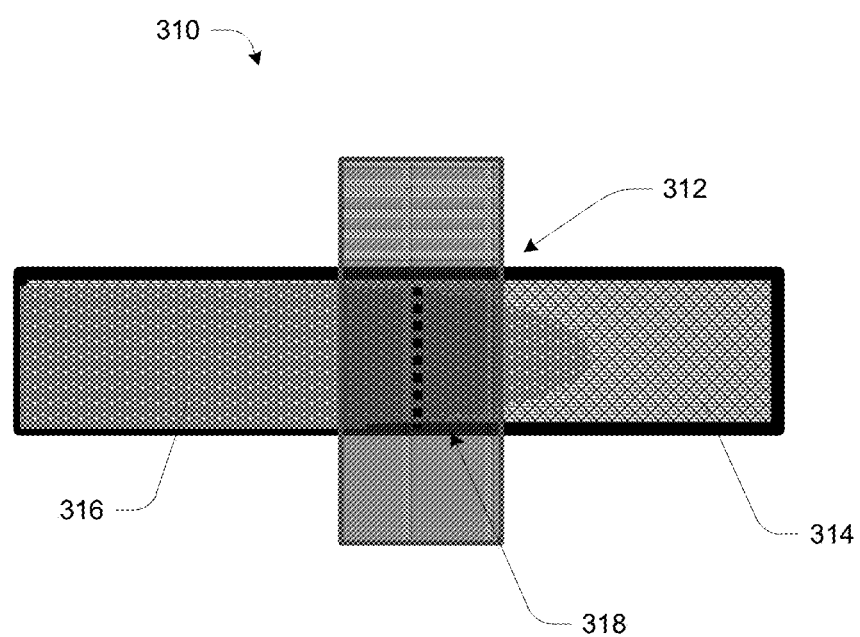
FIGS. 38-42 are schematic diagrams of portions of fluid flow channels.
Figure 39:
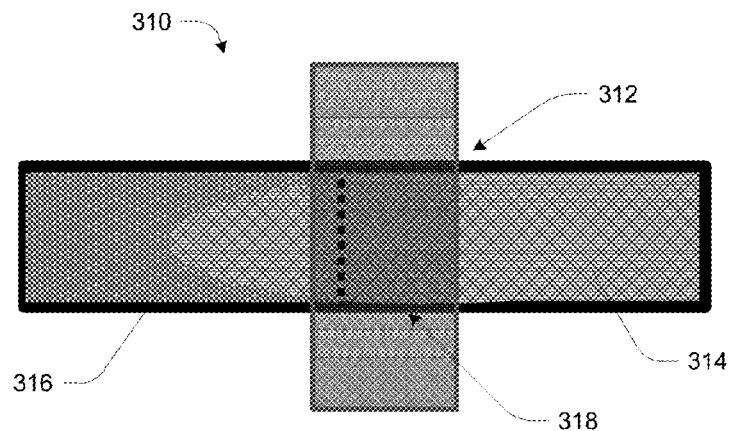
Figure 40:
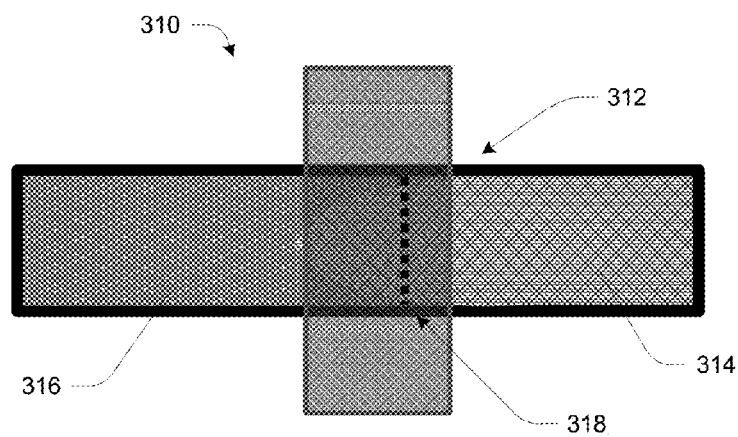
Figure 41:
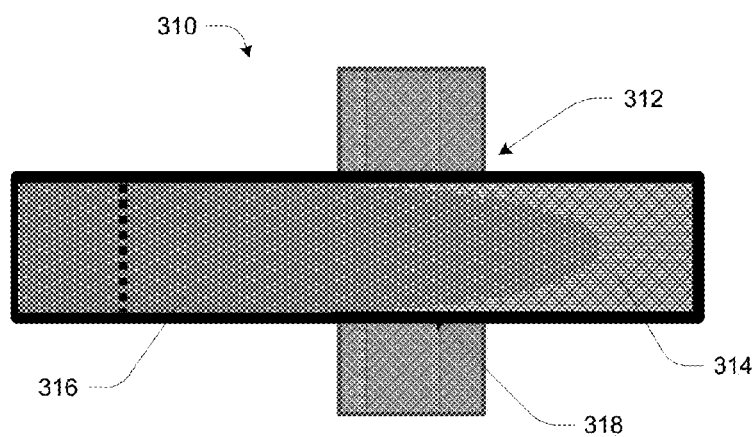

FIGS. 36-37 show an embodiment in which the PZT pump may be used as the injection point for the analyte B into a reference liquid A (the converse also being possible). The velocity of the reference stream A, and physical dimensions of the PZT injection orifice, the PZT pump pressure and modulation frequency may all be optimized to achieve a certain characteristic of the interrogation point, such as its physical dimensions. In one embodiment the reference liquid A may not be streaming and may be stationary for the measurement period, and then flushed to remove liquid A and analyte B. The time between flushes may be a function of the rate of diffusion of the analyte into the reference liquid. It may also be related to the viscoelastic and surface adhesion properties.

As described previously, the measurement point may include a laser and a detector for measuring the intensity of the laser signal after passing through the liquid. The measurement point may include additional detectors located to detect laser signals that may be scattered, reflected or diffracted off particles in the liquid being measured. More than one laser or optical wavelength may be used.

It should be clear to those versed in the art that different combinations and numbers of reference and analyte streams may be included in other embodiments based on the design principals described in these prior embodiments. In one embodiment, external fluid switches can be used to swap the reference and analyte inlet streams spatially in the fluid channel, thus providing a "mirror image" measurement where, in FIGS. 30-31 the A and B streams at the inlets are reversed periodically in order to account for an asymmetry in the streams that may vary over time. In one embodiment, by way of example, fluid A may be at one pressure in the left inlet channel and fluid B at a lower second pressure in the right inlet channel for a first interrogation point measurement. Then for a second interrogation point measurement and through the use of a valve, fluid B may be at the one pressure in the left inlet channel and fluid A at the lower second pressure in the right inlet channel. In this manner, the interrogation point will alternatively contain fluid A and fluid B for the measurement. This embodiment may be advantageous in mitigating the effects of contamination of the sidewalls of the cell by, for example, oil in the analyte fluid. The amount of contamination may be measured over time by measuring the signal transmitted through the interrogation region or in comparison to the signal strength prior to its passing through the interrogation region.

In one embodiment, the spatial positions of the analyte and reference fluids in the fluid channel are periodically reversed, and a corrected value of the sample optical property is determined from the reversed and the unreversed measured values of the optical property.

In one embodiment the inlet channels may be fed by tubing or piping that is substantially longer in length than the fluid channel length within the microfluidic cell containing the inlet channels and interrogation region in order to separate the location of remotely located pump and/or valves from the microfluidic cell. The boundary region between the reference and analyte liquids in the interrogation region may move simultaneously through the interrogation region (or essentially simultaneously on the scale of the measurements) with a change in pressure at the remote pump or valves as a result of the incompressibility of the fluids in the cell (e.g. in the embodiment of FIG. 19). In another embodiment (e.g. FIG. 1, referred to as "serial-streaming" as opposed to the "parallel-streaming" in FIG. 19) where first one fluid and then the second fluid are alternately passed through the interrogation region in a sequence of fluid "packets" or "pulses" or "distinct units" or "slugs", the movement of the boundary region between the fluid packets through the interrogation region may be synchronous with a pressure change at the remote valve or pump but not simultaneous with a change in pressure at the remote valve or pump, as for example, may occur due to compliance in the tubing.

In one embodiment, the fluid channel length of FIG. 1 may simultaneously contain multiple distinct units of sample and reference fluids as shown in FIG. 1. In other embodiments the fluid channel may simultaneously contain one of the following: (1) only sample or reference, (2) a partial distinct unit of reference and sample with a fluid boundary, or (3) a distinct unit of sample or reference, two fluid boundaries, and two partial distinct units of the fluid not in the distinct unit of sample or reference.

In another embodiment, the inlet channels may be fed by tubing or piping that is substantially on the order of or less than the length of the fluid channel length within the microfluidic cell containing the inlet channels and interrogation point.

It should be clear to those versed in the art that different microfluidic parameters, including physical geometries including the use of fluidic resistances and capacitances, different Reynolds number flows, and stream velocities and pressures be used to achieve a desired level of performance and signal modulation at the interrogation region.

Stream deflections may also be achieved by non-mechanical means, including the use of time varying electromagnetic fields to deflect a stream at the interrogation point, as, for example, by the use of a ferrofluid and magnetic fields.

FIGS. 38-41 show examples of fluid channel cross sections 310 showing the fluid boundary and in particular the shape of the fluid boundary that may be created by the no-slip boundary condition as the fluid boundary is moved laterally across the fluid channel and through the interrogation region 312 over time. In one embodiment, the fluid modulation may be sufficiently rapid in time across the interrogation region that there is a distinct no-slip boundary within the interrogation region during measurement of the fluid optical characteristics, that is, there is incomplete interdiffusion of fluids in the no-slip region. Note that the interrogation region probed by the optical beam may be primarily sample 314 or reference fluid 316 but may consist of sub-regions with a pathlength and fluid volume that is one of the liquids and other sub-regions where there is either a mixture of both fluids or the other fluid. Optical interrogation in the sub region volume that is primarily one fluid alternating almost purely to the second fluid may provide the greatest signal contrast. The fluid composition of the different sub-regions within the interrogation region changes over time with the motion of the fluid boundary. The presence of a no-slip region 318 creates a fluid boundary that is not a straight line or plane surface, but rather a curved surface that has surface segments that may be both orthogonal and non-orthogonal to the direction of motion of the fluid boundary, and changing over time and position of the fluid boundary, as shown in two dimensions in FIGS. 38-41. In one embodiment, the fluid boundary has segments that are non-parallel in orientation relative to the direction of fluid flow in the interrogation region during the sampling by the optical detector and that change over the period of a fluid modulation signal.

Multiple different embodiments can thus be constructed which may have certain advantages depending on the fluid conditions and analytes being measured and the overall performance requirements of a measurement system. The position of the fluid boundary (e.g. its average value position in the channel as shown in the figure), the modulation timing waveform, the amplitude of the boundary motion, the amount of fluid in the interrogation region due to the no-slip condition, and the variation in the volume of fluid across the interrogation region due to the no-slip condition both in the direction or orthogonal to the direction of fluid flow may be varied in the measurement system. The average position of the fluid boundary between the liquids may lie within the interrogation region or outside the interrogation region. The timing of the measurement (e.g. the optical transducer or detector signal integration time) may vary or depend on the position in time of the boundary region relative to the interrogation region. Note that FIGS. 38-41 are drawn for the general embodiment of FIGS. 19-20 parallel-streaming, and those versed in the art will see that that serial-streaming embodiments may also have a fluid boundary shape that is determined by the no-slip condition and that for serial-streaming the no-slip induced fluid boundary occurs on all four sides of the fluid channel whereas for the parallel-streaming a no-slip fluid boundary between different fluids may occur on only two sides of the channel (e.g. the top and bottom as shown in the cross section).

Figure 42:
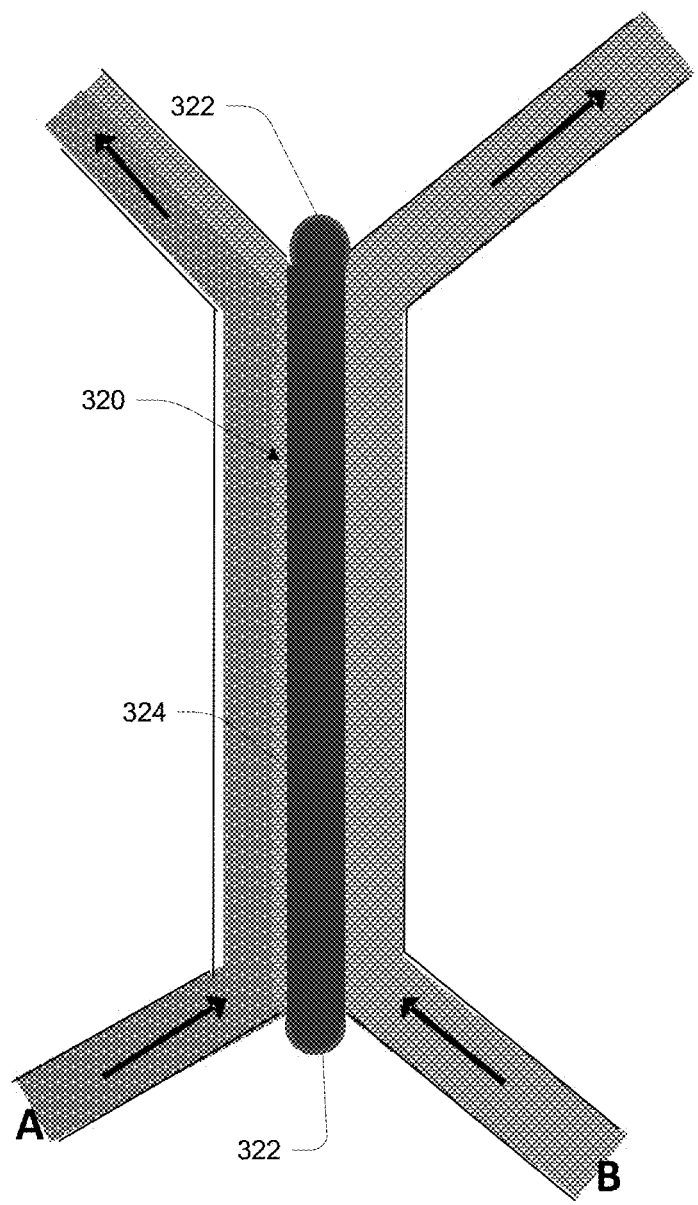

FIG. 42 illustrates an alternative configuration that can be used for increased measurement sensitivity in fluids with less absorption of the optical beam and thus may prefer increased pathlengths. The increased pathlength may be achieved by directing the optical beam in the direction of fluid flow down the channel 320, rather than across the channel substantially across the direction of fluid flow. One or more surfaces 322 of the channel may reflect the beam to assist in guiding the beam down the channel, or the fluid channel may be an integrated optical waveguide. In one embodiment, the beam may be collimated and travel down the channel 320 in a manner that substantially no or very little of the beam impinges on the side walls of the channel, such that the interrogation area 324 avoids any no-slip induced boundary regions. The interrogation area 324 may cross a boundary region between streams A and B at one of the beam entrances or exits from the channel. Thus the interrogation area may primarily be in the middle of the channel in the direction of fluid flow to avoid sampling of the no-slip regions on the channel sides and thereby improve measurement system sensitivity. The optical source and detector may be built into the sampling cell to create an integrated assembly or the optical beam may be directed into the channel (e.g. by using mirrors). The mirrors may be built into the cell using MEMS processes. In another embodiment and in a similar manner, the optical beam may be in an exit sampling channel as shown in FIGS. 34-35.

As also disclosed above, a second optical beam may be incident on the channel and in one embodiment the second optical beam may be at the same or different wavelength, may be orthogonal to the first optical beam (i.e. cross the cell right to left in the figure or in another embodiment traveling into the figure from the top side) or may measure a different optical property or characteristics of the channel (e.g. a different analyte or the location and movement of the fluid boundary region over time). The two beams may be used for simultaneous measurements or non-simultaneous measurements, and may originate from the same optical source.

In another embodiment, both measurement parameters and interrogation area may be varied to find the optimal conditions for measurement, either as part of a method of factory assembly and calibration for each system, or dynamically as part of the system operation under usage conditions. The optimization may be performed to reduce fringing effects from a coherent light source. The optimization may be performed to find the conditions for the best measurement signal to noise ratio.

Described herein is a method of measuring an analyte (e.g. oil or contaminant) in a liquid (the combination referred to as "analyte") with one or more of the following:

1. Creating adjacent spatial regions of a reference liquid and an analyte liquid (e.g. water reference and oil-in-water as analyte liquid, the reference and liquid being the same fluids except for the presence of the oil)
2. Moving the boundary region between the reference and analyte liquids through an interrogation region such that the interrogation region contains predominately the reference liquid and then the analyte liquid
3. Illuminating the interrogation region with a light source at one or more optical wavelengths (e.g. a wavelength of infrared laser light)
4. Measuring a resultant time varying interrogation signal with a transducer (e.g. an infrared detector measuring modulated transmitted or reflected light)
5. Using control electronics to process the time varying transducer signal over one or more oscillations of the boundary region position to calculate a desired analyte property (e.g. the amount in ppm of the analyte oil in the analyte liquid water as a form of spectroscopy)

The method may additionally be including one or more of the following:

1. Modulating the interrogation light source to improve analyte detection sensitivity
2. Adding multiple interrogation regions, each with their own illumination source at a different spectral wavelength or different transducer for measuring physical properties
3. Adding multiple interrogation regions, each with the same illumination source
4. Measuring the optical thickness of the reference liquid or analyte liquid at the interrogation region
   a. Using signal processing, simultaneously or sequentially, to correct the analyte property being measured to account for variations in optical thickness of the reference liquid, the analyte liquid or both.
5. Moving the boundary region by varying the pressure of the reference liquid, analyte liquid or both
   a. Generating the pressure variation through the use of a valve or a pump or both where the boundary region moves simultaneously or synchronously or both with the pressure variation at the pump or valve.
6. Modulating the light source in intensity or wavelength (or both), and using that modulation signal from the electronics to improve the accuracy of measurement of the analyte property.

Note that as described in previous embodiments, the fluid boundary region between the reference and analyte streams may be predominately continuous in nature as in parallel-streaming, that is the boundary region is in the general direction of the stream flow, is modulated in a direction orthogonal to the direction of fluid flow (i.e. across the channel rather than along the channel) and is present in a cross section of the liquid channel (i.e. a 2-D slice taken into page as shown in FIGS. 30-31 over at least the period or time of the measurement, with the boundary region is substantially or an average parallel (discounting no-slip boundaries proximate to surfaces), to the direction of fluid flow when traveling through the fluid channel). The fluid boundary region may also be discontinuous in nature (discounting no-slip boundaries proximate to surfaces), that is the boundary may be substantially or on average orthogonal to the direction of stream flow and traveling in the direction of fluid flow as may be in serial-streaming, and thus one or more boundary transitions may cross the interrogation region during the measurement or between measurements (i.e. the boundary region between fluids A and B crosses the interrogation region periodically with an orientation mostly orthogonal to the velocity vector of the fluid flow, ignoring the effect of any no-slip boundary condition). The boundary region may also be created where there is not continuous flow of liquid through the interrogation region as shown in FIG. 36 except with fluid A stationary for the period of an analyte measurement sample.

As previously disclosed, there is a no-slip velocity boundary condition at the sides of the fluid containing cell. As a result, the interrogation region, and thus the optical path through the cell, may contain both reference and analyte liquids even when the interface boundary between the two liquids is modulated fully across the interrogation region at the center of the optical path. One potential source of error in measuring the concentration of the analyte is in knowing the actual path length in the analyte containing liquid. In one embodiment, a known concentration of the analyte may be used to calculate the effective path length in the interrogation region for later use in the electronic signal processing for calculating the analyte concentration for unknown samples. The effective path length may vary as a function of the modulation depth (i.e. how far the boundary is moved), the modulation frequency, the amount of time analyte and reference liquids are in contact (i.e. distance from the channel merge to the interrogation region combined with flow velocities), the channel dimensions, or the chemical or physical properties of the analytes and liquids. The calibration may include a correction factor for variations in these parameters as well as the temperature of the liquids in the cell, the correction factor being determined through measurements taken with a variation in parameters and use of known liquid samples.

In one embodiment, the effective path length may be determined with an absorption measurement of a fluid with a known analyte concentration, and the effective pathlength used in the signal processing to determine an unknown analyte concentration. The pathlength may be measured by insertion of an analyte X1 of known concentration C1 into the analyte or reference fluid and measurement of the absorption at a wavelength Y1 other than the desired absorption wavelength YU of an unknown analyte XU with unknown concentration CU. Analytes XU and X1 may have a large measured differential absorption difference at both Y1 and YU.

An analyte X2 of known concentration C2 may be inserted into a first analyte fluid for determining the pathlength at wavelength Y1 (e.g. at the optimal wavelength for XU), without the presence of XU (note: X2 may be XU of known concentration). The pathlength thus determined may be used in determining the pathlength in a measurement of CU. Thus, more generally, the analyte or reference fluid may contain an analyte X1 with a known value C1 for the optical characteristic, and the measured value of the C1 and the actual known value of C1 are used in determining (e.g. through a calculated pathlength) the measured value of an analyte XU in the analyte fluid with an unknown value of the optical characteristic CU.

The pathlength of the reference liquid (or conversely the pathlength of the analyte liquid) in the interrogation region may vary over the dimensions of the interrogation region. One tunable light source or multiple light sources may be used at each of the wavelengths. One advantage of using the same light source to measure the optical pathlengths as to measure the analyte property of interest is that the same physical dimensions, that is the same interrogation region, may be measured. The pathlength may also be measured over just a part of the interrogation region, or even outside the interrogation region, and then a previously determined relationship between this "indirect" pathlength measurement and the effective pathlength over the interrogation region may be used to calculate the effective pathlength. Effective pathlength may take into account the variation in optical intensity as well as optical thicknesses of the liquids in the interrogation region to arrive at an average optical thickness that would be equivalent to that of uniform thickness and optical intensity.

Other methods of measuring effective pathlengths and then applying that pathlength in the calculation of an analyte property may be used. The reference liquid and analyte liquid may have different optical properties that include different indices of refraction or different optical reflectivities at certain optical wavelengths. This may be useful in measuring spatial dimensions, including optical pathlength, of the reference liquid due to the no-slip velocity boundary condition. The spatial dimensions may be measured directly in the interrogation region, or measured outside the interrogation region and used to calculate the dimensions within the interrogation region. The method of measuring the spatial dimensions may include looking at light reflected from the liquid boundary region due to the difference in refractive indices or from a high reflectivity difference between the two liquids at an optical wavelength. The method may further involve measuring the physical displacement of the incident and reflected light beams, and using the displacement coupled with an angle of incidence to calculate the optical thickness of the reference liquid. In another embodiment, a substance reflective at one wavelength and substantially non-absorbing at the desired wavelength of analyte absorption measurement may be inserted into one of the liquids.

As discussed previously, the light source in the interrogation region may be generated from coherent light or from an interferometer or other non-coherent light sources, each made up of time varying wavelengths of radiation, (e.g. as found in an FTIR instrument). The modulations of the fluid boundary regions, the switching frequency of the fluidic valves, or the variations of pressure at a fluidic pump in response to a controller modulation signal may vary synchronously or asynchronously with the time varying input radiation.

An infrared light source when transmitted through a highly absorptive liquid will be strongly attenuated as it passes through the microfluidic cell. This will result in heating of the liquid as the light is absorbed. In accordance with Beer Lambert Law, the liquid heating will be greatest proximate to the side of the cell closest to the light source and weakest on the opposite side due to attenuation of the light as it passes through the liquid. The cell window materials may be selected for higher thermal conductivity in order to reduced optical heating of the liquid, or may be coated with a material with higher conductivity than the underlying window material.

Heating of the liquid through optical absorption may result in a change in the optical transmission due to the temperature coefficient of absorptivity. If the reference streams are not identical in flow characteristics within the interrogation region, heating may result in a difference in transmission between reference and sample due solely to differential thermal heating. In one embodiment, the position of the interrogation region within the channel is adjusted to minimize (or null out) the difference in transmission. This may be a factory or field correction. In another embodiment, the differential flow characteristics may be adjusted through, for example changing the differential pressure between reference and sample to achieve the same null condition in the absence of the analyte of interest (i.e. the null is achieved for a reference versus reference condition).

In the same manner, the other stream asymmetries may be adjusted to achieve a desired null or non-zero differential transmission between reference and sample streams. For example, differences in refractive index between sample and reference may vary the effective signal collected by the detector, and the flow characteristics may be adjusted to achieve the desired differential detector signal.

In another embodiment, a heater in close proximity to one of the inlet channels may be used to differentially heat reference or sample stream. The differential heating may be used to null or reduced an optically induced differential signal in the interrogation region.

In another embodiment, the optical power may be adjusted as a function of optical wavelength. The optical power may be measured by a detector (i.e. through the use of a beam splitter to tap off part of the optical beam) and the laser operating parameters adjusted to maintain constant power as a function of optical beam wavelength in a tunable wavelength optical source. The optical power may be varied to "null" thermo-optically induced differential signals.

While one advantage of the embodiments as presented is that it allows the interrogation region and in particular a coherent light source to remain in a constant spatial position over the period of the measurement, it may also be advantageous to be able to move the position of the interrogation region between measurements or during the assembly and calibration of the system, or in the selection of multiple interrogation regions as previously disclosed. This may be done dynamically during system operation through the use of steering mirrors or other well know optical techniques for changing the direction of the beam such that it passes through a different location in the channel. In this manner, the system can locate the region of the channel that offers the best measurement for calculating the analyte parameters of interest. The best location may change over time as a result of surface contamination on the liquids or changes in pump performance, liquids being tested, reference liquids, liquid properties (e.g. Reynolds number, velocities), asymmetries in fluid pressure on the two sides of the channel, thermal absorption by the fluids or environmental conditions such as ambient or fluid temperatures. The channel may also be designed to have different dimensions (e.g. optical pathlengths) at different locations, and thus a moveable interrogation region may be advantageous, for example, to change the optical pathlength through the fluids. This may extend the dynamic range of the measurement to accommodate different analyte concentrations or different fluid absorption. A single light source may also be directed to different channel branches as shown in FIG. 34. The system may have a method of searching for the best interrogation region location in the channel for taking the measurement of interest that includes taking a measurement, moving the interrogation region in the fluid channel, taking another measurement, calculating the better measurement point, and then taking a series of measurements at a preferred measurement point. The optical measurement point may be one that provides a ratio of reference and sample intensities equal to a desired value (e.g. 1, as for example would be the target value when reference and sample have the same absorption at the interrogation wavelength). In one embodiment, the position, size or shape of the interrogation region in the fluid channel may be adjusted in a feedback loop over more than one fluid modulation signal period (i.e. a cycle of one signal and reference measurement) to set the measured optical characteristic at a desired value for subsequent operation of the fluid analyzer. The size or shape of the interrogation region may be changed through the use of lenses or other optical elements, or by spatial movement of the fluid cell and optical source relative to each other or relative to other optical elements within the analyzer.

In another embodiment, the system may be operated such that the location of the interrogation region is static, and the other system parameters are varied to determine the optimum parameters for a given set of measurement conditions as discussed previously. The system may have a method of searching for the best parameters for taking the measurement of interest that includes taking a measurement, changing an operating condition of the system (e.g. pump pressures, fluid velocities, fluid boundary location, fluid boundary modulation amplitude, fluid modulation waveform, detector measurement sampling period relative to the timing of the fluid modulation waveform, optical beam properties (e.g. wavelength, focal point or beam spatial dimensions, pulse amplitude, linewidth, wavelength modulation waveform, etc.), measurement period (e.g. optical detector integration time), etc.) calculating the better of the two measurement conditions, repeating the process as many times as necessary, and then taking a series of measurements at a preferred measurement point.

Embodiments incorporating ATR technology have been described, as well as embodiments employing multiple internal reflections. Serial streaming may be advantageous in both cases to provide a more "pure" (i.e. higher percentage of either reference or analyte fluids being measured during the transducer sampling time) but may have reduced measurement duty cycle or require reduced fluid velocities depending in part on the length of the channel in the interrogation region. For the ATR and parallel streaming, the ATR fluid sampling may be performed at a low duty cycle and in an interrogation region selected to insure an effective elimination of the no-slip fluid region in the interrogation region.

A measurement system is described for determining the properties of a liquid containing an analyte (e.g. oil or contaminant in water), comprising one or more of the following:

1. Adjacent spatial regions of a reference liquid and an analyte liquid in a fluid channel of a flow cell (e.g. water reference and oil-in-water as analyte liquid, the reference and liquid being the same fluids except for the presence of the oil)

2. A boundary region between the reference and analyte liquids that moves through an interrogation region such that the interrogation region contains predominately the reference liquid and then the analyte liquid 3. An interrogation region illuminated with a light source at one or more optical wavelengths (e.g. a wavelength of infrared laser light or the output beam of an interferometer)

4. A resultant time varying interrogation signal generated by a transducer (e.g. an infrared detector measuring modulated transmitted or reflected light) generated as a result of the motion of the boundary region 5. Measurement of the power of the optical source at one or more optical wavelengths, before or after passing through the optical cell 6. Electronics to process the time varying transducer signal generating from a known analyte concentration over one or more oscillations of the boundary region position to calculate an effective pathlength of the optical cell 7. Electronics to process the time varying transducer signal over one or more oscillations of the boundary region position and the effective pathlength to calculate a desired analyte property (e.g. the amount in ppm of the analyte oil in the analyte water solvent as a form of spectroscopy)

A measurement system may also comprise one or more of the following:

8. An interrogation light source modulated in amplitude or wavelength to improve analyte detection sensitivity 9. Multiple interrogation points, each with their own illumination source at a different spectral wavelength or different transducer for measuring physical properties 10. Multiple interrogation points, each with the same illumination source 11. Multiple interrogation points, each with a different optical pathlength through the interrogation region 12. A microfluidic channel where the reference liquid or analyte liquid or both have velocities that vary over time, and a measurement representative of the liquid velocity (e.g. through a transducer or an optical measurement of the fluid flow) provided to the electronics to adjust the processing of the detected signal 13. A microfluidic channel where the reference liquid or analyte liquid or both have velocities that vary over time, and a measurement representative of the liquid velocity (e.g. through a transducer or an optical measurement of the fluid flow) provided to the electronics to adjust the processing of the detected optical signal for the velocity variation 14. Signal processing operative to calculate the optical thickness of the reference liquid or analyte liquid in proximity to or in the interrogation region a. Further calculating, simultaneously or sequentially, to correct the analyte property being measured to account for variations in optical thickness of the reference liquid, the analyte liquid or both.

15. A boundary region spatially moved by varying the pressure of the reference liquid, analyte liquid or both a. Generating the pressure variation through the use of a valve or a pump or both where the boundary region moves simultaneously or synchronously with the pressure variation at the pump or valve.

b. Generating the pressure variation through the use of one-dimensional mechanical motion of a membrane or surface (a 1-D Pump) (e.g. a PZT style micropump)

i. The 1-D pump being located adjacent or substantially collocated with the interrogation region 1. The 1-D pump effective to move a flexible membrane of the flow cell ii. The 1-D pump including a fluid reservoir 1. The fluid reservoir replenished at a rate lower than the rate of pressure variation 2. The fluid reservoir being used to inject a known analyte solution iii. The embodiment further included a fluid reservoir or second pump located in proximity to the first pump 1. The reservoir or second pump containing the reference liquid and the first pump containing the analyte liquid 16. A feedback system including a measurement system for measuring at least one spatial location of the boundary region within a fluidic channel (or, in another embodiment some other operating parameter), a signal processor for using the boundary measurement to calculate a new operating parameter of the measurement system, and a control system for changing the operating parameter 17. Measurement system operating parameters or characteristics that may include: fluid velocity; fluid Reynolds number; fluid pressure; a fluid channel dimension, orifice or valve; optical beam power; interrogation region cross sectional area or volume; volume or ppm of cleaning fluid; interrogation region location in a channel; timing of the fluid modulation; timing of a transducer signal acquisition; timing of the optical beam wavelength, power or frequency variations; amount of optical beam focusing within the interrogation region; transducer location relative to the cell; choice of transducer in an array of transducers for use in calculating the analyte property of interest; selection of light source; selection of inlet or outlet channel; cell or channel temperature; power to an element for controlling the microfluidic cell or individual channel temperature; the frequency of calibration using a known input fluid or analyte property; phase of a coherent optical beam; optical fringes incident on the transducer; selection of optical pathlength in a multiple pathlength cell; phase of the fluid modulation relative to the transducer signal integration period; volume of liquid in a serial streaming packet; amount of contamination on a channel surface; amount of optical power incident on the cell that is not transmitted through the interrogation region to the transducer due to refection or other means other than analyte absorption; stroke length of a 1-D pump; motion of a flexible membrane 18. Modulating a light source in intensity or wavelength (or both), and using that modulation in the electronics to improve the accuracy of measurement of the analyte property.

19. A timing signal generated to indicate changes in fluid pressure, the timing signal used in the signal processing electronics to improve the sensitivity of the analyte measurement 20. A timing signal generated to indicate changes in fluid pressure, the timing signal used to modulate the interrogation light source amplitude, frequency or both.

a. The timing signal and light source modulation being synchronous

21. The transducer being one of a point detector, a linear detector array or a two dimensional array a. Wherein if a linear array is orientated parallel to or orthogonal to the principal direction of fluid flow b. Wherein if a linear array is orientated parallel to or orthogonal to the a boundary region between two fluids (e.g. the reference and analyte bearing fluid)

22. The process of the time varying signal further comprising a measurement of the reference liquid in the interrogation region, the analyte liquid in the interrogation region, calculating a ratio or difference of the two measurements (e.g. the transmission), and then calculating an average measurement over time based in part on the ratio or difference calculation.

23. A microfluidic cell including a heater or cooler (e.g. a thermoelectric cooler) for equilibrating the temperature of the reference and analyte fluids 24. A microfluidic cell including a heater or cooler (e.g. a thermoelectric cooler) for generating a temperature difference between the temperature of the reference and analyte fluids 25. A microfluidic cell including a heater or cooler (e.g. a thermoelectric cooler) for generating a change in the temperature of the fluids
   a. The temperature change being created between measurements of the analyte property
   b. The temperature change being induced along the length of the fluid channel in the flow cell
      i. The temperature change providing a different temperature at a second interrogation region that is different than the first interrogation region 26. Calibration of the microfluidic differential analyzer comprising the steps of
   a. Measuring an analyte property of a known concentration in a sample as a function of the temperature of the microfluidic cell, reference liquid or sample liquid
   b. Calculating a correction factor
   c. Measuring an analyte property of an unknown concentration in a sample at a measured temperature of the microfluidic cell, reference liquid or sample liquid
   d. Adjusting the measurement of the analyte property with the correction factor to arrive at a second measurement of the analyte property.

27. Optical pathlengths within an interrogation region varying in a direction substantially orthogonal to the direction of fluid flow and further including (1) at least a first spatial area with an optical path substantially (e.g. >95%) only of a first fluid and (2) a second spatial area with an optical path primarily (e.g. >60%) through a second fluid and secondarily (e.g. at least 5% but less than 40%) through the first fluid
   a. Where the first area and second spatial area together make up most (e.g. >60%) of the interrogation area measured with the optical source 28. An interrogation region with an effective optical pathlength that is increased by use of a reflection of the optical beam
   a. Where the reflection is off a microfluidic cell or fluidic channel surface
   b. Where the interrogation region includes a resonant optical cavity
   c. Where multiple bounces off one or more optical surfaces increases the pathlength
      i. To form one of the signal enhancing cells as is well known in the art of gas measurement (White cell, off axis cavity, etc.)

Adjusting the relative spatial positions of the light source incidence on the optical cell, the optical cell, the light cell detector, or optics to optimize analyzer performance when measuring fluids with different indices of refraction (e.g. to re-center the light on the detector when the light passes through the light cell at a non-perpendicular angle and the beam position at the detector is a function of the index of refraction of the liquid in the cell).

29. A method of adjusting a microfluidic analyzer for operation including
   a. Measuring a light absorption induced differential transmission between reference and sample streams
   b. Adjusting a focusing element to change the three dimensional volume of the interrogation region in the optical cell
   c. Measuring a light absorption induced differential transmission between reference and sample streams
   d. Selecting a focus for operation of the analyzer that results in a desired level of light absorption induced differential transmission 30. A method of adjusting a microfluidic analyzer for operation including
   a. Measuring a light absorption induced differential transmission between reference and sample streams, the reference and sample streams containing liquids with nominally the same zero or non-zero analyte concentration
   b. Adjusting a microfluidic analyzer operating parameter condition
   c. Measuring a light absorption induced differential transmission between reference and sample streams
   d. Selecting an operating parameter condition of the analyzer that results in a desired level of light absorption induced differential transmission Advantages and Other Points The optical cell window may be exactly perpendicular to the direction of optical propagation or tilted to prevent retroflection back into the optical source (e.g. to prevent laser feedback). Wedged windows and anti-reflection on window surfaces may also be used to reduce reflections and stray light in the analyzer.

The pathlength of the cell may be optimized to the laser power, analyte and solvent absorbance's, and matched to detector and electrical signal digitizer. As is known in the art for the transmission measurement of analytes in highly absorbing backgrounds, there is an optimum pathlength for the measurement that may be dependent on parameters such as the absorption of the background and analyte, thermal heating of the reference or sample, the laser power and the noise of the sensing detector and laser. For example, the optimum pathlength for an aqueous background may be in the range of 40 to hundreds of microns for a Mid-IR laser.

A simple transmission cell at low Reynolds number (<10 for example) may provide good laminar flow necessary for sample and reference segmentation and minimized mixing. Introduction of sample and reference immediately before the cell may limit mixing due to diffusion.

Small optical interrogation beam diameter allows for a small volume cell. Wider channels may be implemented while maintaining a low Reynolds number.

Can be used for multicomponent analysis and/or adjust for interferences by:
  1. Sampling multiple frequencies with multiple lasers sequentially, one frequency for a reference and sample measurement, or
  2. Sampling multiple frequencies sequentially with broadly tunable laser, one frequency for a reference and sample measurement, or
  3. Sampling with a rapidly scanning laser with at least one frequency scan of multiple wavelengths during each of a reference and sample measurement,
  and then applying chemometric methods to calculate values.

Additionally, in another embodiment not employing chemometrics, sampling methods can be used in a manner to measure a single discrete sample for multiple analytes by sequentially positioning the laser at different wavelengths to measure different analytes.

Pressure can be controlled within the cell to avoid optical artifacts being introduced by, for example pressure induced mechanical motion of the cell or cell walls.

Small cell volumes may make temperature control and stabilization of the liquids more rapid and accurate.

Those familiar with the art of micro/macro fluidics recognize a variety of techniques may be used to get the desired, volumes, laminar flow, temperature control, sampling speed, minimization of acoustic effects, amount of sample mixing, etc.

An exit valve may be used to assist in stopping flow and then allowing evacuation of the cell and injection of the next liquid to be measured.

Higher sample modulation allows the use of narrow band filtering to reject noise outside of modulation frequency including low frequency noise (drift)

Example applications include the following:
1. Fat/protein/sugars etc. in milk, a large market now utilizing very expensive instruments
2. Milk and dairy which requires high sensitivity and excellent temperature control; a microfluidics measurement is faster and more accurate due to rapid temperature stabilization of sample and high sensitivity
3. Oil in water with microfluidics offering direct measurement using the same methodology as ASTM method 7678 without the need for chemical extraction, and as well suitable for on line measurements
4. Analytes in blood and serum, interstitial fluids, urine, sweat
5. Direct measurement of important blood analytes in serum or whole blood
6. Contaminants in drinking water and water processing plants
7. Quality control of liquid pharmaceuticals
8. Quality control of liquid food products (e.g. juices)
9. Quality control and characterization of beer and wines While various embodiments of the invention have been particularly shown and described, it will be understood by those skilled in the art that various changes in form and details may be made therein without departing from the spirit and scope of the invention as defined by the appended claims.

What is claimed is:

1. A fluid analyzer, comprising:
an optical source and an optical detector defining a beam path of an optical beam;
a fluid flow cell disposed on the beam path defining an interrogation region in a fluid channel in the fluid flow cell in which the optical beam interacts with a fluid;
one or more flow-control devices configured to conduct an analyte fluid and a reference fluid stream through the fluid channel and the interrogation region, the flow-control device(s) being configured to manipulate the flow of a respective fluid in response to a fluid modulation signal to move a fluid boundary across the interrogation region, the fluid boundary separating the analyte and reference fluids when flowing together through the fluid channel; and
a controller operative (1) to generate the fluid modulation signal having a time-varying characteristic to cause the fluid boundary to be moved across the interrogation region accordingly, (2) to sample an output signal from the optical detector at one interval of the fluid modulation signal during which the interrogation region contains more analyte fluid than reference fluid and at a second interval during which the interrogation region contains more reference fluid than analyte fluid, thereby generating corresponding output signal samples, and (3) to determine from the output signal samples a measurement value indicative of an optically measured characteristic of the analyte fluid.

2. The fluid analyzer of claim 1, wherein the flow-control device(s) are configured to switch between the analyte and reference fluids in response to the fluid modulation signal to create distinct units of the analyte and reference fluids in alternating sequence in the fluid stream flowing through the fluid channel, successive distinct units being separated by a respective fluid boundary substantially non-parallel to a flow direction of the stream when flowing through the fluid channel.

3. The fluid analyzer of claim 2, wherein the fluid channel simultaneously contains a distinct unit of the analyte or reference fluid, and at least two partial distinct units of a fluid not the fluid of the distinct unit.

4. The fluid analyzer of claim 2, wherein the optical source is a scanning mirror interferometer, having a scanning mirror with scanning mirror motion being synchronous with the fluid modulation signal, and the controller uses a ratio of respective output signal samples for the analyte and reference fluids to determine the measurement value as a function of optical wavelength.

5. The fluid analyzer of claim 1, wherein the analyte and reference fluids flow together through the fluid channel with a fluid boundary component substantially parallel to a flow direction of the fluids in the fluid channel, and wherein the flow-control device(s) are configured to vary a relative pressure between the analyte and reference fluids in response to the fluid modulation signal to vary a position of the fluid boundary in a direction orthogonal to the flow direction in the fluid channel.

6. The fluid analyzer of claim 5, wherein the fluid boundary has segments that are non-parallel in orientation relative to the direction of fluid flow in the interrogation region during the sampling of the output signals and that change over the period of the fluid modulation signal.

7. The fluid analyzer of claim 5, wherein the propagation direction of the optical beam and the direction of fluid flow are substantially parallel.

8. The fluid analyzer of claim 5, wherein the interrogation region contains a region of analyte fluid between regions containing reference fluid, and an optical pathlength for determining the measurement value is adjusted for the regions containing reference fluid.

9. The fluid analyzer of claim 1, wherein the fluid flow velocity is reduced in the interrogation region during the sampling of the output signals relative to an average fluid flow velocity over one of multiple repeating cycles of fluid modulation.

10. The fluid analyzer of claim 1, wherein the optical source generates time varying coherent infrared light at multiple wavelengths synchronous with the fluid modulation signal.

11. The fluid analyzer of claim 1, wherein the fluid channel includes multiple interrogation regions, each interrogation region having a different optical transmission pathlength for the optical beam, and the controller is operative to (1) select an interrogation region as a function of a characteristic of the analyte or reference, and (2) determine from the samples of the output signals for the selected interrogation region the measurement value indicative of the optically measured characteristic of the analyte fluid.

12. The fluid analyzer of claim 11, wherein the optical beam is directed to each of the multiple interrogation regions through the use of (1) optical beam directing optical components to create simultaneous stationary optical beams or (2) mechanical motion of the optical source or optical beam directing optical components.

13. The fluid analyzer of claim 1, wherein the interrogation region is at a stationary point in the channel during one of multiple repeating cycles of the fluid modulation signal.

14. The fluid analyzer of claim 1, wherein the fluid flow cell includes a surface that at least partially reflects the optical beam, and the detector includes an array of detectors for detecting optical transmission in multiple fluidic pathlengths.

15. The fluid analyzer of claim 1, further including a transducer for detecting the fluid boundary and generating a fluid boundary motion signal for determining the timing of the sampling of the output signals relative to the fluid modulation signal.

16. The fluid analyzer of claim 1, wherein the fluid flow cell is temperature controlled, a fluid flow cell temperature determines temperatures of the analyte fluid and reference fluid in the interrogation region, and the measurement value is determined as a function of the respective temperatures of the analyte fluid and reference fluid.

17. The fluid analyzer of claim 1, wherein the analyte or reference fluid contains an analyte with a known value for the optical characteristic, and the measurement value of the analyte or reference fluid optical characteristic and the known value for the optical characteristic are used in determining the measurement value of an analyte fluid with an unknown value of the optical characteristic.

18. The fluid analyzer of claim 1, wherein a series of the measurement values are combined to improve measurement sensitivity, and a likely presence of a particle or bubble in the fluid channel is detected, and samples of the output signal likely to have values perturbed by the particle or bubble is excluded from the series of measurement values.

19. The fluid analyzer of claim 1, wherein the fluid flow cell includes an optical window transparent to the optical beam, and the analyte fluid includes a contaminant that adheres to the optical window thereby reducing a power of the optical beam in the interrogation region from a power that would occur without adherence of the contaminant, and wherein a ratio of respective samples of the output signal for the fluid and the reference fluid is substantially independent of a change in the quantity of window adhering contaminant.

20. The fluid analyzer of claim 1, wherein a cladding liquid substantially transparent to the optical beam is used to separate the analyte and reference fluids from a surface of the fluid channel in the interrogation region.

21. The fluid analyzer of claim 1, wherein the controller is operative to (1) sample an output signal from the detector during an interval in which the fluid boundary is within the interrogation region, and (2) to determine from the output signal the measurement value indicative of an optically measured characteristic of an interaction of the analyte fluid and reference fluid.

22. The fluid analyzer of claim 21, wherein the optically measured characteristic is a diffusion coefficient.

23. The fluid analyzer of claim 1, wherein an effective optical pathlength is determined by (1) operating the optical source at a first optical wavelength, and (2) determining a measurement value for an analyte of known concentration in the analyte fluid or reference fluid, the effective optical pathlength being used to determine the measurement value of the analyte fluid at a second optical wavelength of the optical beam.

24. The fluid analyzer of claim 1, wherein the analyte fluid and the reference fluid are chosen to have substantially the same optical characteristic and an operating condition of the fluid analyzer is adjusted in a feedback loop over more than one fluid modulation signal period to set the measured optical characteristic at a desired value for subsequent operation of the fluid analyzer.

25. The fluid analyzer of claim 1, wherein a surface area of the fluid boundary is reduced by use of a barrier, the barrier moving through the interrogation region in response to operation of the flow-control device(s).

26. The fluid analyzer of claim 1, wherein the determination of the measurement value uses a ratio of the analyte and reference signal samples to generate the measurement value substantially independent of the optical beam power.

27. The fluid analyzer of claim 1, wherein the position, size or shape of the interrogation region in the fluid channel is adjusted in a feedback loop over more than one fluid modulation signal period to set the measured optical characteristic at a desired value for subsequent operation of the fluid analyzer.

28. The fluid analyzer of claim 5, wherein the spatial positions of the analyte and reference fluids in the fluid channel are periodically reversed, and a corrected measured value is determined from the reversed and the unreversed measured values.

* * * * *